United States Patent [19]
Bott

[11] Patent Number: 4,676,641
[45] Date of Patent: Jun. 30, 1987

[54] SYSTEM FOR MEASURING THE SIZE DISTRIBUTION OF PARTICLES DISPERSED IN A FLUID

[75] Inventor: Steven E. Bott, Conway, Mass.

[73] Assignee: Coulter Electronics of New England, Inc., Amherst, Mass.

[21] Appl. No.: 817,048

[22] Filed: Jan. 8, 1986

[51] Int. Cl.[4] .................... G01N 15/02; G01N 21/49
[52] U.S. Cl. .................................... 356/336; 250/564;
250/574; 356/338; 356/340
[58] Field of Search .............. 356/336, 338, 340, 341,
356/343; 250/564, 565, 574

[56] References Cited

U.S. PATENT DOCUMENTS 3,621,220 11/1971 Ford.
4,158,234 6/1979 Grandchamp .................. 356/336 X

FOREIGN PATENT DOCUMENTS 2453832 10/1975 Fed. Rep. of Germany ...... 356/338

OTHER PUBLICATIONS

Hercher, "Virometer-an Instrument for the Measurement of the Size of Viruses Using an Optical Microscope", *Proc. SPIE*, vol. 126, pp. 17-22, 1977.
Pinder et al., "A Method of Measuring the Light Scattering of Solutions Containing Dust Particles", *J-Phys. E. Sci. Instrum.*, vol. 10, No. 4, pp. 400-403, 4/77.
Product Brochure: "Fast Automatic Measurement of Submicron Particles", Coulter Electronics Inc., 1982.
Product Brochure: "Model N4–Automation & Accuracy Down to 30 Angstroms", Coulter Electronics Inc., 1984.
Product Brochure: "Un Nouvel Instrument Francais", Amtec, date unknown.
Product Brochure: "System 4700", Malvern Instruments Limited, Feb., 1985.
B. E. Dahneke, "Measurement of Suspended Particles by Quasi-Elastic Light Scattering", John Wiley & Sons, New York, 1983.

*Primary Examiner*—Davis L. Willis
*Assistant Examiner*—Matthew W. Koren
*Attorney, Agent, or Firm*—Lahive & Cockfield

[57] ABSTRACT

An apparatus and method which provides a measure of the size distribution of particles dispersed in a fluid based upon an optimum combination of CLS measurements and DLS measurements. The measurement is characterized by relatively high resolution particle sizing. DLS data representative of the autocorrelation function, or power spectrum, of the detected intensity of scattered light at a plurality of angles about a sample, is optimally combined with CLS data representative of the average total detected intensity at those angles, to provide an angle-independent, high resolution size distribution v(r). The size distribution may be expressed in terms of the continuous function v(r) or the histogram v, and may represent distributions weighted by mass, volume, number, surface area, or other measures.

20 Claims, 9 Drawing Figures

| ORDINATE | ABSCISSA |
|---|---|
| 0.000E-01 | 3.000E+02 X |
| 0.000E-01 | 3.635E+02 X |
| 7.005E+02 | 4.403E+02 |
| 0.000E-01 | 5.335E+02 X |
| 0.000E-01 | 6.463E+02 X |
| 0.000E-01 | 7.830E+02 X |
| 3.496E+01 | 9.487E+02 X |
| 2.252E+00 | 1.149E+03 X |
| 0.000E-01 | 1.392E+03 X |
| 0.000E-01 | 1.687E+03 X |
| 0.000E-01 | 2.044E+03 X |
| 0.000E-01 | 2.476E+03 X |
| 0.000E-01 | 3.000E+03 X |
| 0.000E-01 | 3.636E+03 X |
| 0.000E-01 | 4.403E+03 X |
| 0.000E-01 | 5.335E+03 X |
| 0.000E-01 | 6.463E+03 X |
| 0.000E-01 | 7.830E+03 X |
| 0.000E-01 | 9.487E+03 X |
| 0.000E-01 | 1.149E+04 X |
| 0.000E-01 | 1.392E+04 X |
| 0.000E-01 | 1.687E+04 X |
| 0.000E-01 | 2.044E+04 X |
| 0.000E-01 | 2.476E+04 X |
| 0.000E-01 | 3.000E+04 X |

SYSTEM FOR MEASURING THE SIZE DISTRIBUTION OF PARTICLES DISPERSED IN A FLUID

FIELD OF THE INVENTION

This invention relates to light scattering instrumentation and more particularly to light scattering systems for measuring the size distribution of particles dispersed in a fluid.

BACKGROUND OF THE DISCLOSURE

There are several prior art techniques for measuring the distribution of the particle size in a sample by using light scattering. Generally, to measure the sizes of individual particles, for example, in a flowing stream of a liquid or gas, the particle-containing sample is illuminated by a constant light source and the intensity of light scattered by the particle is detected. A particle scatters the light by an amount directly related to the particle size; in general, bigger particles scatter more light than smaller particles. The relation between the amount of scattering and particle size may be determined either from theoretical calculations or through calibration process. With knowledge of this relation, for a single particle at a time, the detected scattered light intensity provides a direct measure of the particle size. The distribution of particle sizes in a sample may be determined by individually passing each particle in the sample, or a suitable portion of the sample, through the scattered light detection apparatus and tabulating the sizes of the various particles. In practice, this method is generally restricted to particles greater than 0.5 microns. Moreover, this method is relatively slow since particles must be detected individually. This technique is referred to in the prior art as optical particle counting (OPC).

A second prior art technique of particle sizing by light scattering is referred to as static or "classical" light scattering (CLS). This method is based upon illumination of a sample containing the particles-to-be-sized followed by the measurement of the intensity of scattered light at several predetermined angles. Because of intra-particle destructive interference, the intensity of light scattered from a particle depends on both the size and composition of the particle and the angle at which the measurement is made. This method of particle sizing based on the angular dependence of the scattered intensity can be used to measure the size distribution of a group of particles, as opposed to the first method noted above which is restricted to individual particles.

To implement the CLS measurement method, a sample of particles dispersed in a fluid is illuminated along an input axis, and the intensity of scattered light is measured at several predetermined angles. The scattered light intensity at each angle may be measured simultaneously with a multitude of detectors or consecutively, by moving a single detector around the sample to permit measurement of the intensity at each desired angle.

For large particles, for example, having diameters greater than 1 micron, the scattered light flux is concentrated in the forward direction relative to the input axis. Instruments for sizing large particles are referred to as laser diffraction devices. For sizing of smaller particles, for example, having diameters as low as 0.2 microns, the scattered light flux has significant magnitude both at lower and higher scattering angles relative to the input axis. The angular intensity measurements used on smaller particles are termed total integrated, or average, intensity measurements and may be displayed in a form known as Zimm plots.

A third prior art technique for particle sizing by light scattering is dynamic light scattering (DLS), also known as photon correlation spectroscopy (PCS) or quasi-elastic light scattering (QELS). See B. E. Dahneke, "Measurement of Suspended Particles by Quasi-Elastic Light Scattering," John Wiley & Sons, Inc., New York, 1983. This technique is based on measuring the time-fluctuations of the intensity of light scattered from an illuminated sample containing a group of particles which are diffusing through a fluid, that is, randomly moving due to collisions with solvent molecules and other particles. For example, the particles may be macromolecules dissolved in a liquid, where the macromolecules may be ionized by the loss of a small number of charged atoms.

In accordance with the DLS technique, scattered light intensity is measured as a function of time at a selected angle with respect to an illumination input axis. The light intensity detected at any instant at the detector is dependent on the interference between the light scattered from each illuminated particle in the scattering volume. As the particles randomly diffuse through the solution, the interference of the light scattered from them changes and the intensity at the detector therefore fluctuates. Since smaller particles diffuse faster, the fluctuations resulting from the motion of relatively small particles vary faster than those resulting from the motion of larger particles. Thus, by measuring the time variation of the scattered light fluctuations at the detector, information representative of the distribution of particle sizes is available. More particularly, the autocorrelation function of the measured intensity is related to the distribution of particle sizes in the fluid. Conventional DLS instruments such as the Model N4 photon correlation spectrometer manufactured by Coulter Electronics, Inc., Hialeah, Fla., provide autocorrelation signals for the detected intensity suitable for measuring distributions including particle sizes as low as 0.003 microns. Accordingly, such devices have a size measuring range extending considerably below the above-noted individual particle and CLS methods.

Particle sizing measurements by the known DLS techniques are generally made in the following manner. The particles-to-be-sized are suspended or dissolved in a fluid, forming a sample. The sample is illuminated by a laser beam directed along an input axis. Although a laser is generally used to generate the beam, a non-coherent light source may alternatively be used.

The light scattered from the particles in the sample is detected by a photodetector, such as a photomultiplier, which is positioned at a predetermined angle. The particular angle may be selected by the operator, but usually only one angle is measured at a time. The photodetector produces a signal which varies with time as the scattered light intensity incident on the photodetector varies. This time-varying signal is applied to an autocorrelator analyzer, to compute the autocorrelation function of the photodetector signal. Typically, the autocorrelator computes the value of the autocorrelation function of the detected scattered light at as many as one hundred discrete time points. This autocorrelation function contains the information about the fluctuations in the detected scattered light, from which information about the distribution of particle sizes in the sample can be extracted. Thus, the autocorrelation function (acf) is the raw data of a DLS measurement. While most conventional DLS measurements are performed using this autocorrelation step, it is known that the acf of the intensity signal corresponds to the Fourier Transform of the power spectrum of that signal. Accordingly, a spectrum analyzer may be used in place of the autocorrelator to generate a power spectrum signal including the same information representative of the particle size distribution as is resident in the autocorrelation function. The frequency domain information resident in the power spectrum signal can be used to determine the particle size distribution.

In the prior art, there are several techniques for extracting the particle size distribution from the acf. For use with these techniques, the relationship between the acf and the size distribution can be expressed as:

$$g(t) = K(x(r)) \quad (1)$$

where $g(t)$ is the acf (or a function closely related to the acf), $x(r)$ is the sought distribution of particle sizes ($x$ is a function of $r$, the particle radius), and $K$ is a function (or operator, linear or non-linear) which relates particle size to the acf. Thus, given the exact form of $K$, the autocorrelation function resulting from any distribution, $x(r)$, of particle sizes would be known.

Since the acf, $g(t)$, is what is actually measured in practice, the above relation must be inverted to yield the particle size distribution:

$$x(r) = K^{-1}(g(t)) \quad (2)$$

Accordingly, for the measured acf for a sample of particles, the size distribution for those particles can be extracted by applying the operator $K^{-1}$ to the measured acf, $g(t)$. The operator $K^{-1}$ is the generalized inverse of the operator $K$. In practice however, the acf is "ill-conditioned" so that the inversion process is generally difficult and complex, although there are a number of known techniques for performing the inversion.

An example of the form $K^{-1}$ for one particular commonly used prior art extraction technique is:

$$x = (K^t K + \alpha H)^{-1} K^t q \quad (3)$$

In this example, x is a vector whose components are the proportions of the particles of each size, g is a vector whose components are the values of the acf at different points in time, as computed by the autocorrelator, $\underline{K}$ is a matrix relating x to g, and H is a matrix which increases the conditioning of the inversion. $K^t$ is the transpose of the matrix K. Alpha ($\alpha$) controls the amount of conditioning imposed on the solution. The inverse operator $K^{-1}$ in this case can be written $K^- = (K^t K + \alpha H)^{-1} K^t$, where alpha ($\alpha$) is a smoothing parameter determined conventionally. The inversion is usually performed along with some non-negativity constraints imposed on the solution; these constraints are formally part of the inverse operator $K^{-1}$. Other known methods for inversion are the histogram method, the singular value decomposition method, the delta function method, and the cubic spline method.

The size distribution, $x(r)$, obtained from this extraction or "inversion" process can be expressed either as a continuous distribution as implied by $(r)$, where the distribution is defined for particles of any size, or as a discrete size histogram expressed by the vector $\underline{x}$ where the distribution of particle sizes is defined at only a set number of particle sizes. The vector $\underline{x}$ is representative of a group of numbers $(x(r_1), x(r_2), \ldots, x(r_n))$ giving the relative proportion of scattered light intensity from particles of size $r_1, r_2, \ldots, r_n$, respectively. The size distribution $(r)$ is referred to as a size histogram $\underline{x}$ herein below.

The size distribution $x(r)$ and size histogram, $\underline{x}$, are "intensity weighted" functions since these are representative of the relative proportion of particles as characterized by the relative amount of scattering intensity from particles of each size. However, these intensity weighted functions are dependent on the angle at which the measurement of scattered light was made. That is, the apparent proportion of particles of each size, as evidenced by the scattered light intensity contribution of particles of different sizes, depends on the angle at which the measurement is made. Thus, size distributions made at different angles cannot be directly compared using the intensity weighted distribution $x(r)$ or histogram x.

Accordingly, if the amount of light scattered per particle, as a function of the scattering angle, is known, either through theoretical calculations or by an empirical method, the intensity weighted size distributions $x(r)$ and histogram $\underline{x}$ at each angle can be directly compared by first converting those functions to corresponding mass, volume, or number weighted size distributions. For example, the intensity weighted histogram $\underline{x}$ may be converted in accordance with:

$$\underline{v} = C\underline{x}$$

In this expression, $\underline{v}$ is the mass, volume or number weighted size histogram and C is the conversion matrix between the intensity weighted histogram, $\underline{x}$, and the mass, volume or number weighted histogram, $\underline{v}$. Similarly, the size distribution $x(r)$ may be converted into a corresponding mass, volume or number distribution function $v(r)$. Since all of these converted histograms and distribution functions provide the desired angle-independent information about the size distribution particles, they are referred to generally below as $\underline{v}$ and $v(r)$, respectively.

A volume weighted histogram and distribution function provide a measure of the proportion of the total volume of particles in a sample as a function of particle size. For example, 50% of the volume of a sample of particles might come from particles of size 0.1 micron and the remaining 50% from particles of size 0.3 microns. Similarly, the mass weighted histograms and distributions provide a measure of the mass of particles in a sample as a function of size and the number weighted histograms and distribution of the numbers of particles in a sample as a function of size. For particles of the same density, the mass and volume weighted histograms and functions are the same. Volume, mass and number weighted size histograms and distributions are generally more useful than the corresponding intensity weighted size histograms or distributions since the former relate to quantities which can be directly measured by other means.

All of the prior art light scattering measurement techniques are characterized by low resolution and poor reproducibility, the principal drawbacks of such methods. With respect to DLS sizing measurements, efforts have been made to try to increase the resolution. The general methods used to increase resolution either attempt to improve the signal-to-noise ratio of the measurement by collecting intensity data over a long period or over a large number of short periods and then averaging the results, or by using intensity data collected at several angles.

With the latter method, the data collected at different angles are substantially independent, and therefore data collected at one angle complement those collected at other angles. For example, data collected at lower scattering angles are generally more sensitive to the presence of large particles in the sample while, conversely, data collected at large scattering angles are more sensitive to the presence of smaller particles. A sample containing both large and small particles can therefore be accurately sized by using the data from two or more angles, where relatively lower angle or angles provide information about the larger particles and relatively high angle or angles provide information about the smaller particles. In contrast, measurement at a single low angle would provide relatively little and possibly obscured information about the smaller particles and hence the sizing resolution would be poor.

The prior art method of using several angles to enhance the sizing resolution involves simply making measurements at two or more angles and averaging the volume weighted histograms resulting from the measurements made at the two or more angles. Symbolically, the process of combining information obtained at several scattering angles by averaging results can be expressed by:

$$\underline{x}_1 = K^{-1}(g_1(t), \theta_1) \quad (4)$$
$$\underline{x}_2 = K^{-1}(g_2(t), \theta_2)$$
$$\vdots$$
$$\underline{x}_m = K^{-1}(g_m(t), \theta_m)$$

where the subscripts 1,2, ... m refer to measurements made at the scattering angles $\theta_1$ through $\theta_m$. The inclusion of $\theta$ as an argument of the operator $K^{-1}$ indicates that the inversion process, that is, the operator $K^{-1}$, depends on the scattering angles. Each of the m intensity weighted histograms, $\underline{x}_1, \ldots, \underline{x}_m$, may be converted to an angle-independent volume weighted histogram, $\underline{v}_1, \ldots, \underline{v}_m$, and then the m volume weighted histograms may be averaged to produce the "enhanced" resolution result, $\underline{v}$:

$$\underline{v} = (1/m)[\underline{v}_1 + \underline{v}_2 + \ldots + \underline{v}_m]$$

However, this volume weighted distribution, $\underline{v}$, is not necessarily the solution which is the best fit to all the data. The size resolution obtainable for a single measurement at a single angle is quite low and the presence of particles of some sizes may not be detected at some angles. Thus, even when the intensity histograms are converted to volume histograms, the histograms obtained at different angles may give very different and apparently contradictory information.

It is an object of the present invention to provide an improved apparatus and method for measuring the distribution of particle sizes dispersed in a fluid.

Another object is to provide a particle sized distribution measuring apparatus and method characterized by relatively high resolution.

SUMMARY OF THE INVENTION

Briefly, the present invention is an apparatus and method which provides a measure of the size distribution of particles dispersed in a fluid based upon an optimum combination of CLS measurements and DLS measurements, providing a resultant measurement characterized by relatively high resolution particle sizing. More particularly, in accordance with the invention, DLS data representative of the autocorrelation function, or power spectrum, of the detected intensity of scattered light at a plurality of angles about a sample, is optimally combined with CLS data representative of the average total detected intensity at those angles, to provide an angle-independent, high resolution size distribution v(r). The size distribution may be expressed in terms of the continuous function v(r) or the histogram $\underline{v}$, and may represent distributions weighted by mass, volume, number, surface area, or other measures.

By way of example, in combining the DLS and CLS data, an angle independent volume weighted histogram may be determined from:

$$\underline{v} = J^{-1}(g_1(t), g_2(t), \ldots, g_m(t); i(\theta_1), \ldots, i(\theta_m), i(\theta_{m+1}), \ldots i(\theta_n))$$

where $g_1(t), \ldots, g_m(t)$ are the determined autocorrelations of the detected light intensities at m scattering angles $\theta_1, \ldots, \theta_m$, and where $i(\theta_1), \ldots, i(\theta_m), i(\theta_{m+1}), \ldots, i(\theta_{m+n})$ are the detected average intensities at the respective m scattering angles; $\theta_1, \ldots, \theta_m$ as well as n additional angles $\theta_{m+1}, \ldots, \theta_{m+n}$, where m is an integer equal to or greater than one and n is an integer equal to or greater than zero. In this form of the invention, the DLS measurements are made at m angles and the CLS measurements are made at m+n angles, including the same angles at which DLS measurements are made. $J^{-1}$ is a single operator which acts simultaneously on all of the autocorrelation functions and average intensity values to provide the "best fit" to all the data. This is in contrast to the m separate $K^{-1}$ operators, one for each angle, set forth in equations (4) above. With the present invention, the operator $J^{-1}$ incorporates the information from the CLS measurements as well as the independent information from the DLS measurements, in a manner appropriately normalizing the autocorrelation functions measured at the different scattering angles.

The resultant distribution, $\underline{v}$, based upon the $J^{-1}$ transformation of the autocorrelation functions and the classical scattered intensities, simultaneously in a single procedure, provides an increase in the sizing resolution of the determined particle distributions compared to the prior art techniques which are based upon either the autocorrelation functions of the classical scattering intensities, but not both.

Briefly, according to the invention, a system is provided for measuring the size distribution v(r) of particles dispersed in a fluid sample, where r is representative of particle size. The system includes means for illuminating the sample with a light beam directed along an input axis. Either a coherent or a non-coherent light source may be used.

A light detector detects the intensity of light from the light beam at m points angularly dispersed from said input axis at a plurality of angles $\theta_1, \ldots, \theta_m$, where m is an integer equal to or greater than one. The detector generates m intensity signals, each of the intensity signals being representative of the detected intensity of the light from the light beam as a function of time at a corresponding one of the m points. In various forms, the invention may be embodied in a homodyne or a heterodyne configuration. In the homodyne form, only scattered light is detected at the m points during the intensity signal measurements, while in the heterodyne form, a portion of the beam is directly incident on the detector at the m points, so that the intensity signal corresponds to a beat signal resulting from both scattered and non-scattered portions of the light beam.

In one form, an autocorrelation processor generates m correlation signals each of the correlation signals being representative of the autocorrelation function of a corresponding one of the intensity signals. Each of the correlation signals equals an associated transformation $J_i$ of the distribution $v(r)$, where $i = 1, \ldots, m$. The transformations may be linear or non-linear. Since the autocorrelation functions for the intensity signals are the Fourier Transforms of the power spectra of those signals, the autocorrelation processor is, in one form of the invention, an autocorrelator which directly generates the m correlation signals as m time domain autocorrelation signals $g_i(t)$, where t is time and $i = 1, \ldots, m$. In other forms, the autocorrelation processor includes a spectrum analyzer which generates the m correlation signals as m frequency domain power spectrum signals $G_i(f)$, where f is frequency and $i = 1, \ldots, m$. Since the power spectrum signal is the Fourier Transform of the autocorrelation signal, the power spectrum signals $G_i(f)$ may be used to provide the same information as the autocorrelation signals $g_i(t)$.

A light detector also detects the time average intensity of scattered light from the light beam at the m points as well as n additional points angularly displaced from the input axis, where n is an integer greater than or equal to zero. The latter detector generates average signals representative of the time average of the intensity of scattered light detected at the respective m+n points.

A size processor, responsive to the correlation signals and the average signals, generates a signal representative of the distribution $v(r)$. The size processor generates a composite correlation signal representative of a weighted direct sum of the m correlation signals. The size processor determines a composite transformation operator $J^{-1}$ which is related to the transformations $J_i$ and the n average signals.

The size processor transforms the composite correlation signal in accordance with the determined composite transformation operator thereby providing a resultant signal which incorporates the size distribution information of both the CLS and DLS data and is representative of the size distribution $v(r)$. In accordance with the invention, either the composite correlation signal or the composite transformation operator is substantially scaled to the average intensities of the scattered light at the respective ones of the m points. This scaling, or normalization, permits the DLS data represented by the composite correlation signal to be optimally combined with the CLS data represented by the average signals.

In one form of the invention, the transformations $J_i$ are linear transformations and the composite transformation operator $J^{-1}$ is the generalized inverse of the operator corresponding to the direct sum of the operators for the associated transformations $J_i$. The inverse transformation operator $J^{-1}$ may correspond to the inverse of the matrix corresponding to the direct sum of the associated transformations $J_i$. Alternatively, the operator $J^{-1}$ may correspond to $[J^tJ + \alpha H]^{-1}J^t$ where J is the matrix corresponding to the direct sum of the matrices coresponding to the associated transformations $J_i$, $J^t$ is the transpose of the matrix J, H is a conditioning matrix, and alpha ($\alpha$) is a smoothing parameter. Further, all components of the vector representative of the distribution $v(r)$ may be constrained to be greater than or equal to zero.

In another form, the associated transformations are non-linear, with the size distribution being characterized by $v(r,\underline{p})$, where $\underline{p}$ is a characterization parameter vector having k components. In this form, the composite transformation operator $J^{-1}$ is the $\underline{p}$ solution algorithm for $$\frac{\partial}{\partial p_l} \sum_{i=1}^{m} \sum_{j=1}^{q} \{J_{ij}[v(r,\underline{p})] - g_i(t_j)\}^2 = 0, l = 1, \ldots, k$$

where i is an inteqer $1, \ldots, m$, j is an integer $1, \ldots, q$, l is an integer $1, \ldots, k$, $p_e$ is the $l^{th}$ component of $\underline{p}$ and where $g_i(t_j)$ is the autocorrelation function of the intensity signal for the $i^{th}$ of said angle at the $j^{th}$ time interval and $J_{ij}$ is an operator related to the associated transformations. The model size distribution $v(r,\underline{p})$ may for example be characterized in terms of parameters $\bar{r}$ and $\sigma$, the mean particle size of the actual size distribution, and the standard deviation of the actual size distribution, respectively. The solution algorithm for the $p_l$ minimizes the squares of the residuals $J_{ij}[v(r,\underline{p})] - g_i(t_j)$ for the various points in time $t_j$ for the various acf's $g_i$. More particularly, $v(r,\underline{p})$ may have the form:

$$v(r,\underline{p}) = \sqrt{\frac{1}{2\pi\sigma^2}} \, e^{-(r-\bar{r})^2/2\sigma^2}$$

where the $J_{ij}$ operator has the form:

$$\int_0^\infty dr e^{-\Gamma(r,\theta_i)t_j}$$

where $\Gamma(r,\theta_i)$ has the form:

$$\Gamma(r,\theta_i) = \left[\frac{4\pi n}{\lambda} \sin \frac{1}{2} \theta_i\right]^2 \frac{k_B T}{6\pi \eta r}$$

where n is the refractive index of the sample, $\lambda$ is the wavelength of the light illuminating the sample, $k_B$ is Boltzman's constant, $\sigma$ is the viscosity of the sample and T is absolute temperature.

In another form, the composite correlation signal operator controls the weighted direct sum of the m correlation signals to be unity normalized and the composite transformation operator is substantially scaled to the average intensities of light scattered from the light beam at the respective ones of the m points. In yet another form, the composite correlation signal generator controls the weighted direct sum of the m correlation signals to be substantially scaled to the average intensities of light scattered from the light beam at the respective ones of the m points.

In other forms of the invention, the general method of using informtion exacted from measurements at two or more scattering angles can be applied to determine size and shape information about particles which are rod-like, ellipsoids or other forms, including "Gaussian coils".

In other forms of the invention, instead of making CLS and DLS measurements at two or more scattering angles, such measurements may be made at one angle under different sets of conditions, for example, different temperatures or hydrodynamic solution characteristics or polarization of the light beam, providing complementary information which is processed to yield enhanced particle characteristic resolution for a wide variety of dynamic systems.

BRIEF DESCRIPTION OF THE DRAWINGS

The foregoing and other objects of this invention, the various features thereof, as well as the invention itself, may be more fully understood from the following description, when read together with the accompanying drawings, in which.

DESCRIPTION OF THE PREFERRED EMBODIMENT

Figure 1:
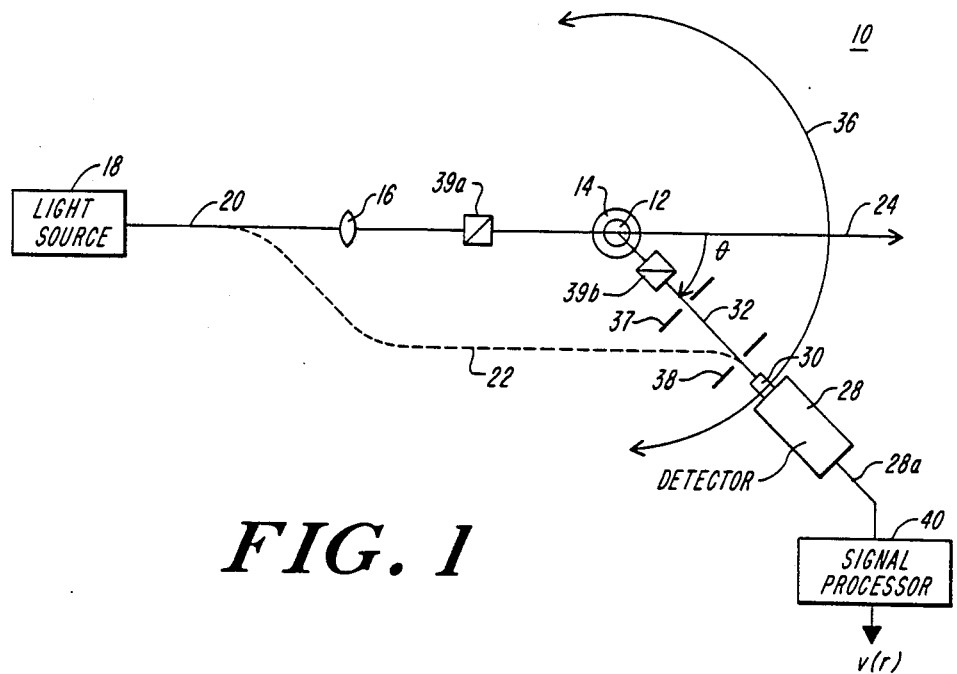
FIG. 1 shows in schematic form, an exemplary system embodying of the present invention.

FIG. 1 shows an exemplary system 10 in accordance with the invention. The system 10 provides an output signal representative of the size distribution of particles v(r) dispersed in a fluid sample 12, where r is representative of particle size. The sample may, for example, include discrete particles or macromolecules suspended in a liquid, or may include ionized macromolecules in a solvent, or may include discrete particles in an aerosol, or any configuration wherein the particles-to-be-sized are dispersed in a fluid, and are subject to Brownian motion in that fluid.

In the embodiment of FIG. 1, the sample 12 is positioned within a bath chamber 14 filled with a temperature-controlled index of refraction matching medium. The system 10 includes a light source 18 which provides a collimated light beam 20 directed along an input axis 24 and focussed by lens 16 onto the sample 12. In the presently described embodiment, the light source 18 is a laser, although in other forms of the invention, a non-coherent light source may be used. The present embodiment is a homodyne configuration in which substantially no non-scattered light is permitted to reach detector 30. In a heterodyne form of the invention, portion of the light beam from source 18 may be coupled directly to the sensor 30, for example, by a fiber optic link indicated by the broken line 22 in FIG. 1.

A light detector 28 includes a sensor 30 having a sensing axis 32 which is positionable at a plurality of points equidistant from and dispersed angularly about the sample 12 along an arc 36. As shown, the input axis 32 is displaced by an angle $\theta$ with respect to axis 24. In various forms of the invention, a detector may be successively positionable along arc 36, or alternatively, a plurality of light detectors might be fixedly positioned at discrete points along the arc 36. The detector 28 provides output signals along lines 28a to a signal processor 40. In the present embodiment, aperture defining devices 37 and 38 are positioned with respect to sensor 30 and the axis 32 in a manner restricting the light detected at sensor 30 to be within a predetermined coherence area.

In addition, the present embodiment includes a pair of polarizers 39a and 39b positioned along the axis 24 before the sample and along the axis 32, respectively. The filters 39a and 39b permit passage only of portions of the light beam and scattered light, respectively, having predetermined polarization. By selectively controlling the polarization angle of these filters, substantially independent intensity signals may be generated for a single angle $\theta$ for each orthogonal polarization angle. For example, in one form, the filter 39a passes right circularly polarized light and the filter 39b may be selectively adapted to pass right circularly polarized light or left circularly polarized light. Alternatively, the filter 39a passes vertically polarized light and the filter 39b may be selectively adapted to pass light characterized by one of two different orthogonal polarizations.

Figure 2:
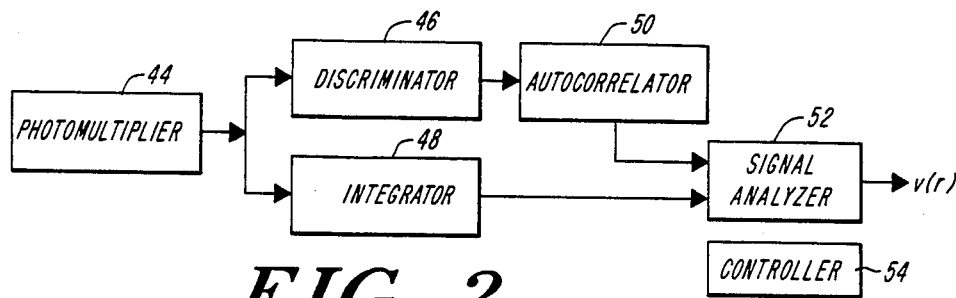
FIG. 2 shows, in block diagram form, an embodiment of the detector and signal processor of the system of FIG. 1.

FIG. 2 shows one form for the detector 28 and the signal processor 40 in which the detector 28 includes a photomultiplier 44 and associated pulse discriminator 46 and an integrator 48. In this form, the signal processor 40 includes an autocorrelator 50, a signal analyzer 52 and a controller 54.

Figure 3:
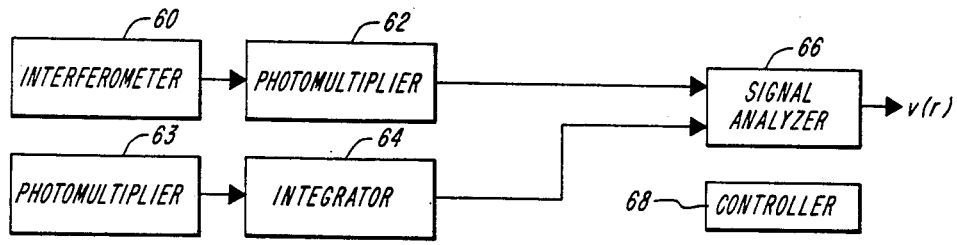
FIG. 3 shows, in block diagram form, another embodiment of the detector and signal processor of the system of FIG. 1.

FIG. 3 shows an alternate form in which the detector 28 includes an interferometer 60 and a photomultiplier 62, which provide a signal representative of the power spectrum of the light intensity at the detector 30, and a photomultiplier 63 and an integretor 64, which provide a signal representative of the time average of the light intensity at detector 30. The signal processor 40 includes a signal analyzer 66 and a controller 68. In FIGS. 2 and 3, the signal analyzers provide the output signal representative of the size distribution v(r).

In operation, briefly, the light source 18 illuminates the sample 12 along the input axis 24 and the sensor 30 of detector 28 detects the intensity of the light scattered by the sample at a plurality of points along arc 36. The intensity measured at the detector 28 is an interference pattern resulting from the in phase contributions of the light scattered from each molecule in the scattering volume of sample 12. In liquid or gaseous samples, the molecules are in motion and the interference pattern at the detector 28 is modulated by the motions of the scattering particles. In the absence of external fields, the motions of the particles are random, and are due just to thermal fluctuations. The fluctuations in scattered electric field at the detector caused by these random motions comprise a stationary random process. The second moment of the process is defined by $$g(t) = \lim_{T \to \infty} \frac{1}{T} \int_{-T/2}^{T/2} e^*(\tau)e(t + \tau)d\tau \quad (1)$$

where $e(\tau)$ is the electric field of the scattered light at the detector 28 at time $\tau$. g(t) is the autocorrelation function (hereinafter abbreviated "acf") of the process. The acf is a measure of the correlation between the configuration of the scattering molecules at a given time compared to that at any later time, e.g. at very short delay times, the configuration of particles as well as the scattered electric field measured at the detector 28 closely resembles the original configuration; as time passes, that resemblance diminishes. Because the degree of correlation depends on the speed with which and the mechanism by which the configurations change, the acf provides characterization of the dynamics of the particles in the sample. In the configuration of FIG. 2, the acf of the scattered light is determined by a digital correlator 50. Alternatively, in the configuration of FIG. 3, the photomultiplier-discriminator- autocorrelator elements of FIG. 2 are replaced by the interferometer 60 and photomultiplier 62. In the latter configuration, the power spectrum, which is the Fourier Transform of the acf is measured. In both the configuration of FIG. 2 and that of FIG. 3, the information obtained is equivalent and both the acf and power spectrum signals are referred to herein as the DLS data. In practice, the choice between the two forms is determined by the rapidity of fluctuations in the light scattered by the sample 12. Preferably, fluctuations decaying on a time scale slower than 0.01 microseconds are measured by autocorrelation and those faster than 0.01 microseconds are measured by interferometry.

The photomultiplier 44 and integrator 48 of FIG. 2 and the photomultiplier 63 and integrator 64 of FIG. 3 provide signals representative of the average detected intensity at the detector 30. Those signals are referred to herein as the CLS data.

The elements 18, 28, 44, 46, 48 and 50 of the system 10 of FIGS. 1 and 2 may be implemented in part by commercially available devices, such as the Model LSA2+ photon correlation spectrometer and Model 1096 Correlator, manufactured by Langley Ford Instruments, division of Coulter Electronics of New England, Inc., Amherst, Mass. Alternatively, these elements may be implemented by the Coulter Model N4 photon correlation spectrometer, or by the System 4700 spectrometer manufactured by Malvern Instruments, Inc., Framingham, Mass. or Series MM1000 spectrometer manufactured by Amtec, Villeneure-Loubet, France, together with a Coulter Model 1096 correlator.

Figure 4:
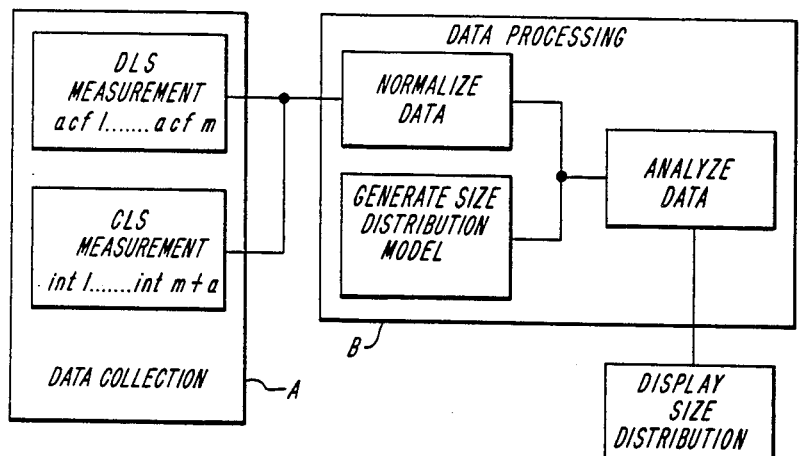
FIG. 4 shows a flow chart illustrating the operation of the system of FIGS. 1 and 2.

FIG. 4 shows a flow chart illustrating the general operation of the system of FIGS. 1 and 2, including a data collection phase, denoted A, and a data processing or analysis phase, denoted B. In accordance with the invention, as shown in FIGS. 1 and 2, the data collection phase A is performed with elements 18 and 28 in two modes. In the first mode, DLS measurements are made an m different angles and the autocorrelator 50 provides m autocorrelation functions, denoted acf 1 . . . acf m in FIG. 4. In the second mode, the CLS measurements are made at the same m angles, where m is an integer greater than or equal to one, and at n additional angles, where n is an integer greater or equal to zero and the integrator 48 provides m+n integrated intensity values, denoted int 1, . . . , int m+n in FIG. 4. These acf and integrated intensity measurements may be made at the same time or sequentially since the resultant data for each measurement is substantially independent. In various forms of the invention, rather than different angles, successive pairs of acf and average intensity measurements can be made at the same angle, but under different conditions, for example, temperature, hydrodynamic solution characteristics, or polarization angles, which establish independent intensity characteristics at the sensor 30. Also, successive pairs of acf and average intensity measurements can be made at various combinations of angles and these conditions.

Figure 5:
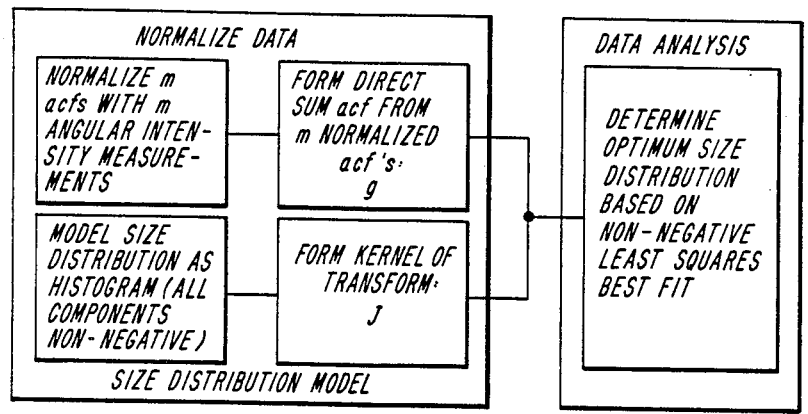
FIGS. 5–7 show detailed flow charts for three implementations of the data processing step of the flow chart of FIG. 4.
Figure 6:
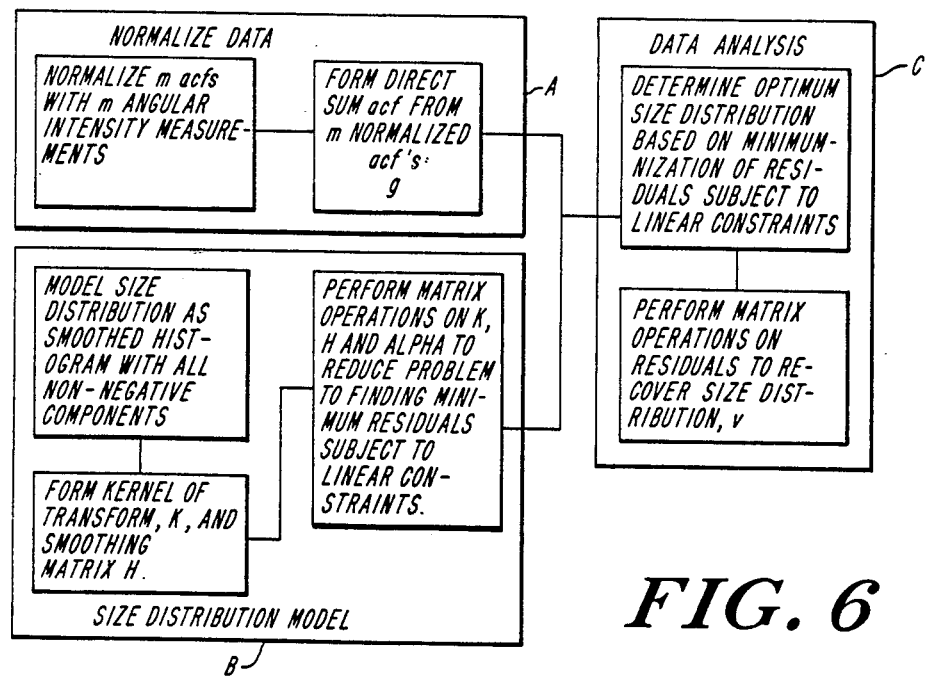
Figure 7:
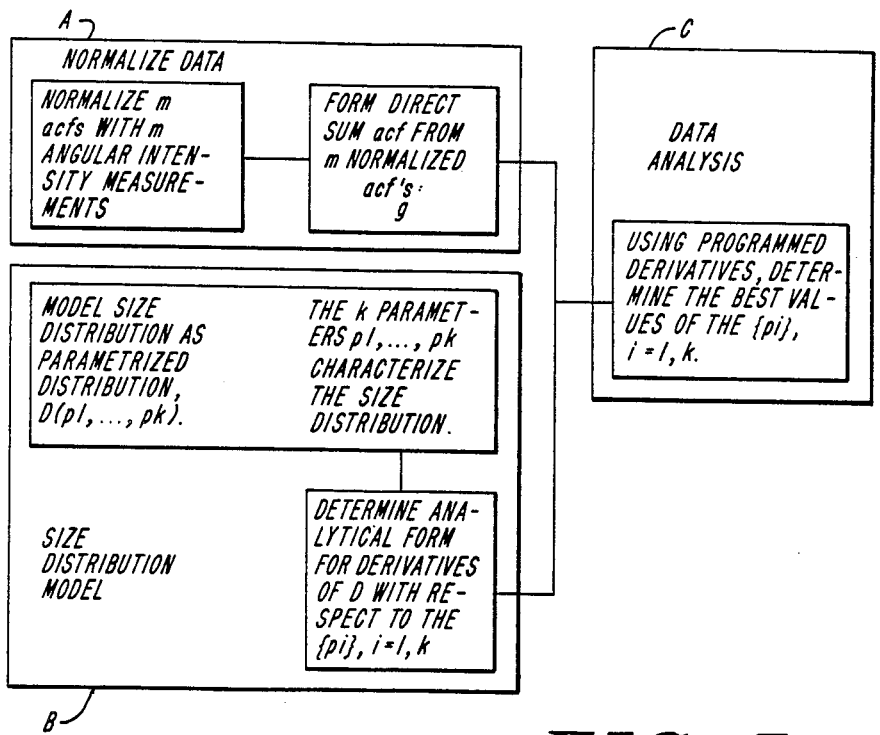

For any of the combinations of angles and conditions at which the CLS and DLS data is measured, FIGS. 5, 6 and 7 illustrate three different signal processing methods which can be implemented by the signal analyzer 52 under the control of controller 54. Each method includes a Normalization Phase, denoted A, and Model Phase, denoted B, and Analysis Phase, denoted C.

In each of the forms of FIGS. 5–7, in the Normalization Phase, the m acf's are first normalized with the angular intensity (CLS) data so that those autocorrelation signals are scaled to the values of the average detected intensities at the m points of detection, forming m normalized acf's. A composite acf is then formed from the direct sum of the m normalized acf's.

In the Model Phase, an analytic, or discrete, model is constructed for use in the Analysis Phase so that the inversion of the equation $$v = J^{-1}(g_1(t), \ldots, g_m(t), i(\theta_1), \ldots, i(\theta_m), i(\theta_{m+1}), \ldots, i(\theta_{m+n}))$$

may be performed. Each of FIGS. 5, 6 and 7 indicates a different exemplary and known form for constructing the model in a conventional manner for ill-conditioned functions.

In FIG. 5, a model size distribution is generated as a histogram having all non-negative components and a kernel J is formed for the transform. To find the size distribution v(r) using this kernel, a programmed digital computer using Non-Negative Least Squares (NNLS) techniques performs a "best fit", see C. Lawson and R. Hanson, "Solving Least Square Problems", Prentice Hall, Inc., Englewood Cliffs, N.J., 1974.

In FIG. 6, a model size distribution is generated as a smoothed histogram with all non-negative components. A kernel J and a smoothing martrix H are formed and a characteristic alpha ($\alpha$) is generated. Then matrix operations are performed on J, H and alpha to reduce the problem to determining the residual vector having the minimum norm subject to linear constraints. To find the size distribution v(r) using J, H and alpha, a programmed digital computer using Least Distance Programming techniques, minimizes the norm of the residuals, $[J_iv]_j - g_i(t_j)$, subject to linear constraints, and matrix operations are then performed to determine v(r); see C. Lawson and R. Hanson, "Solving Least Square Problems", Prentice Hall, Inc., Englewood Cliffs, N.J., 1974.

In FIG. 7, the model size distribution is determined in terms of a parameterized distribution D(p1, p2, . . . pk), where the parameters p1, p2 . . . pk determine the size distribution. Then an analytical form is determined for derivatives of D with respect to the $\{P_i\}$, i=1, . . . K. A programmed digital computer uses Non-Linear Least Squares fitting techniques to determine the best values of the {Pi} characterizing v(r) using the program GRADLS; see P. R. Bevington, "Data Reduction and Error Analysis for the Physical Sciences", McGraw Hill Book Co., New York, 1969.

In all of the forms of the invention shown in FIGS. 5–7, the acf's are normalized and then a composite acf is formed. However, in alternate forms of the invention, the acf's may be unity normalized and then used to form the composite acf. Then the kernel J may be normalized and the normalized transformation operator may be used to generate the size distribution. Moreover, the composite acf's in FIGS. 5 and 6 are direct sums of the normalized acf's (and the CLS intensities), where linear transforms are used. In other forms of the inventions, as in FIG. 7, non-linear transforms are used.

Additionally, as described above, the scattered light for the sample is measured alone, forming the basis for a homodyne analysis. Alternatively, the measurement may be made on the scattered light as augmented by non-scattered light from the source, so that a beat signal is in effect produced as the basis for a heterodyne analysis. In those forms, the signals g(t) may be the true autocorrelation of the detected intensity, or may be merely "closely related", for example, where a background level is subtracted out and the square root of the resultant signal is taken. The latter is particularly appropriate for gaussian light in a homodyne configuration.

In the preferred embodiment of FIGS. 1 and 2, the light source 18, detector 28 (including elements 44, 46 and 48) and the autocorrelator 50 are provided by a Langley Ford Model LSA2+ photon correlation spectrometer and a Langley Ford Model 1096 correlator. The signal analyzer 52 and controller 54 are in the form of a Model Universe 137/T digital computer manufactured by Charles River Data Systems, Natick, Mass., having a UNOS operating system with a Fortran 77 Compiler, as produced by Absoft Corporation, Royal Oak, Mich., programmed in accordance with the program set forth in Appendix B. With this configuration, acf and CLS data is collected at two angles, for example, 90° and 30°. As the, data is collected, it is automatically stored in the internal memory of the 1096 correlator. After the data at two angles has been collected and stored, the data is transferred to the 137/T computer through a serial (RS-232) port. The 1096 correlator is set to send the data in its 'five channels per line' format. The data, received through the RS-232 port, is directly stored to a disk file on the 137/T computer.

The format of the data from the 1096 correlator, as stored in the 137/T computer disk file, is changed into the correct format for the signal processing program, cont2ang.fm, included in Appendix B. This format conversion is accomplished by processing the two data sets (one for each angle) using the 137/T computer programmed in accordance with the program condense.fm shown in Appendix C. Under control of the program, condense.fm, the 137/T computer reads the acf data along with the sample times used in the measurements (also contained in the data sets from the 1096 correlator) and condenses the 256 channels of data for each angle into two sets of 60 channels of data, by combining several channels of the original data into one channel of condensed data. The processed data is written out to a new disk file on the 137/T computer. This process of condensing the data is done only to speed the subsequent data processing, it has no material affect on the sizing results obtained. Under the control of the condense.fm program, the 137/T computer then writes out the 60 acf time points for the first angle, corresponding to the 60 condensed acf points at which the data is measured. The data is written out in the FORTRAN format 5e15.6. Following the acf time points for the first angle are written out the 60 acf time points for the second angle in the same format. This is followed by the 60 condensed acf points for the first angle and then the 60 condensed acf points for the second angle. The acf points are written out in the FORTRAN format 4e17.11.

At this point, a new disk file contains reformatted and condensed data equivalent to the original data collected by the 1096 correlator. This new data file, which contains only time points and acf points for the two angles, is prefixed by a header which informs the signal processing program cont2ang.fm how the data should be handled and gives the program some other information, such as the temperature and viscosities of the sample, the scattering angles, and the like. The contents of the header are described in the first page of the listing in Appendix B and in CONTIN Users Manual, Postfach 10.2209,D-6900 Heidelberg, BRD. For illustrative purposes, a sample header is included in Appendix D. The header is prefixed to the file using the 137/T computer editor, ted.

Figures 8, 9:
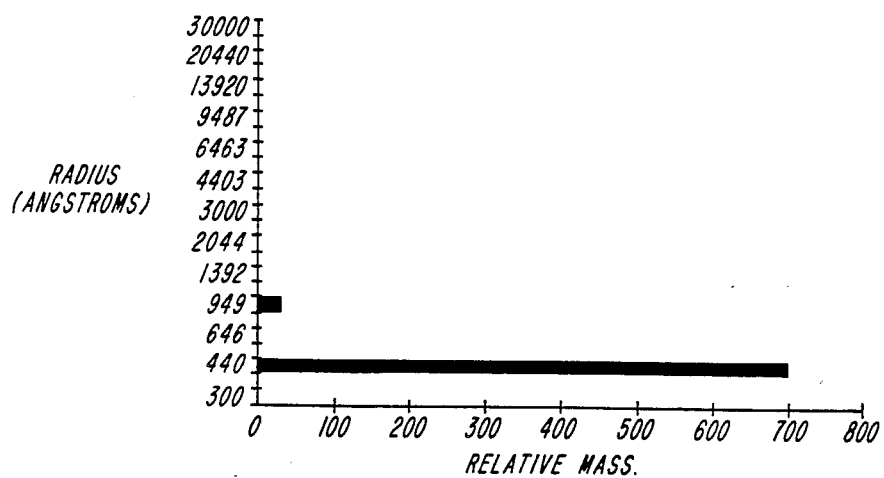
FIGS. 8 and 9 illustrate the mass weighted size distribution determined by an embodiment of the present invention for an exemplary sample of polystyrene latex spheres dispersed in water.

Once the header is prefixed to the data file containing the condensed two angle data, cont2ang.fm is called to process the data and provide the size distribution of the particles contained in the sample. FIGS. 8 and 9 shows the mass weighted size distribution, v(r) generated with this configuration where the sample comprised a mixture of 450 A and 850 A (radius) polystyrene latex spheres (from Seragen Diagnostics) dispersed in water. The measurements were made at scattering angles of 144° (300 second measurement) and 63.2° (900 second measurement) at a temperature of 20° C. FIG. 8 shows a portion of the data output from the cont2ang.fm program for this example, and FIG. 9 shows a graph representative of this data.

The larger sized particles in this sample are less than twice as large as the smaller ones; for light scattering measurements, such relatively closely space peaks are extremely difficult to resolve. The enhanced resolution resulting from combining DLS and CLS data allows clear separation of the two peaks, as shown in FIG. 9.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

APPENDIX B

```
C     CONT2ANG.FM
C
C        RUSER
C        10       TEMPERATURE (DEG C)
C        11       SAMPLE VISCOSITY (CP)
C        12       SCATTERING ANGLE (DEGREES)
C        13       INCIDENT WAVELENGTH (A)
```

```
C     14         REFRACTIVE INDEX OF SAMPLE
C     15         BACKGROUND TO SUBTRACT (1ST Q)
C     16         BACKGROUND TO SUBTRACT (2ND Q)
C     17         2ND SCATTERING ANGLE (DEGREES)
C     18         RELATIVE AMPLITUDE CORRECTION FOR Q1/Q2
C     20         Q1 (NOT INPUT; USED INTERNALLY)
C     21         Q2 (NOT INPUT; USED INTERNALLY)
C     22         1/ACF(1) (NOT INPUT; USED INTERNALLY)
C     23         1/(ACF(ISTART)*SQRT(RUSER(18)) (NOT INPUT; USED INTERNALLY)
C     24         I1/(I1+I2) ; (I = TOTAL SCATTERED INTENSITY)
C     25         WEIGHTING FACTOR (1/VAR) FOR 1ST ANGLE (LUSER(12,14)=TRUE)
C     26         WEIGHTING FACTOR (1/VAR) FOR 2ND ANGLE (LUSER(12)=TRUE)
C
C     LUSER
C     11         T IF DATA AT TWO Q'S IS TO BE ANALYZED
C     12         T (WITH 13 F) WITH 2ANG DATA, WEIGHTS 2ND ANGLE TO RUSER(26)
C     13         T TO INCLUDE VOLUME (R**3) IN KERNEL
C     14         T (WITH 12 T) WITH 2ANG DATA, WEIGHTS 1ST ANGLE TO RUSER(25)
C     15         T TO INCLUDE FORM FACTOR IN KERNAL WITH SINGLE ANGLE DATA
C     16         T IF SQUARE ROOT OF ACF IS NOT TO BE TAKEN
C     17         T TO EXCLUDE FORM FACTOR IN KERNEL WITH 12 OR 12 AND 14 TRUE
C     18         T IF ACF'S ARE NOT TO BE NORMALIZED (TOTAL INTENSITIES
C                    MUST BE ACCURATELY MEASURED AND COMPENSATED IN RUSER(18)).
C     19         T IF MIE INTENSITY CORRECTION IS TO BE USED. (TAKES SPECIAL
C                    USERK
C     20         T IF MIE INTENSITY IS TO BE IGNORED IN TWO ANGLE FITS.
C
C
C     IUSER
C     11         NUMBER OF FIRST DATA POINT OF 2ND Q (USED ONLY IF LUSER(11)=T)
C     12         NUMBER OF DATA POINTS TO USE TO EXTRPOLATE TO ACF(0)
C
      DOUBLE PRECISION PRECIS, RANGE                                    MAIN  5
      DOUBLE PRECISION A, AA, AEQ, AINEQ, PIVOT, REG, RHSNEQ,           MAIN  6
     1 S, SOLBES, SOLUTN, VALPCV, VALPHA, VK1Y1, WORK                   MAIN  7
      LOGICAL DOMOM, DOUSIN, DOUSNQ, DOUSOU, LAST, NONNEG, ONLY1, PRWT, MAIN  8
     + PRY, SIMULA, LUSER                                               MAIN  9
      LOGICAL LBIND                                                     MAIN  0
      DIMENSION T(544), SQRTW(544), Y(544), EXACT(544), YLYFIT(544)     MAIN  1
      DIMENSION G(44), CQUAD(44), VK1Y1(44), S(44,3), VALPHA(44),       MAIN  2
     + VALPCV(44), SOLUTN(44), IISIGN(44), SOLBES(44), SOLPK(44),       MAIN  3
     + AA(44,44)                                                        MAIN  4
      DIMENSION AINEQ(42,44), RHSNEQ(42), LBIND(42)                     MAIN  5
      DIMENSION A(44,44), IWORK(44)                                     MAIN  6
      DIMENSION REG(42,44)                                              MAIN  7
      DIMENSION AEQ(11,44), PIVOT(11)                                   MAIN  8
      DIMENSION WORK(1976)                                              MAIN  9
      DIMENSION LSDONE(90,3,2), VDONE(90)                               MAIN  0
C
C     THE FOLLOWING DIMENSION STATEMENT IS TO ALLOW MIE INTENSITY CORRECTIONS.
C     (LUSER(19) SHOULD BE SET TRUE FOR MIE CORRECTIONS AND THE MIE KERNEL
C     ADDITION TO THE PROGRAM MUST BE IN PLACE. WHEN OTHER INTENSITY
C     CORRECTIONS ARE EMPLOYED, A DIFFERENT USERK MUST BE INSERTED IN THIS
C     PROGRAM, BUT THE REVISIONS IN THIS ROUTINE NEED NOT BE CHANGED.
      REAL MIEINT(50,2), MIE
C
      CHARACTER IFORMT(70), IFORMW(70), IFORMY(70),LA(6,46),ITITLE(80)
      COMMON /SBLOCK/ PRECIS, RANGE, SRMIN,                             MAIN  6
     1 ALPST(2), GMNMX(2), PLEVEL(2,2), RSVMNX(2,2), RUSER(100),        MAIN  7
     + EXMAX, SRANGE                                                    MAIN  8
      COMMON /IBLOCK/ IGRID, IPLRES, IPRINT, IQUAD, IUNIT, IWT,         MAIN  9
     + LINEPG, MIOERR, MQPITR, NEQ, NERFIT, NG, NINTT, NLINF, NORDER,   MAIN  0
     + ICRIT(2), IPLFIT(2),                                             MAIN  1
     +           IUSER(50), LSIGN(4,4), MOMMMX(2), NENDZ(2),            MAIN  2
     + NFLAT(4,2), NGL, NGLP1, NIN, NINEQ, NNSGN(2), NOUT, NQPROG(2),   MAIN  3
     + NSGN(4), NY                                                      MAIN  4
      COMMON /CBLOCK/ IFORMT,IFORMW,IFORMY, LA,ITITLE
      COMMON /LBLOCK/ DOMOM, DOUSIN, DOUSNQ, DOUSOU, LAST, NONNEG,      MAIN  5
     1 ONLY1, PRWT, PRY, SIMULA,                                        MAIN  6
     + LUSER(30)                                                        MAIN  7
C
C     THE FOLLOWING LABELLED COMMON WAS ADDED TO AVOID THE NECESSITY OF
C     CONSTANTLY RECOMPUTING THE KERNAL. THE COMMON BLOCK IS ALSO IN
C     GETROW. ASSOCIATED WITH THIS ADDITION IS A SMALL ADDED SECTION IN
```

```
C     THIS ROUTINE AND ONE LINE CHANGED IN GETROW.
C     THESE CHANGES ARE MARKED IN THE SOURCE CODE.
C
      COMMON /KERNAL/ USERKK(544,35)
      DATA MY/544/, MA/44/, MG/44/, MREG/42/, MINEQ/42/, MEQ/11/,         MAIN 4
     1 MDONE/90/, MWORK/1976/                                             MAIN 5
      CALL INIT                                                           MAIN 6
  100 CALL INPUT (EXACT,G,MA,MEQ,MG,MINEQ,MREG,MWORK,MY,                  MAIN 0
     +  SQRTW,T,Y)
      CALL SETGRD (CQUAD,G,GMNMX,IGRID,IQUAD,MG,NG,NOUT)                  MAIN 4
C
C     THE FOLLOWING SECTION WAS ADDED TO STORE THE KERNAL MATRIX SO THAT
C     IT NEED NOT BE CONSTANTLY RECOMPUTED. THE LABELLED COMMON IN THIS
C     ROUTINE AND IN GETROW STORE THE VALUES, ONE LINE IN GETROW IS
C     CHANGED TO USE THE STORED VALUES.
C
C     THE SECTION HAS BEEN MODIFIED TO ALLOW MIE CORRECTIONS WITHOUT
C     TAKING UNDUE AMOUNTS OF TIME. 10-23-85.
C
      IF(LUSER(19)) THEN
         DO 19 JG=1,NG
            MIEINT(JG,1)=MIE(G(JG),RUSER,12)
            MIEINT(JG,2)=MIE(G(JG),RUSER,17)
            IF(LUSER(13)) THEN
               WGHCOR=G(JG)*G(JG)*G(JG)
               MIEINT(JG,1)=MIEINT(JG,1)/WGHCOR
               MIEINT(JG,2)=MIEINT(JG,2)/WGHCOR
            ENDIF
   19    CONTINUE
         BIGG=0.
         DO 18 JG=1,NG
         DO 18 JJ=1,2
            IF(MIEINT(JG,JJ).GT.BIGG) BIGG=MIEINT(JG,JJ)
   18    CONTINUE
         DO 17 JG=1,NG
         DO 17 JJ=1,2
            MIEINT(JG,JJ)=MIEINT(JG,JJ)/BIGG
   17    CONTINUE
         OPEN(3,FILE='mieang1',STATUS='new')
         OPEN(4,FILE='mieang2',STATUS='new')
         WRITE(3,*) NG
         WRITE(3,511) (G(JG)/5.,MIEINT(JG,1),JG=1,NG)
         WRITE(4,*) NG
         WRITE(4,511) (G(JG)/5.,MIEINT(JG,2),JG=1,NG)
  511    FORMAT(E10.3,1x,E10.3)
         CLOSE(3)
         CLOSE(4)
         DO 20 JT=1,NY
         DO 20 JG=1,NG
            IF(.NOT.LUSER(20)) THEN
               IF(JT.LT.IUSER(11))USERKK(JT,JG)=USERK(JT,T,JG,G)*
     +                           MIEINT(JG,1)
               IF(JT.GE.IUSER(11))USERKK(JT,JG)=USERK(JT,T,JG,G)*
     +                           MIEINT(JG,2)
            ELSE
               IF(JT.LT.IUSER(11))USERKK(JT,JG)=USERK(JT,T,JG,G)
               IF(JT.GE.IUSER(11))USERKK(JT,JG)=USERK(JT,T,JG,G)
            ENDIF
C           IF(JT.LT.IUSER(11) .AND. .NOT.LUSER(18))
C     +                           USERKK(JT,JG)=USERKK(JT,JG)*RUSER(22)
C           IF(JT.GE.IUSER(11) .AND. .NOT.LUSER(18))
C     +                           USERKK(JT,JG)=USERKK(JT,JG)*RUSER(23)
   20    CONTINUE
      ELSE
         DO 21 JT=1,NY
         DO 21 JG=1,NG
            USERKK(JT,JG)=USERK(JT,T,JG,G)
   21    CONTINUE
      ENDIF
C
C     END OF ADDED LINES
C
      IF (SIMULA)  CALL USERSI (EXACT,MY,T,Y)                             MAIN 8
```

```
      IF (SIMULA) CALL WRITYT (EXACT,G,IPRINT,IWT,MG,NOUT,NY, PRY,     MAIN 2
     +SIMULA,SQRTW,T,Y)                                                 MAIN 3
      IF (.NOT.ONLY1) CALL USERSX (EXACT,G,MG)                          MAIN 7
      NINEQ=0                                                           MAIN 8
      NGL=NG+NLINF                                                      MAIN 9
      NGLP1=NGL+1                                                       MAIN 0
      IF (DOUSNQ) CALL USERNQ (AINEQ,MG,MINEQ)                          MAIN 4
      IF (NONNEG) CALL SETNNG (AINEQ,MINEQ,NG,NGLP1,NINEQ)              MAIN 8
      IF (IWT.EQ.1 .OR. IWT.EQ.4) GO TO 200                             MAIN 9
      CALL ANALYZ (1,                                                   MAIN 5
     + A,AA,AEQ,AINEQ,CQUAD,EXACT,G,IISIGN,IWORK,LBIND,LSDONE,MA,       MAIN 6
     + MDONE,MEQ,MG,MINEQ,MREG,MWORK,MY,PIVOT,REG,RHSNEQ,S,SOLBES,      MAIN 7
     + SOLPK,SOLUTN,SQRTW,T,VALPCV,VALPHA,VDONE,VK1Y1,WORK,             MAIN 8
     4 Y,YLYFIT)                                                        MAIN 9
      CALL SETWT (                                                      MAIN 3
     1 CQUAD,G,IUNIT,IWT,MWORK,MY,NERFIT,NG,NGL,NLINF,NOUT,NY,PRWT,     MAIN 4
     2 SOLBES,SQRTW,SRANGE,T,WORK,Y,YLYFIT)                             MAIN 5
  200 CALL ANALYZ (2,                                                   MAIN 9
     1 A,AA,AEQ,AINEQ,CQUAD,EXACT,G,IISIGN,IWORK,LBIND,LSDONE,MA,       MAIN 0
     2 MDONE,MEQ,MG,MINEQ,MREG,MWORK,MY,PIVOT,REG,RHSNEQ,S,SOLBES,      MAIN 1
     3 SOLPK,SOLUTN,SQRTW,T,VALPCV,VALPHA,VDONE,VK1Y1,WORK,             MAIN 2
     4 Y,YLYFIT)                                                        MAIN 3
      IF (.NOT.LAST) GO TO 100                                          MAIN 4
      STOP                                                              MAIN 5
      END                                                               MAIN 6
      BLOCK DATA                                                        BLCKD3
      DOUBLE PRECISION PRECIS, RANGE                                    BLCKD4
      CHARACTER IFORMT(70), IFORMW(70), IFORMY(70),LA(6,46),ITITLE(80)
      LOGICAL DOMOM, DOUSIN, DOUSNQ, DOUSOU, LAST, NONNEG, ONLY1, PRWT, BLCKD5
     1 PRY, SIMULA, LUSER                                               BLCKD6
      COMMON /SBLOCK/ PRECIS, RANGE, SRMIN,                             BLCKD7
     1 ALPST(2), GMNMX(2), PLEVEL(2,2), RSVMNX(2,2), RUSER(100),        BLCKD8
     2 EXMAX, SRANGE                                                    BLCKD9
      COMMON /IBLOCK/ IGRID, IPLRES, IPRINT, IQUAD, IUNIT, IWT,         BLCKD0
     1 LINEPG, MIDERR, MQPITR, NEQ, NERFIT, NG, NINTT, NLINF, NORDER,   BLCKD1
     2 ICRIT(2), IPLFIT(2),                                             BLDKD2
     3          IUSER(50), LSIGN(4,4), MOMNMX(2), NENDZ(2),             BLCKD3
     4 NFLAT(4,2), NGL, NGLP1, NIN, NINEQ, NNSGN(2), NOUT, NQPROG(2),   BLCKD4
     5 NSGN(4), NY                                                      BLCKD5
      COMMON /CBLOCK/ IFORMT, IFORMW, IFORMY, LA,ITITLE
      COMMON /LBLOCK/ DOMOM, DOUSIN, DOUSNQ, DOUSOU, LAST, NONNEG,      BLCKD6
     1 ONLY1, PRWT, PRY, SIMULA,                                        BLCKD7
     2 LUSER(30)                                                        BLCKD8
      DATA RANGE/1.D250/, SRANGE/1.E35/, NIN/5/, NOUT/9/                BLCKD4
      DATA ALPST/2*0./, GMNMX/1., 100./, PLEVEL/4*.5/,                  BLCKD5
     1 RSVMNX/2*1., 1.E3, 1.E-3/, RUSER/100*0./, SRMIN/.01/             BLCKD6
      DATA ICRIT/2*1/,                                                  BLCKD7
     1 IFORMT/'(','5','E','1','5','.','6',')',62*' '/,                  BLCKD8
     2 IFORMW/'(','5','E','1','5','.','6',')',62*' '/,                  BLCKD9
     3 IFORMY/'(','5','E','1','5','.','6',')',62*' '/,                  BLCKD0
     4 IGRID/2/, IPLFIT/2*2/, IPLRES/2/, IPRINT/3/, IQUAD/3/, IUNIT/-1/,BLCKD1
     5 IUSER/50*0/, IWT/1/, LINEPG/60/,                                 BLCKD2
     6 LSIGN/16*0/, MIDERR/5/, MOMNMX/-1, 3/, MQPITR/35/,               BLCKD3
     7 NENDZ/1, 1/, NEQ/0/, NERFIT/10/, NFLAT/8*0/, NG/35/,             BLCKD4
     8 NINTT/1/, NLINF/0/, NNSGN/2*0/, NORDER/2/, NQPROG/19, 0/,        BLCKD5
     9 NSGN/4*0/                                                        BLCKD6
      DATA DOMOM/.TRUE./, DOUSIN/.FALSE./, DOUSNQ/.TRUE./,              BLCKD7
     1 DOUSOU/.FALSE./, LAST/.TRUE./,                                   BLCKD8
     2 LUSER/30*.FALSE./, NONNEG/.TRUE./, ONLY1/.TRUE./,                BLCKD9
     3 PRWT/.TRUE./, PRY/.TRUE./,                                       BLCKD0
     4 SIMULA/.FALSE./                                                  BLCKD1
      END                                                               BLCKD4
      SUBROUTINE ANALYZ (ISTAGE,                                        ANLYZ3
     1 A,AA,AEQ,AINEQ,CQUAD,EXACT,G,IISIGN,IWORK,LBIND,LSDONE,MA,       ANLYZ4
     2 MDONE,MEQ,MG,MINEQ,MREG,MWORK,MY,PIVOT,REG,RHSNEQ,S,SOLBES,      ANLYZ5
     3 SOLPK,SOLUTN,SQRTW,T,VALPCV,VALPHA,VDONE,VK1Y1,WORK,             ANLYZ6
     4 Y,YLYFIT)                                                        ANLYZ7
      DOUBLE PRECISION PRECIS, RANGE                                    ANLYZ8
      DOUBLE PRECISION A, AA, ABS, AEQ, AINEQ, ALPBES, ALPHA,           ANLYZ9
     1 ALPOLD, ONE, PIVOT, RALPFL, REG, RHSNEQ, VK1Y1, WORK, ZERO       ANLYZ0
     2 S, SOLBES, SOLUTN, VALPCV, VALPHA, VK1Y1, WORK, ZERO             ANLYZ1
      DOUBLE PRECISION SOL1(44),ACDIFF(544),SOLDIF(44),DDDUM,KERROW(44)
      LOGICAL FSTSOL
```

```
      LOGICAL DOMOM, DOUSIN, DOUSNQ, DOUSOU, LAST, NONNEG, ONLY1, PRWT,     ANLYZ2
     1 PRY, SIMULA, LUSER                                                    ANLYZ3
      LOGICAL LDUM, LBIND, FLAT, FPLTFR, HEADNG, NEWPAG                      ANLYZ4
      CHARACTER IFORMT(70), IFORMW(70), IFORMY(70),LA(6,46), ITITLE(80)
      DIMENSION A(MA,MG), T(MY), Y(MY), SQRTW(MY), G(MG), CQUAD(MG),         ANLYZ5
     1 REG(MREG,MG), AEQ(MEQ,MG), PIVOT(MEQ), VK1Y1(MG), S(MG,3),            ANLYZ6
     2 AINEQ(MINEQ,MG), VALPHA(MG), VALFCV(MG), RHSNEQ(MINEQ),               ANLYZ7
     3 WORK(MWORK), IWORK(MA), EXACT(MG), SOLUTN(MG), LBIND(MINEQ),          ANLYZ8
     4 IISIGN(MG), SOLBES(MG), LSDONE(MDONE,3,2), VDONE(MDONE),              ANLYZ9
     5 SOLPK(MG), YLYFIT(MY), AA(MG,MG)                                      ANLYZ0
      DIMENSION PREJ(2), LLSIGN(5), SAVBES(7)
      CHARACTER IHOLER(6)
      COMMON /SBLOCK/ PRECIS, RANGE, SRMIN,                                  ANLYZ2
     1 ALPST(2), GMNMX(2), PLEVEL(2,2), RSVMNX(2,2), RUSER(100),             ANLYZ3
     2 EXMAX, SRANGE                                                         ANLYZ4
      COMMON /IBLOCK/ IGRID, IPLRES, IPRINT, IQUAD, IUNIT, IWT,              ANLYZ5
     1 LINEPG, MIOERR, MQPITR, NEQ, NERFIT, NG, NINTT, NLINF, NORDER,        ANLYZ6
     2 ICRIT(2), IPLFIT(2),
     3             IUSER(50), LSIGN(4,4), MOMNMX(2), NENDZ(2),               ANLYZ8
     4 NFLAT(4,2), NGL, NGLP1, NIN, NINEQ, NNSGN(2), NOUT, NQPROG(2),        ANLYZ9
     5 NSGN(4), NY                                                           ANLYZ0
      COMMON /CBLOCK/ IFORMT, IFORMW, IFORMY,LA, ITITLE
      COMMON /LBLOCK/ DOMOM, DOUSIN, DOUSNQ, DOUSOU, LAST, NONNEG,           ANLYZ1
     1 ONLY1, PRWT, PRY, SIMULA,                                             ANLYZ2
     2 LUSER(30)                                                             ANLYZ3
      DATA IHOLER/'A','N','A','L','Y','Z'/, RALPHA/1./                       ANLYZ4
      ABS(ALPHA)=DABS(ALPHA)                                                 ANLYZ5
      SINGLE(ONE)=SNGL(ONE)                                                  ANLYZ6
      ZERO=0.D0                                                              ANLYZ9
      ONE=1.D0                                                               ANLYZ1
      CALL SEQACC (                                                          ANLYZ6
     1 A,CQUAD,G,ISTAGE,IUNIT,IWT,MA,MG,NG,NGL,NGLP1,NLINF,NY,               ANLYZ7
     2 RANGE,SQRTW,T,Y)                                                      ANLYZ8
      NGLY=MIN0(NGL,NY)                                                      ANLYZ9
      NGLE=NGL-NEQ                                                           ANLYZ0
      CALL SETREG (MG,MREG,NENDZ,NG,NGL,NGLE,NGLP1,NORDER,                   ANLYZ4
     1 NOUT,NREG,PRECIS,REG)                                                 ANLYZ5

IF (NEQ .GT. 0)  CALL USEREQ (AEQ,CQUAD,MEQ,MG)                        ANLYZ2
      CALL ELIMEQ (AEQ,MEQ,MG,PIVOT,NEQ,NGL,A,MA,REG,MREG,NREG,NGLP1,        ANLYZ3
     1 NGLY,VK1Y1,RANGE)                                                     ANLYZ4
      IF (NORDER.EQ.0 .AND. NEQ.EQ.0)  GO TO 300                             ANLYZ5
      CALL SVDRS2 (REG(1,NEQ+1),MREG,NREG,NGLE,REG(1,NGLP1),MREG,            ANLYZ9
     1 1,S,IERROR,RANGE)                                                     ANLYZ0
      IF (IERROR .NE. 1)  CALL ERRMES (1,.TRUE.,IHOLER,NOUT)                 ANLYZ1
      CALL DIAREG (A,AEQ,MA,MEQ,MG,MREG,NEQ,NGL,NGLE,NGLY,NOUT,PIVOT,        ANLYZ2
     1 RANGE,REG,S)                                                          ANLYZ3
  300 CALL SVDRS2 (A,MA,NGLY,NGLE,A(1,NGLP1),MA,1,S,IERROR,RANGE)            ANLYZ8
      IF (IERROR .NE. 1)  CALL ERRMES (2,.TRUE.,IHOLER,NOUT)                 ANLYZ9
      CALL DIAGA (A,MA,MG,MREG,NEQ,NGL,NGLE,NGLP1,NGLY,REG,S)                ANLYZ0
      DO 320 J=1,NGLE                                                        ANLYZ1
        YLYFIT(J)=S(J,1)                                                     ANLYZ2
  320 CONTINUE                                                               ANLYZ3
 5320 FORMAT (//30X,'SINGULAR VALUES'//(1P10E13.3))                          ANLYZ4
      WRITE (NOUT,5320) (YLYFIT(J),J=1,NGLE)                                 ANLYZ5
      IF (NINEQ .GT. 0)  CALL SETGA1 (NINEQ, A,AINEQ,MA,MG,MINEQ,MREG,       ANLYZ9
     1NGL,NGLE,REG)                                                          ANLYZ0
      IF (MAX0(NQPROG(1),NQPROG(2)).LE.0 .AND. ALPST(ISTAGE).LE.0.)          ANLYZ1
     1 CALL ERRMES (3,.TRUE.,IHOLER,NOUT)                                    ANLYZ2
      BTEST=SRANGE                                                           ANLYZ3
      ALPBES=ZERO                                                            ANLYZ4
      VARZ=SRANGE                                                            ANLYZ5
      LDUM=.TRUE.                                                            ANLYZ9
      DO 410 ICOL=1,2                                                        ANLYZ0
        IF (ALPST(ISTAGE).LE.0. .OR. ICOL.EQ.1)  GO TO 412                   ANLYZ1
        K=1                                                                  ANLYZ2
        ALPHA=ALPST(ISTAGE)                                                  ANLYZ3
        BTEST=SRANGE                                                         ANLYZ4
        GO TO 425                                                            ANLYZ5
  412   IF (NQPROG(ICOL)-1)  410,420,415                                     ANLYZ6
  415   RTOT=RSVMNX(2,ICOL)/(RSVMNX(1,ICOL)*PRECIS)                          ANLYZ7
        IF (RTOT .LE. 1.)  CALL ERRMES (4,.TRUE.,IHOLER,NOUT)                ANLYZ8
        RALPHA=RTOT**(1./FLOAT(NQPROG(ICOL)-1))                              ANLYZ9
```

```
      420  ALPHA=RSVMNX(1,ICOL)*PRECIS*S(1,1)                                   ANLYZ0
           K=NQPROG(ICOL)                                                       ANLYZ1
           FSTSOL=.TRUE.
      425  DO 430 J=1,K                                                         ANLYZ2
               CALL SETVAL (ALPHA,LDUM,NINEQ,                                   ANLYZ3
         1     A,AINEQ,MA,MG,MINEQ,MREG,NGL,NGLE,REG,RHSNEQ,S,VALPCV,VALPHA,    ANLYZ4
         2     VK1Y1)                                                           ANLYZ5
               NEWPAG=IABS(IPRINT).GE.3 .OR. (ISTAGE.EQ.2 .AND.                 ANLYZ6
         1     IPRINT.GT.0) .OR. LDUM                                           ANLYZ7
               PPLTPR=IABS(IPRINT).GE.2 .OR. ISTAGE.EQ.2                        ANLYZ8
               HEADNG=PPLTPR .OR. LDUM                                          ANLYZ9
               CALL LDPETC (.TRUE.,NINEQ,.TRUE.,ICRIT(ISTAGE),DOMOM,PPLTPR,     ANLYZ0
         1     .TRUE.,ALPHA,HEADNG,NEWPAG,ALPBES,VAR,                           ANLYZ1
         2     A,AA,AINEQ,BTEST,CQUAD,DEGFRE,DEGFRZ,EXACT,G,IERROR,             ANLYZ2
         3     ISTAGE,IWORK,LBIND,MA,MG,MINEQ,MREG,MWORK,MY,                    ANLYZ3
         4     NGLE,NGLY,PREJ,REG,RHSNEQ,S,SAVBES,SOLBES,                       ANLYZ4
         5     SOLUTN,SQRTW,T,VALPCV,VALPHA,VARREG,VARZ,WORK,Y,YLYFIT)          ANLYZ5
           IF (IERROR.NE.1) GO TO 980
           IF(.NOT.FSTSOL) GO TO 910
           DO 900 KK=1,NG
      900  SOL1(KK)=SOLUTN(KK)
           FSTSOL=.FALSE.
      910  CONTINUE
           DO 920 KK=1,NG
      920  SOLDIF(KK)=SOLUTN(KK)-SOL1(KK)
    C      WRITE(NOUT,950) (SOL1(KK),SOLUTN(KK),SOLDIF(KK),KK=1,NG)
    C 950  FORMAT('1ST ',E12.6,' CURRENT ',E12.6,' DIFF ',E12.6)
           DO 915 KK=1,NY
               CALL GETROW (KK,KERROW,.FALSE.,0,1,IUNIT,                        GEYLY5
         1     SQRTW,NY,NGL,IWT,NG,CQUAD,G,T,NLINF,Y)                           GEYLY6
           DDDUM=0D0
           DO 916 KL=1,NG
      916  DDDUM=DDDUM+SOLDIF(KL)*KERROW(KL)
           ACDIFF(KK)=DDDUM
      915  CONTINUE
           DDDUM=0D0
           DO 930 KK=1,NY
      930  DDDUM=DDDUM+ACDIFF(KK)*ACDIFF(KK)
           WRITE(NOUT,940)NG,NY,DDDUM
      940  FORMAT(1X,'NG=',I5,' NY=',I5,
         1  '&&&&&&&&&&&&&&&&SUM OF SQUARES OF DIFFERENCE SOLUTION=',E15.8)
      980  CONTINUE
               IF (IERROR.EQ.1 .AND. PPLTPR) CALL RUNRES (3,SOLUTN,.FALSE.,     ANLYZ6
         1     SINGLE(ALPHA/S(1,1)), CQUAD,G,IPLFIT,IPLRES,ISTAGE,ITITLE,IUNIT, ANLYZ7
         2     IWT,LINEPG,MWORK,NG, NGL,NLINF,NOUT,NY,SQRTW,SRANGE,T,WORK,Y,    ANLYZ8
         3     YLYFIT)                                                          ANLYZ9
               ALPHA=ALPHA*RALPHA                                               ANLYZ0
               LDUM=.FALSE.                                                     ANLYZ1
      430  CONTINUE                                                             ANLYZ2
      410 CONTINUE                                                              ANLYZ3
           IF (BTEST .GE. SRANGE) CALL ERRMES (5,.TRUE.,IHOLER,NOUT)            ANLYZ4
           CALL RUNRES (2,SOLBES,.TRUE.,SINGLE(ALPBES/S(1,1)),                  ANLYZ5
         1 CQUAD,G,IPLFIT,IPLRES,ISTAGE,ITITLE,IUNIT,IWT,LINEPG,MWORK,NG,       ANLYZ6
         2 NGL,NLINF,NOUT,NY,SQRTW,SRANGE,T,WORK,Y,YLYFIT)                      ANLYZ7
           IF (NNSGN(ISTAGE) .LE. 0) GO TO 700                                  ANLYZ8
           NGM1=NG-1                                                            ANLYZ4
           NNINEQ=NINEQ-1                                                       ANLYZ5
           IF (NONNEG) GO TO 510                                                ANLYZ6
           NNINEQ=NINEQ+NGM1                                                    ANLYZ7
           IF (NNINEQ .LE. MINEQ) GO TO 510                                     ANLYZ8
           CALL ERRMES (6,.FALSE.,IHOLER,NOUT)                                  ANLYZ9
           GO TO 790                                                            ANLYZ0
      510  IROW=NNINEQ-NGM1                                                     ANLYZ1
           DO 520 J=1,NGM1                                                      ANLYZ2
               IROW=IROW+1                                                     ANLYZ3
               DO 525 ICOL=1,NGLP1                                             ANLYZ4
                   AINEQ(IROW,ICOL)=ZERO                                       ANLYZ5
      525      CONTINUE                                                        ANLYZ6
               AINEQ(IROW,J)=ONE                                               ANLYZ7
               AINEQ(IROW,J+1)=-ONE                                            ANLYZ8
               IISIGN(J)=1                                                     ANLYZ9
      520  CONTINUE                                                            ANLYZ0
           CALL SETGA1 (NNINEQ,                                                 ANLYZ1
```

```
   1   A,AINEQ,MA,MG,MINEQ,MREG,NGL,NGLE,REG)                              ANLYZ2
       NNSGNI=MINO(NNSGN(ISTAGE),4)                                        ANLYZ3
       ALPOLD=ZERO                                                         ANLYZ4
       IF (ISTAGE .EQ. 1)  BTEST=SRANGE                                    ANLYZ5
       DO 600 INSGN=1,NNSGNI                                               ANLYZ0
         NSGNI=NSGN(INSGN)                                                 ANLYZ1
         LNINEQ=NNINEQ                                                     ANLYZ2
         IF (NONNEG)  LNINEQ=LNINEQ+(NSGNI-(1+LSIGN(1,INSGN))/2)/2+1       ANLYZ3
         IF (LNINEQ .LE. MINEQ)  GO TO 610                                 ANLYZ4
         CALL ERRMES (7,.FALSE.,IHOLER,NOUT)                               ANLYZ5
         GO TO 790                                                         ANLYZ6
   610   NNQUSR=NINEQ                                                      ANLYZ7
         IF (NONNEG)  NNQUSR=NNQUSR-NG                                     ANLYZ8
         RALPFL=ONE                                                        ANLYZ9
         IF (MAXO(NQPROG(1),NQPROG(2)) .GT. 1)  RALPFL=RALPHA              ANLYZ0
         ALPHA=ALPBES/RALPFL                                               ANLYZ1
         MFLAT=MAXO(1,NFLAT(INSGN,ISTAGE))                                 ANLYZ2
         IF (RALPFL .LE. ONE)  MFLAT=1                                     ANLYZ3
         DO 620 JFLAT=1,MFLAT                                              ANLYZ8
           ALPHA=ALPHA*RALPFL                                              ANLYZ9
           IF (ABS(ALPOLD/ALPHA-ONE) .LE. 1.E3*PRECIS)  GO TO 630          ANLYZ0
           ALPOLD=ALPHA                                                    ANLYZ1
           LDUM=INSGN.EQ.1 .AND. JFLAT.EQ.1                                ANLYZ2
           CALL SETVAL (ALPHA,LDUM,NNINEQ,                                 ANLYZ3
   1       A,AINEQ,MA,MG,MINEQ,MREG,NGL,NGLE,REG,RHSNEQ,S,VALPCV,VALPHA    ANLYZ4
   2       VK1Y1)                                                          ANLYZ5
   630     J=INSGN                                                         ANLYZ6
           CALL SETSGN (J,NSGNI,LSIGN,NOUT,LLSIGN,NG,SOLBES,SRANGE)        ANLYZ7
           CALL ANPEAK (LNINEQ,                                            ANLYZ1
   1       A,AA,AINEQ,ALPHA,BTEST,CQUAD,DEGFRZ,EXACT,FLAT,G,IISIGN,        ANLYZ2
   2       ISTAGE,IWORK,LBIND,LLSIGN,LSDONE,MA,MDONE,MG,MINEQ,             ANLYZ3
   3       MREG,MWORK,MY,NGLE,NGLY,NNINEQ,NNQUSR,                          ANLYZ4
   4       NSGNI,REG,RHSNEQ,S,SAVBES,SOLBES,SOLPK,                         ANLYZ5
   5       SOLUTN,SQRTW,T,VALPCV,VALPHA,VARZ,VDONE,WORK,Y,YLYFIT)          ANLYZ6
           IF (.NOT.FLAT)  GO TO 650                                       ANLYZ7
   620   CONTINUE                                                          ANLYZ8
   650   DO 660 J=1,NGL                                                    ANLYZ2
           SOLUTN(J)=SOLPK(J)                                              ANLYZ3
   660   CONTINUE                                                          ANLYZ4
         CALL RUNRES (1,SOLUTN,.FALSE.,SINGLE(ALPHA/S(1,1)),               ANLYZ5
   1     CQUAD,G,IPLFIT,IPLRES,ISTAGE,ITITLE,IUNIT,IWT,LINEPG,MWORK,NG,    ANLYZ6
   2     NGL,NLINF,NOUT,NY,SQRTW,SRANGE,T,WORK,Y,YLYFIT)                   ANLYZ7
   600 CONTINUE                                                            ANLYZ8
       IF (ISTAGE.EQ.2 .OR. .NOT.NONNEG)  GO TO 700                        ANLYZ9
       NINEQ=NINEQ-NG                                                      ANLYZ3
       CALL SETNNG (AINEQ,MINEQ,NG,NGLP1,NINEQ)                            ANLYZ4
   700 IF (ISTAGE .EQ. 1)  GO TO 800                                       ANLYZ5
  5700 FORMAT ('1CONTIN - VERSION 1 (NOV 1980)',3X,80A1,4X,                ANLYZ9
   1   'CHOSEN SOLUTION'//5X,'ALPHA',4X,                                   ANLYZ0
   2   'ALPHA/S(1)',5X,'OBJ. FCTN.',7X,'VARIANCE',6X,'STD. DEV.',4X,       ANLYZ1
   3   'DEG FREEDOM',4X,'PROB1 TO REJECT     PROB2 TO REJECT'/             ANLYZ2
   4   1X,1PE9.2,E14.2,2E15.5,E15.3,0PF15.3,2F19.3)                        ANLYZ3
       RTOT=ALPBES                                                         ANLYZ4
       WRITE (NOUT,5700) ITITLE,RTOT,SAVBES                                ANLYZ5
       DO 710 J=1,NGL                                                      ANLYZ0
         YLYFIT(J)=SOLBES(J)                                               ANLYZ1
   710 CONTINUE                                                            ANLYZ2
       CALL PLPRIN (G,YLYFIT,EXACT,NG,ONLY1,NOUT,SRANGE,NLINF,NG,NGL)      ANLYZ3
       IF (DOUSOU)  CALL USEROU (G,YLYFIT,EXACT,MG)                        ANLYZ4
       IF (DOMOM)  CALL MOMENT (G,YLYFIT,CQUAD,NG,MOMNMX(1),MOMNMX(2),     ANLYZ5
   1     NOUT)                                                             ANLYZ6
   790 IF (ISTAGE .NE. 2)  STOP                                            ANLYZ7
   800 RETURN                                                              ANLYZ8
       END                                                                 ANLYZ9
       SUBROUTINE ANPEAK (LNINEQ,                                          ANEAK2
   1     A,AA,AINEQ,ALPHA,BTEST,CQUAD,DEGFRZ,EXACT,FLAT,G,IISIGN,          ANEAK3
   2     ISTAGE,IWORK,LBIND,LLSIGN,LSDONE,MA,MDONE,MG,MINEQ,               ANEAK4
   3     MREG,MWORK,MY,NGLE,NGLY,NNINEQ,NNQUSR,                            ANEAK5
   4     NSGNI,REG,RHSNEQ,S,SAVBES,SOLBES,SOLPK,                           ANEAK6
   5     SOLUTN,SQRTW,T,VALPCV,VALPHA,VARZ,VDONE,WORK,Y,YLYFIT)            ANEAK7
       DOUBLE PRECISION PRECIS, RANGE                                      ANEAK8
       DOUBLE PRECISION A, AA, AINEQ, ALPHA, DUB, REG, RHSNEQ, S,          ANEAK9
```

```
      1 SOLBES, SOLUTN, VALPCV, VALPHA, WORK                              ANEAK0
        LOGICAL DOMOM, DOUSIN, DOUSNQ, DOUSOU, LAST, NONNEG, ONLY1, PRWT, ANEAK1
      1 PRY, SIMULA, LUSER                                                ANEAK2
        LOGICAL DONE, FLAT, LDUM, LBIND, FFLAT                            ANEAK3
        CHARACTER IFORMT(70), IFORMW(70), IFORMY(70),LA(6,46), ITITLE(80),
      + IHOLER(6), ISTAR(4)
        DIMENSION S(MG,3), LLSIGN(5), LSDONE(MDONE,3,2), VDONE(MDONE),    ANEAK4
      1 A(MA,MG), REG(MREG,MG), RHSNEQ(MINEQ), VALPHA(MG), IISIGN(MG),    ANEAK5
      2 AINEQ(MINEQ,MG), WORK(MWORK), IWORK(MA), VALPCV(MG),              ANEAK6
      3 G(MG), EXACT(MG), CQUAD(MG), SOLUTN(MG),                          ANEAK7
      4 LBIND(MINEQ), SOLPK(MG), AA(MG,MG), SOLBES(MG),                   ANEAK8
      5 SQRTW(MY), T(MY), Y(MY), YLYFIT(MY), SAVBES(7)                    ANEAK9
        DIMENSION JSTAGE(4), INC(4), PREJ(2),                             ANEAK0
      1 VARTRY(4), LLSTRY(5,4)                                            ANEAK1
        COMMON /SBLOCK/ PRECIS, RANGE, SRMIN,                             ANEAK2
      1 ALPST(2), GMNMX(2), PLEVEL(2,2), RSVMNX(2,2), RUSER(100),         ANEAK3
      2 EXMAX, SRANGE                                                     ANEAK4
        COMMON /IBLOCK/ IGRID, IPLRES, IPRINT, IQUAD, IUNIT, IWT,         ANEAK5
      1 LINEPG, MIOERR, MQPITR, MFG, NERFIT, NC, NINTT, NLINF, NORDER,    ANEAK6
      2 ICRIT(2), IPLFIT(2),
      3 IUSER(50), LSIGN(4,4), MOMNMX(2), NENDZ(2),                       ANEAK8
      4 NFLAT(4,2), NGL, NGLP1, NIN, NINEQ, NNSGN(2), NOUT, NQPROG(2),    ANEAK9
      5 NSGN(4), NY                                                       ANEAK0
        COMMON /CBLOCK/ IFORMT, IFORMW, IFORMY,LA, ITITLE
        COMMON /LBLOCK/ DOMOM, DOUSIN, DOUSNQ, DOUSOU, LAST, NONNEG,      ANEAK1
      1 ONLY1, PRWT, PRY, SIMULA,                                         ANEAK2
      2 LUSER(30)                                                         ANEAK3
        DATA IHOLER/'A','N','P','E','A','K'/,                             ANEAK4
      1 ISTAR/' ','x','X','F'/                                            ANEAK5
        NSGNM1=NSGNI-1                                                    ANEAK6
        DONE=.FALSE.                                                      ANEAK7
        FLAT=.FALSE.                                                      ANEAK8
        NDONE=0                                                           ANEAK9
        NQPITR=0                                                          ANEAK0
        ITER=0                                                            ANEAK1
        VARRBS=SRANGE                                                     ANEAK2
        DUB=0.                                                            ANEAK3
        DO 110 J=1,NSGNI                                                  ANEAK4
          JSTAGE(J)=0                                                     ANEAK5
          INC(J)=1                                                        ANEAK6
    110 CONTINUE                                                          ANEAK7
   5200 FORMAT (' ',I15,'-EXTREMA-CONSTRAINED ANALYSIS'/                   ANEAK8
      1 '0ALPHA =',1PE9.2,5X,'ALPHA/S(1) =',E9.2/                         ANEAK9
      2 '0ITER.    OBJ. FCTN.        VARIANCE',7X,                        ANEAK0
      3 'STD. DEV.  DEG FREEDOM   PROB1 REJ    PROB2 REJ',10X,            ANEAK1
      4 'EXTREMA INDICES')                                                ANEAK2
        DUM=ALPHA/S(1,1)                                                  ANEAK3
        DDUM=ALPHA                                                        ANEAK4
        WRITE (NOUT,5200) NSGNM1,DDUM,DUM                                 ANEAK5
    200 ITER=ITER+1                                                       ANEAK9
        IF (NDONE .LE. 0) GO TO 230                                       ANEAK0
        DO 210 K=1,NDONE                                                  ANEAK5
          DO 220 J=1,NSGNM1                                               ANEAK6
            L=IABS(LLSIGN(J+1))                                           ANEAK7
            LL=LSDONE(K,J,1)                                              ANEAK8
            IF ((LL.LE.0 .AND. L.NE.-LL)                                  ANEAK9
      1 .OR.       (LL.GT.0 .AND. L.LT.LL)) GO TO 210                     ANEAK0
            LL=LSDONE(K,J,2)                                              ANEAK1
            IF ((LL.LE.0 .AND. L.NE.-LL)  .OR.    (LL.GT.0 .AND. L.GT.LL))ANEAK2
      1 GO TO 210                                                         ANEAK3
    220   CONTINUE                                                        ANEAK4
          LSTAR=3                                                         ANEAK5
          VARREG=VDONE(K)                                                 ANEAK6
          GO TO 320                                                       ANEAK7
    210 CONTINUE                                                          ANEAK8
    230 CALL UPDSGN (NSGNI,LLSIGN,                                        ANEAK3
      1 A,AINEQ,IISIGN,MA,MG,MINEQ,MREG,NGLE,NGLP1,NNINEQ,                ANEAK4
      2 NNQUSR,NONNEG,NOUT,REG,RHSNEQ,S,VALPHA)                           ANEAK5
        NQPITR=NQPITR+1                                                   ANEAK6
        IF (NQPITR .LE. MQPITR) GO TO 235                                 ANEAK7
        CALL ERRMES (1,.FALSE.,IHOLER,NOUT)                               ANEAK8
        GO TO 790                                                         ANEAK9
```

```
235 LDUM=ISTAGE .EQ. 1                                                    ANEAK0
    CALL LDPETC (.FALSE.,LNINEQ,LDUM,ICRIT(ISTAGE),.FALSE.,,FALSE.,       ANEAK4
   1 .FALSE.,ALPHA,.FALSE.,,FALSE.,DUB,VAR,                               ANEAK5
   2 A,AA,AINEQ,BTEST,CQUAD,DEGFRE,DEGFRZ,EXACT,G,IERROR,                 ANEAK6
   3 ISTAGE,IWORK,LBIND,MA,MG,MINEQ,MREG,MWORK,MY,                        ANEAK7
   4 NGLE,NGLY,PREJ,REG,RHSNEQ,S,SAVBES,SOLBES,                           ANEAK8
   5 SOLUTN,SQRTW,T,VALPCV,VALPHA,VARREG,VARZ,WORK,Y,YLYFIT)               ANEAK9
    IF (IERROR .EQ. 1) GO TO 240                                          ANEAK0
    LSTAR=4                                                               ANEAK1
    VARREG=SRANGE                                                         ANEAK2
    GO TO 320                                                             ANEAK3
240 NDONE=NDONE+1                                                         ANEAK4
    IF (NDONE.LE.MBORE) GO TO 250                                         ANEAK5
    CALL ERRMES (2,,FALSE.,IHOLER,NOUT)                                   ANEAK6
    GO TO 790                                                             ANEAK7
250 CALL UPDDON (                                                         ANEAK3
   1 NSGNM1,LLSIGN,LSDONE,MDONE,NDONE,NNQUSR,LBIND,MINEQ,                 ANEAK4
   2 NG,VARREG,VDONE)                                                     ANEAK5
    LSTAR=1                                                               ANEAK6
    IF (VARREG .GE. VARRBS) GO TO 320                                     ANEAK7
    LSTAR=2                                                               ANEAK1
    VARRBS=VARREG                                                         ANEAK2
    DO 310 J=1,NGL                                                        ANEAK3
      SOLPK(J)=SOLUTN(J)                                                  ANEAK4
310 CONTINUE                                                              ANEAK5
    FLAT=FFLAT (NSGNI,NONNEG,NG,SOLUTN,SRMIN,NNQUSR,LBIND,                ANEAK6
   1 MINEQ,LLSIGN)                                                        ANEAK7
5320 FORMAT (1X,A1,I4,1PE16.6,E16.5,E16.3,0PF14.3,2F12.3,8X,5I5)          ANEAK1
320 DUM=SRANGE                                                            ANEAK2
    DDUM=FLOAT(NY)-DEGFRE                                                 ANEAK3
    IF (LSTAR.LE.2 .AND. DDUM.GT.0.) DUM=SQRT(VAR/DDUM)                   ANEAK4
    IF (LSTAR .LE. 2) WRITE (NOUT,5320) ISTAR(LSTAR),ITER,VARREG,VAR,ANEAK5
   1 DUM,DEGFRE,PREJ,(LLSIGN(J),J=1,NSGNI)                                ANEAK6
5322 FORMAT (1X,A1,I4,1PE16.6,78X,5I5)                                    ANEAK7
    IF (LSTAR .GE. 3) WRITE (NOUT,5322) ISTAR(LSTAR),ITER,VARREG,         ANEAK8
   1 (LLSIGN(J),J=1,NSGNI)                                                ANEAK9
    CALL UPDLLS (NSGNI,JSTAGE,NOUT,VARTRY,VARREG,LLSTRY,LLSIGN,           ANEAK3
   1 INC,DONE)                                                            ANEAK4
    IF (.NOT.DONE) GO TO 200                                              ANEAK8
    CALL PLPRIN (G,SOLPK,EXACT,NG,ONLY1,NOUT,SRANGE,NLINF,NG,NGL)         ANEAK9
    IF (DOUSOU) CALL USEROU (G,SOLPK,EXACT,MG)                            ANEAK0
    IF (DOMOM) CALL MOMENT (G,SOLPK,CQUAD,NG,MOMNMX(1), MOMNMX(2),        ANEAK1
   1NOUT)                                                                 ANEAK2
    GO TO 795                                                             ANEAK3
790 FLAT=.FALSE.                                                          ANEAK4
795 LLSTRY(1,1)=1                                                         ANEAK9
    LLSTRY(2,1)=NG                                                        ANEAK0
    CALL UPDSGN (1,LLSTRY,                                                ANEAK1
   1 A,AINEQ,IISIGN,MA,MG,MINEQ,MREG,NGLE,NGLP1,NNINEQ,                   ANEAK2
   2 NNQUSR,NONNEG,NOUT,REG,RHSNEQ,S,VALPHA)                              ANEAK3
    RETURN                                                                ANEAK4
    END                                                                   ANEAK5
    FUNCTION BETAIN (X,A,B,NOUT)                                          BEAIN1
    LOGICAL SWAP                                                          BEAIN2
    CHARACTER IHOLER(6)                                                   BEAIN3
    DATA IHOLER/'B','E','T','A','I','N'/, TOL/1.E-5/                      BEAIN4
    IF (X.LT.0. .OR. X.GT.1. .OR. AMIN1(A,B).LE.0. .OR. AMAX1(A,B)        BEAIN5
   1.GE.2.E+4) CALL ERRMES (1,,TRUE.,IHOLER,NOUT)                         BEAIN6
    BETAIN=X                                                              BEAIN7
    IF (X.LE.0. .OR. X.GE.1.) RETURN                                      BEAIN8
    SWAP=X .GT. .5                                                        BEAIN9
    IF (SWAP) GO TO 150                                                   BEAIN0
    XX=X                                                                  BEAIN1
    AA=A                                                                  BEAIN2
    BB=B                                                                  BEAIN3
    GO TO 200                                                             BEAIN4
150 XX=1.-X                                                               BEAIN9
    AA=B                                                                  BEAIN0
    BB=A                                                                  BEAIN1
200 CX=1.-XX                                                              BEAIN2
    R=XX/CX                                                               BEAIN3
    IMAX=MAX0(0,INT((R*BB-AA-1.)/(R+1.)))                                 BEAIN7
    RI=FLOAT(IMAX)                                                        BEAIN8
```

```
      SUM=0.                                                    BEAIN9
      TERMAX=(AA+RI)*ALOG(XX)+(BB-RI-1.)*ALOG(CX)+GAMLN(AA+BB)- BEAIN0
    1 GAMLN(AA+RI+1.)-GAMLN(BB-RI)                              BEAIN1
      IF (TERMAX .LT. -50.)  GO TO 700                          BEAIN2
      TERMAX=EXP(TERMAX)                                        BEAIN3
      TERM=TERMAX                                               BEAIN4
      SUM=TERM                                                  BEAIN5
      I1=IMAX+1                                                 BEAIN9
      DO 250 I=I1,20000                                         BEAIN0
        RI=FLOAT(I)                                             BEAIN1
        TERM=TERM*R*(BB-RI)/(AA+RI)                             BEAIN2
        SUM=SUM+TERM                                            BEAIN3
        IF (ABS(TERM) .LE. TOL*SUM)  GO TO 300                  BEAIN4
  250 CONTINUE                                                  BEAIN5
      CALL ERRMES (2,.TRUE.,IHOLER,NOUT)                        BEAIN6
  300 IF (IMAX .EQ. 0)  GO TO 700                               BEAIN7
      TERM=TERMAX                                               BEAIN1
      RI=FLOAT(IMAX)                                            BEAIN2
      DO 320 I=1,IMAX                                           BEAIN3
        TERM=TERM*(AA+RI)/(R*(BB-RI))                           BEAIN4
        SUM=SUM+TERM                                            BEAIN5
        IF (ABS(TERM) .LE. TOL*SUM)  GO TO 700                  BEAIN6
        RI=RI-1.                                                BEAIN7
  320 CONTINUE                                                  BEAIN8
  700 BETAIN=SUM                                                BEAIN9
      IF (SWAP)  BETAIN=1.-BETAIN                               BEAIN0
      RETURN                                                    BEAIN1
      END                                                       BEAIN2
      SUBROUTINE CQTRAP (G,CQUAD,NG)                            CQRAP4
      DIMENSION G(NG), CQUAD(NG)                                CQRAP5
      JJ=NG-1                                                   CQRAP6
      DELOLD=0.                                                 CQRAP7
      DO 110 J=1,JJ                                             CQRAP8
        DEL=.5*(G(J+1)-G(J))                                    CQRAP9
        CQUAD(J)=DEL+DELOLD                                     CQRAP0
        DELOLD=DEL                                              CQRAP1
  110 CONTINUE                                                  CQRAP2
      CQUAD(NG)=DELOLD                                          CQRAP3
      RETURN                                                    CQRAP4
      END                                                       CQRAP5
      SUBROUTINE CVNEQ (ALPHA,IERROR,NNNNEQ,SOLUTN,             CVNEQ1
    1 A,AA,AINEQ,DEGFRE,LBIND,MA,MG,MINEQ,MREG,MWORK,NGL,NGLE,  CVNEQ2
    2 NGLP1,NGLY,NOUT,RANGE,REG,S,VALPCV,WORK)                  CVNEQ3
      DOUBLE PRECISION A, AA, ABS, AINEQ, ALPHA, DUB, RANGE, REG, S, CVNEQ4
    1 SOLUTN, VALPCV, WORK, ZERO                                CVNEQ5
      LOGICAL LBIND                                             CVNEQ6
      DIMENSION AA(MG,MG), WORK(MWORK), A(MA,MG), S(MG,3), SOLUTN(MG), CVNEQ7
    1 AINEQ(MINEQ,MG), VALPCV(MG), REG(MREG,MG), LBIND(MINEQ)   CVNEQ8
      CHARACTER IHOLER(6)                                       CVNEQ9
      DATA IHOLER/'C','V','N','E','Q',' '/                      CVNEQ0
      ABS(DUB)=DABS(DUB)                                        CVNEQ1
      ZERO=0.D0                                                 CVNEQ3
      DEGFRE=0.                                                 CVNEQ4
      IERROR=1                                                  CVNEQ5
      NGLEP1=NGLE+1                                             CVNEQ6
      IY=NGLEP1*(NNNNEQ+2)                                      CVNEQ7
      IW=-NNNNEQ                                                CVNEQ8
      NBIND=0                                                   CVNEQ9
      IF (NNNNEQ .EQ. 0)  GO TO 180                             CVNEQ0
      DO 150 IROW=1,NNNNEQ                                      CVNEQ1
        IY=IY+1                                                 CVNEQ2
        LBIND(IROW)=WORK(IY) .GT. ZERO                          CVNEQ3
        IF (.NOT.LBIND(IROW))  GO TO 150                        CVNEQ4
        L=0                                                     CVNEQ9
        DO 152 ICOL=1,NGL                                       CVNEQ0
          IF (ABS(AINEQ(IROW,ICOL)) .LE. ZERO)  GO TO 152       CVNEQ1
          IF (L .NE. 0)  GO TO 154                              CVNEQ2
          L=ICOL                                                CVNEQ3
  152   CONTINUE                                                CVNEQ4
        SOLUTN(L)=AINEQ(IROW,NGLP1)/AINEQ(IROW,L)               CVNEQ5
  154   NBIND=NBIND+1                                           CVNEQ1
```

```
              IW=IW+1                                                 CVNEQ2
              IIW=IW+NNNNEQ                                           CVNEQ3
              DO 160 ICOL=1,NGLE                                      CVNEQ4
                 WORK(IIW)=A(IROW,ICOL)/S(ICOL,2)                     CVNEQ5
                 IIW=IIW+NNNNEQ                                       CVNEQ6
       160    CONTINUE                                                CVNEQ7
              DUB=AINEQ(IROW,NGLP1)                                   CVNEQ8
              DO 170 J=1,NGL                                          CVNEQ9
                 DUB=DUB-AINEQ(IROW,J)*VALPCV(J)                      CVNEQ0
       170    CONTINUE                                                CVNEQ1
              WORK(IIW)=DUB                                           CVNEQ2
       150 CONTINUE                                                   CVNEQ3
           IF (NBIND .LT. NGLE)  GO TO 180                            CVNEQ4
           CALL ERRMES (1,.FALSE.,IHOLER,NOUT)                        CVNEQ5
      5180 FORMAT (1X,2I4)                                            CVNEQ6
           WRITE (NOUT,5180) NBIND,NGLE                               CVNEQ7
           STOP                                                       CVNEQ8
       180 DO 190 J=1,NGLY                                            CVNEQ9
              DO 195 K=1,NGLE                                         CVNEQ0
                 AA(J,K)=ZERO                                         CVNEQ1
       195    CONTINUE                                                CVNEQ2
              AA(J,J)=S(J,1)                                          CVNEQ3
              AA(J,NGLEP1)=A(J,NGLP1)-S(J,1)*REG(J,NGLP1)             CVNEQ4
       190 CONTINUE                                                   CVNEQ5
           IF (NBIND .EQ. 0)  GO TO 200                               CVNEQ6
           IW=NGLP1*NNNNEQ+1                                          CVNEQ7
           IIW=IW+NGL                                                 CVNEQ8
           CALL ELIMEQ (WORK,NNNNEQ,MG,WORK(IW),NBIND,NGLE,AA,MG,AA,MG, CVNEQ9
         1 0,NGLEP1,NGLY,WORK(IIW),RANGE)                             CVNEQ0
           J=NBIND+1                                                  CVNEQ1
           CALL SVDRS2 (AA(1,J),MG,NGLY,NGLE-NBIND,AA(1,NGLEP1),       CVNEQ2
         1 MG,0,WORK,IERROR,RANGE)                                    CVNEQ3
           IF (IERROR .EQ. 1)  GO TO 250                              CVNEQ4
           CALL ERRMES (2,.FALSE.,IHOLER,NOUT)                        CVNEQ5
           RETURN                                                     CVNEQ6
       200 DO 210 J=1,NGLE                                            CVNEQ7
              WORK(J)=S(J,1)                                          CVNEQ8
       210 CONTINUE                                                   CVNEQ9
       250 DUM=ALPHA**2                                               CVNEQ0
           K=MIN0(NGLY,NGLE-NBIND)                                    CVNEQ1
           DO 260 J=1,K                                               CVNEQ2
              DDUM=WORK(J)**2                                         CVNEQ3
              DEGFRE=DEGFRE+DDUM/(DUM+DDUM)                           CVNEQ4
       260 CONTINUE                                                   CVNEQ5
           RETURN                                                     CVNEQ6
           END                                                        CVNEQ7
           SUBROUTINE DIAGA (A,MA,MG,MREG,NEQ,NGL,NGLE,NGLP1,NGLY,REG,S) DIAGA8
           DOUBLE PRECISION A, DUM, REG, S, ZERO                      DIAGA9
           DIMENSION A(MA,MG), REG(MREG,MG), S(MG,3)                  DIAGA0
           ZERO=0.D0                                                  DIAGA2
           IF (NGLY .GE. NGLE)  GO TO 150                             DIAGA3
           K=NGLY+1                                                   DIAGA4
           DO 140 J=K,NGLE                                            DIAGA5
              S(J,1)=ZERO                                             DIAGA6
              A(J,NGLP1)=ZERO                                         DIAGA7
       140 CONTINUE                                                   DIAGA8
       150 DO 160 IROW=1,NGL                                          DIAGA9
              DO 170 ICOL=1,NGLE                                      DIAGA0
                 IICOL=NEQ                                            DIAGA1
                 DUM=ZERO                                             DIAGA2
                 DO 180 J=1,NGLE                                      DIAGA3
                    IICOL=IICOL+1                                     DIAGA4
                    DUM=DUM+REG(IROW,IICOL)*A(J,ICOL)                 DIAGA5
       180       CONTINUE                                             DIAGA6
                 S(ICOL,2)=DUM                                        DIAGA7
       170    CONTINUE                                                DIAGA8
              DO 190 ICOL=1,NGLE                                      DIAGA9
                 REG(IROW,ICOL)=S(ICOL,2)                             DIAGA0
       190    CONTINUE                                                DIAGA1
       160 CONTINUE                                                   DIAGA2
           DO 210 IROW=1,NGLE                                         DIAGA3
              DUM=ZERO                                                DIAGA4
              DO 220 ICOL=1,NGLE                                      DIAGA5
```

```
              DUM=DUM+A(ICOL,IROW)*REG(ICOL,NGLP1)                      DIAGA6
  220    CONTINUE                                                        DIAGA7
          S(IROW,2)=DUM                                                  DIAGA8
  210 CONTINUE                                                           DIAGA9
       DO 250 IROW=1,NGLE                                                DIAGA0
          REG(IROW,NGLP1)=S(IROW,2)                                      DIAGA1
  250 CONTINUE                                                           DIAGA2
       IF (NGLE .GE. NGLY)  GO TO 800                                    DIAGA3
       J=NGLE+1                                                          DIAGA4
       DO 260 IROW=J,NGLY                                                DIAGA5
          S(IROW,1)=ZERO                                                 DIAGA6
          REG(IROW,NGLP1)=ZERO                                           DIAGA7
  260 CONTINUE                                                           DIAGA8
  800 RETURN                                                             DIAGA9
      END                                                                DIAGA0
      SUBROUTINE DIAREG (A,AEQ,MA,MEQ,MG,MREG,NEQ,NGL,NGLE,NGLY,         DIREG9
     1 NOUT,PIVOT,RANGE,REG,S)                                           DIREG0
      DOUBLE PRECISION A, AEQ, DUM, ONE, PIVOT, RANGE, REG, S, ZERO      DIREG1
      DIMENSION S(MG,3), REG(MREG,MG), A(MA,MG), PIVOT(MEQ),             DIREG2
     1 AEQ(MEQ,MG)                                                       DIREG3
      CHARACTER IHOLER(6)
      DATA IHOLER/'D','I','A','R','E','G'/                               DIREG4
      ZERO=0.D0                                                          DIREG6
      ONE=1.D0                                                           DIREG8
      ICOL=NEQ                                                           DIREG9
      DO 120 J=1,NGLE                                                    DIREG0
         ICOL=ICOL+1                                                     DIREG1
         IF (S(J,1) .GT. ZERO) GO TO 125                                 DIREG2
         CALL ERRMES (1,.FALSE.,IHOLER,NOUT)                             DIREG3
         K=J-1                                                           DIREG4
 5125    FORMAT (1X,I3)                                                  DIREG5
         WRITE (NOUT,5125) K                                             DIREG6
         STOP                                                            DIREG7
  125    DUM=ONE/S(J,1)                                                  DIREG8
         IROW=NGL+1                                                      DIREG3
         DO 130 I=1,NGLE                                                 DIREG4
            IROW=IROW-1                                                  DIREG5
            IIROW=IROW-NEQ                                               DIREG6
            REG(IROW,ICOL)=REG(IIROW,ICOL)*DUM                           DIREG7
  130    CONTINUE                                                        DIREG8
         IF (NEQ .EQ. 0)  GO TO 120                                      DIREG9
         DO 135 I=1,NEQ                                                  DIREG0
            REG(I,ICOL)=ZERO                                             DIREG1
  135    CONTINUE                                                        DIREG2
  120 CONTINUE                                                           DIREG3
      DO 150 IROW=1,NGLY                                                 DIREG7
         ICOL=NEQ                                                        DIREG8
         DO 155 J=1,NGLE                                                 DIREG9
            ICOL=ICOL+1                                                  DIREG0
            DUM=ZERO                                                     DIREG1
            L=NEQ                                                        DIREG2
            DO 160 K=1,NGLE                                              DIREG3
               L=L+1                                                     DIREG4
               DUM=DUM+A(IROW,L)*REG(L,ICOL)                             DIREG5
  160       CONTINUE                                                     DIREG6
            S(J,1)=DUM                                                   DIREG7
  155    CONTINUE                                                        DIREG8
         DO 165 J=1,NGLE                                                 DIREG9
            A(IROW,J)=S(J,1)                                             DIREG0
  165    CONTINUE                                                        DIREG1
  150 CONTINUE                                                           DIREG2
      IF (NEQ .EQ. 0)  GO TO 800                                         DIREG3
      I=NEQ                                                              DIREG8
      DO 210 J=1,NEQ                                                     DIREG9
         CALL H12 (2,I,I+1,NGL,AEQ(I,1),MEQ,PIVOT(I),REG(1,NEQ+1),       DIREG0
     1   1,MREG,NGLE,RANGE)                                              DIREG1
         I=I-1                                                           DIREG2
  210 CONTINUE                                                           DIREG3
  800 RETURN                                                             DIREG4
      END                                                                DIREG5
      DOUBLE PRECISION FUNCTION DIFF(X,Y)                                DIFF 6
      DOUBLE PRECISION X, Y                                              DIFF 7
      DIFF=X-Y                                                           DIFF 8
```

```
      RETURN                                                         DIFF 9
      END                                                             DIFF 0
      SUBROUTINE ELIMEQ (AEQ,MEQ,MG,PIVOT,NEQ,NGL,A,MA,REG,MREG,      ELMEQ7
     1 NREG,NGLP1,NGLY,VK1Y1,RANGE)                                   ELMEQ8
      DOUBLE PRECISION A, AEQ, DUM, PIVOT, RANGE, REG, VK1Y1, ZERO    ELMEQ9
      DIMENSION AEQ(MEQ,MG), PIVOT(1), A(MA,MG), REG(MREG,MG),        ELMEQ0
     1 VK1Y1(1)                                                       ELMEQ1
      ZERO=0.D0                                                       ELMEQ3
      DO 120 J=1,NGL                                                  ELMEQ4
        VK1Y1(J)=ZERO                                                 ELMEQ5
  120 CONTINUE                                                        ELMEQ6
      IF (NEQ .EQ. 0) RETURN                                          ELMEQ7
      DO 150 I=1,NEQ                                                  ELMEQ8
        II=I                                                          ELMEQ9
        IAEQ=MIN0(I+1,NEQ)                                            ELMEQ0
        CALL H12 (1,II,I+1,NGL,AEQ(I,1),MEQ,PIVOT(I),AEQ(IAEQ,1),     ELMEQ1
     1 MEQ,1,NEQ-I,RANGE)                                             ELMEQ2
        CALL H12 (2,II,I+1,NGL,AEQ(I,1),MEQ,PIVOT(I),A(1,1),          ELMEQ3
     1 MA,1,NGLY,RANGE)                                               ELMEQ4
        IF (NREG .GT. 0) CALL H12 (2,II,I+1,NGL,AEQ(I,1),MEQ, PIVOT(I)ELMEQ5
     1,REG(1,1),MREG,1,NREG,RANGE)                                    ELMEQ6
  150 CONTINUE                                                        ELMEQ7
      VK1Y1(1)=AEQ(1,NGLP1)/AEQ(1,1)                                  ELMEQ8
      IF (NEQ .EQ. 1) GO TO 200                                       ELMEQ9
      DO 170 I=2,NEQ                                                  ELMEQ0
        DUM=ZERO                                                      ELMEQ1
        K=I-1                                                         ELMEQ2
        DO 180 J=1,K                                                  ELMEQ3
          DUM=DUM+AEQ(I,J)*VK1Y1(J)                                   ELMEQ4
  180   CONTINUE                                                      ELMEQ5
        VK1Y1(I)=(AEQ(I,NGLP1)-DUM)/AEQ(I,I)                          ELMEQ6
  170 CONTINUE                                                        ELMEQ7
  200 CALL LH1405 (A(1,NGLP1),NGLY,NEQ,A,MA,VK1Y1)                    ELMEQ8
      IF (NREG .GT. 0) CALL LH1405 (REG(1,NGLP1),NREG,NEQ,REG,MREG,   ELMEQ9
     1 VK1Y1)                                                         ELMEQ0
      I=NEQ                                                           ELMEQ1
      DO 230 J=1,NEQ                                                  ELMEQ2
        CALL H12 (2,I,I+1,NGL,AEQ(I,1),MEQ,PIVOT(I),VK1Y1,1,MG,1,RANGE) ELMEQ3
        I=I-1                                                         ELMEQ4
  230 CONTINUE                                                        ELMEQ5
      RETURN                                                          ELMEQ6
      END                                                             ELMEQ7
      SUBROUTINE ERRMES (N,ABORT,IHOLER,IWRITE)                       ERMES3
      LOGICAL ABORT                                                   ERMES4
      CHARACTER IHOLER(6)                                             ERMES5
 5000 FORMAT ('0ERROR ',6A1,I2,'.  (CHECK USERS GUIDE.)  ',           ERMES6
     1 46('xx'))                                                      ERMES7
      WRITE (IWRITE,5000) IHOLER,N                                    ERMES8
      IF (ABORT) STOP                                                 ERMES9
      RETURN                                                          ERMES0
      END                                                             ERMES1
      LOGICAL FUNCTION FFLAT (NSGNI,NONNEG,NG,SOLUTN,SRMIN,NNQUSR,    FFLAT7
     1 LBIND,MINEQ,LLSIGN)                                            FFLAT8
      DOUBLE PRECISION ABS, AMAX1, SMIN, SOLUTN, ZERO                 FFLAT9
      LOGICAL NONNEG, LBIND                                           FFLAT0
      DIMENSION SOLUTN(NG), LBIND(MINEQ), LLSIGN(NSGNI)               FFLAT1
      AMAX1(SMIN,ZERO)=DMAX1(SMIN,ZERO)                               FFLAT2
      ABS(SMIN)=DABS(SMIN)                                            FFLAT3
      ZERO=0.D0                                                       FFLAT5
      SMIN=ZERO                                                       FFLAT6
      IF (.NOT.NONNEG) GO TO 120                                      FFLAT7
      DO 110 J=1,NG                                                   FFLAT8
        SMIN=AMAX1(SMIN,SOLUTN(J))                                    FFLAT9
  110 CONTINUE                                                        FFLAT0
      SMIN=SMIN*SRMIN                                                 FFLAT1
  120 FFLAT=.FALSE.                                                   FFLAT2
      K=NNQUSR                                                        FFLAT3
      NGM1=NG-1                                                       FFLAT4
      DO 130 J=1,NGM1                                                 FFLAT5
        K=K+1                                                         FFLAT6
        IF (LBIND(K) .AND. ABS(SOLUTN(J)) .GE. SMIN) GO TO 140        FFLAT7
        FFLAT=.FALSE.                                                 FFLAT8
        GO TO 130                                                     FFLAT9
```

```
 140  IF (FFLAT) GO TO 800                                          FFLAT0
      FFLAT=.TRUE.                                                  FFLAT1
      IF (NSGNI .LT. 2)  GO TO 140                                  FFLAT2
      DO 145 L=2,NSGNI                                              FFLAT3
         LL=IABS(LLSIGN(L))                                         FFLAT4
         IF (J.EQ.LL .OR. J.EQ.LL+1)  GO TO 130                     FFLAT5
 145  CONTINUE                                                      FFLAT6
      GO TO 140                                                     FFLAT7
 130  CONTINUE                                                      FFLAT8
      FFLAT=.FALSE.                                                 FFLAT9
 800  RETURN                                                        FFLAT0
      END                                                           FFLAT1
      FUNCTION FISHNI (F,DF1,DF2,NOUT)                              FIHNI9
      CHARACTER IHOLER(6)                                           FIHNI0
      DATA IHOLER/'F','I','S','H','N','I'/                          FIHNI1
      IF (AMIN1(DF1,DF2) .GT. 0.)  GO TO 150                        FIHNI2
      CALL ERRMES (1,.FALSE.,IHOLER,NOUT)                           FIHNI3
      FISHNI=1.                                                     FIHNI4
      RETURN                                                        FIHNI5
 150  HDF1=.5*DF1                                                   FIHNI6
      HDF2=.5*DF2                                                   FIHNI7
      DUM=DF1*F                                                     FIHNI8
      FISHNI=BETAIN(DUM/(DF2+DUM),HDF1,HDF2,NOUT)                   FIHNI9
      RETURN                                                        FIHNI0
      END                                                           FIHNI1
      FUNCTION GAMLN (XARG)                                         GAMLN4
      X=XARG                                                        GAMLN5
      P=1.                                                          GAMLN6
      GAMLN=0.                                                      GAMLN7
 110  IF (X .GE. 7.)  GO TO 150                                     GAMLN8
      P=P*X                                                         GAMLN9
      X=X+1.                                                        GAMLN0
      GO TO 110                                                     GAMLN1
 150  IF (XARG .LT. 7.)  GAMLN=-ALOG(P)                             GAMLN2
      Z=1./X**2                                                     GAMLN3
      GAMLN=GAMLN+(X-.5)*ALOG(X)-X+.9189385-(((Z/1680.-              GAMLN4
     1 7.936508E-4)*Z+2.777778E-3)*Z-8.333333E-2)/X                  GAMLN5
      RETURN                                                        GAMLN6
      END                                                           GAMLN7
      FUNCTION GETPRU (SOL,                                         GEPRU3
     1 CQUAD,G,IUNIT,IWT,MWORK,NG,NGL,NLINF,NY,SQRTW,T,WORK,        GEPRU4
     2 Y,YLYFIT)                                                    GEPRU5
      DOUBLE PRECISION SOL, WORK                                    GEPRU6
      DIMENSION WORK(MWORK), SQRTW(NY), CQUAD(NG), G(NG), T(NY),    GEPRU7
     1 Y(NY), YLYFIT(NY), SOL(NGL)                                  GEPRU8
      CALL GETYLY (SOL,                                             GEPRU9
     1 CQUAD,G,IUNIT,IWT,MWORK,NG,NGL,NLINF,NY,SQRTW,T,WORK,Y,YLYFIT) GEPRU0
      YLYOLD=-YLYFIT(1)                                             GEPRU1
      NRUN=0                                                        GEPRU2
      DDUM=0.                                                       GEPRU3
      DO 110 IROW=1,NY                                              GEPRU4
         DUM=YLYFIT(IROW)                                           GEPRU5
         DDUM=DDUM+SIGN(1.,DUM)                                     GEPRU6
         IF (DUM*YLYOLD .LT. 0.)  NRUN=NRUN+1                       GEPRU7
         YLYOLD=DUM                                                 GEPRU8
 110  CONTINUE                                                      GEPRU9
      RN1=.5*(FLOAT(NY)+DDUM)                                       GEPRU0
      RN2=RN1-DDUM                                                  GEPRU1
      DUM=2.*RN1*RN2                                                GEPRU2
      RMU=DUM/(RN1+RN2)+1.                                          GEPRU3
      SIG=SQRT(DUM*(DUM-RN1-RN2)/(RN1+RN2-1.))/(RN1+RN2)            GEPRU4
      GETPRU=-1.                                                    GEPRU5
      IF (AMIN1(RN1,RN2) .GT. 9.5)  GETPRU=FGAUSS((FLOAT(NRUN)-RMU+.5)/ GEPRU6
     1 SIG)                                                         GEPRU7
      RETURN                                                        GEPRU8
      END                                                           GEPRU9
      SUBROUTINE GETROW (IROW,A,INIT,ISTAGE,INC,IUNIT,              GEROW5
     1 SQRTW,NY,NGL,IWT,NG,CQUAD,G,T,NLINF,Y)                       GEROW6
      DOUBLE PRECISION A                                            GEROW7
      LOGICAL INIT                                                  GEROW8
      DIMENSION SQRTW(NY), A(1), CQUAD(NG), G(NG), T(NY), Y(NY)     GEROW9
C
C     THE FOLLOWING LABELLED COMMON WAS ADDED TO STORE THE VALUES OF
C     THE KERNAL TO AVOID CONSTANT RECOMPUTING. ASSOCIATED COMMON IS
C     IN MAIN.
```

```
C
      COMMON /KERNAL/ USERKK(544,35)
      SWT=SQRTW(IROW)                                                    GEROW0
      JJ=1+INC*NGL                                                       GEROW1
      IF (IUNIT.LT.0 .OR. INIT)  GO TO 200                               GEROW2
      READ (IUNIT) (A(J),J=1,JJ,INC)                                     GEROW6
      GO TO 300                                                          GEROW7
  200 K=1                                                                GEROW1
      DO 210 J=1,NG                                                      GEROW2
        JJJ=J                                                            GEROW3
C
C     A(K)=CQUAD(J)*SWT*USERK(IROW,T,JJJ,G)                              GEROW4
C     THE PRECEDING LINE HAS BEEN REPLACED BY THE FOLLOWING LINE SO THAT
C     THE KERNAL IS STORED IN MEMORY RATHER THAN CONSTANTLY RECOMPUTED.
C     ASSOCIATED WITH THIS CHANGE IS AN ADDITIONAL LABELLED COMMON
C     'KERNAL' IN THIS SUBROUTINE, IN MAIN, AND A SMALL ADDED SECTION
C     IN MAIN.
C
      A(K)=CQUAD(J)*SWT*USERKK(IROW,JJJ)
      K=K+INC                                                            GEROW5
  210 CONTINUE                                                           GEROW6
      IF (NLINF .LE. 0)  GO TO 230                                       GEROW7
      DO 220 J=1,NLINF                                                   GEROW8
        JJJ=J                                                            GEROW9
        A(K)=SWT*USERLF(IROW,JJJ,T,NY)                                   GEROW0
        K=K+INC                                                          GEROW1
  220 CONTINUE                                                           GEROW2
  230 A(K)=Y(IROW)*SWT                                                   GEROW3
      IF (IUNIT .LT. 0)  GO TO 800                                       GEROW4
      WRITE (IUNIT) (A(J),J=1,JJ,INC)                                    GEROW5
  300 IF (IROW .EQ. NY)  REWIND IUNIT                                    GEROW6
  800 RETURN                                                             GEROW7
      END                                                                GEROW8
      SUBROUTINE GETYLY (SOL,                                            GEYLY8
     1 CQUAD,G,IUNIT,IWT,MWORK,NG,NGL,NLINF,NY,SQRTW,T,WORK,Y,YLYFIT)    GEYLY9
      DOUBLE PRECISION DUM, SOL, WORK                                    GEYLY0
      DIMENSION WORK(MWORK), SQRTW(NY), CQUAD(NG), G(NG), T(NY),         GEYLY1
     1 Y(NY), YLYFIT(NY), SOL(NGL)                                       GEYLY2
      DO 110 IROW=1,NY                                                   GEYLY3
        IIROW=IROW                                                       GEYLY4
        CALL GETROW (IIROW,WORK,.FALSE.,0,1,IUNIT,                       GEYLY5
     1  SQRTW,NY,NGL,IWT,NG,CQUAD,G,T,NLINF,Y)                           GEYLY6
        DUM=WORK(NGL+1)                                                  GEYLY7
        DO 120 ICOL=1,NGL                                                GEYLY8
          DUM=DUM-WORK(ICOL)*SOL(ICOL)                                   GEYLY9
  120   CONTINUE                                                         GEYLY0
        YLYFIT(IROW)=DUM                                                 GEYLY1
  110 CONTINUE                                                           GEYLY2
      RETURN                                                             GEYLY3
      END                                                                GEYLY4
      SUBROUTINE G1 (A,B,COS,SIN,SIG)                                    G1    3
      DOUBLE PRECISION A, ABS, B, COS, ONE, SIG, SIGN, SIN, SQRT,        G1    5
     1 XR, YR, ZERO                                                      G1    6
      ABS(A)=DABS(A)                                                     G1    7
      SQRT(A)=DSQRT(A)                                                   G1    8
      SIGN(A,B)=DSIGN(A,B)                                               G1    9
      ZERO=0.D0                                                          G1    1
      ONE=1.D0                                                           G1    3
      IF (ABS(A).LE.ABS(B))  GO TO 10                                    G1    4
      XR=B/A                                                             G1    5
      YR=SQRT(ONE+XR**2)                                                 G1    6
      COS=SIGN(ONE/YR,A)                                                 G1    7
      SIN=COS*XR                                                         G1    8
      SIG=ABS(A)*YR                                                      G1    9
      RETURN                                                             G1    0
   10 IF (B)   20,30,20                                                  G1    1
   20 XR=A/B                                                             G1    2
      YR=SQRT(ONE+XR**2)                                                 G1    3
      SIN=SIGN(ONE/YR,B)                                                 G1    4
      COS=SIN*XR                                                         G1    5
      SIG=ABS(B)*YR                                                      G1    6
      RETURN                                                             G1    7
   30 SIG=ZERO                                                           G1    8
      COS=ZERO                                                           G1    9
```

```
      SIN=ONE                                                   G1    0
      RETURN                                                    G1    1
      END                                                       G1    2
      SUBROUTINE G2    (COS,SIN,X,Y)                            G2    3
      DOUBLE PRECISION COS, SIN, X, XR, Y                       G2    7
      XR=COS*X+SIN*Y                                            G2    8
      Y=-SIN*X+COS*Y                                            G2    9
      X=XR                                                      G2    0
      RETURN                                                    G2    1
      END                                                       G2    2
      SUBROUTINE H12 (MODE,LPIVOT,L1,M,U,IUE,UP,C,ICE,ICV,NCV,RANGE)  H12  5
      DIMENSION U(IUE,1), C(1)                                  H12   6
      DOUBLE PRECISION SM,B                                     H12   7
      DOUBLE PRECISION ABS, AMAX1, C, CL, CLINV, DOUBLE, ONE, RANGE,  H12  8
     1 RANGIN, SIGN, SM1, SQRT, U, UP                           H12   9
      ABS(SM)=DABS(SM)                                          H12   0
      AMAX1(SM,ONE)=DMAX1(SM,ONE)                               H12   1
      DOUBLE(SM)=SM                                             H12   3
      SQRT(SM)=DSQRT(SM)                                        H12   4
      SIGN(SM,ONE)=DSIGN(SM,ONE)                                H12   5
      ONE=1.D0                                                  H12   7
      IF (0.GE.LPIVOT.OR.LPIVOT.GE.L1.OR.L1.GT.M)  RETURN       H12   9
      RANGIN=ONE/RANGE                                          H12   0
      CL=ABS(U(1,LPIVOT))                                       H12   1
      IF (MODE.EQ.2) GO TO 60                                   H12   2
          DO 10 J=L1,M                                          H12   4
   10     CL=AMAX1(ABS(U(1,J)),CL)                              H12   5
      IF (CL .LE. RANGIN) GO TO 130                             H12   6
      CLINV=ONE/CL                                              H12   7
      SM=(DOUBLE(U(1,LPIVOT))*CLINV)**2                         H12   8
          DO 30 J=L1,M                                          H12   9
   30     SM=SM+(DOUBLE(U(1,J))*CLINV)**2                       H12   0
      SM1=SM                                                    H12   2
      CL=-SIGN(CL*SQRT(SM1),U(1,LPIVOT))                        H12   3
      UP=U(1,LPIVOT)-CL                                         H12   4
      U(1,LPIVOT)=CL                                            H12   5
      GO TO 70                                                  H12   6
   60 IF (CL .LE. RANGIN)  GO TO 130                            H12   9
   70 IF (NCV.LE.0)  RETURN                                     H12   0
      B=DOUBLE(UP)*U(1,LPIVOT)                                  H12   1
      IF (B .GE. -RANGIN)  GO TO 130                            H12   4
      B=ONE/B                                                   H12   5
      I2=1-ICV+ICE*(LPIVOT-1)                                   H12   6
      INCR=ICE*(L1-LPIVOT)                                      H12   7
          DO 120 J=1,NCV                                        H12   8
          I2=I2+ICV                                             H12   9
          I3=I2+INCR                                            H12   0
          I4=I3                                                 H12   1
          SM=C(I2)*DOUBLE(UP)                                   H12   2
              DO 90 I=L1,M                                      H12   3
              SM=SM+C(I3)*DOUBLE(U(1,I))                        H12   4
   90         I3=I3+ICE                                         H12   5
          IF (SM)    100,120,100                                H12   6
  100     SM=SM*B                                               H12   7
          C(I2)=C(I2)+SM*DOUBLE(UP)                             H12   8
              DO 110 I=L1,M                                     H12   9
              C(I4)=C(I4)+SM*DOUBLE(U(1,I))                     H12   0
  110         I4=I4+ICE                                         H12   1
  120     CONTINUE                                              H12   2
  130 RETURN                                                    H12   3
      END                                                       H12   4
      SUBROUTINE INIT                                           INIT  6
      DOUBLE PRECISION PRECIS, RANGE                            INIT  7
      DOUBLE PRECISION ONE, ZERO, PREMIN, DIFF,                 INIT  8
     1 SMALL, SIZE, PTRY, DELTRY, AMAX1                         INIT  9
      LOGICAL DOMOM, DOUSIN, DOUSNQ, DOUSOU, LAST, NONNEG, ONLY1, PRWT,  INIT  0
     1 PRY, SIMULA, LUSER                                       INIT  1
      LOGICAL DONE1                                             INIT  2
      CHARACTER IHOLER(6), IFORMT(70), IFORMW(70), IFORMY(70),
     + LA(6,46), ITITLE(80)
      COMMON /SBLOCK/ PRECIS, RANGE, SRMIN,                     INIT  4
     1 ALPST(2), GMNMX(2), PLEVEL(2,2), RSVMNX(2,2), RUSER(100),  INIT  5
     2 EXMAX, SRANGE                                            INIT  6
      COMMON /IBLOCK/ IGRID, IPLRES, IPRINT, IQUAD, IUNIT, IWT,  INIT  7
     1 LINEPG, MIDERR, MQPITR, NEQ, NERFIT, NG, NINTT, NLINF, NORDER,  INIT  8
     2 ICRIT(2), IPLFIT(2),
```

```
   3    IUSER(50), LSIGN(4,4), MOMNMX(2), NENDZ(2),                INIT  0
   4  NFLAT(4,2), NGL, NGLP1, NIN, NINEQ, NNSGN(2), NOUT, NQPROG(2), INIT 1
   5  NSGN(4), NY                                                  INIT  2
      COMMON /CBLOCK/ IFORMT, IFORMW, IFORMY, LA,ITITLE
      COMMON /LBLOCK/ DOMOM, DOUSIN, DOUSNQ, DOUSOU, LAST, NONNEG,  INIT 3
   1  ONLY1, PRWT, PRY, SIMULA,                                    INIT  4
   2  LUSER(30)                                                    INIT  5
      DATA IHOLER/'I','N','I','T',' ',' '/                         INIT  6
      AMAX1(PTRY,PRECIS)=DMAX1(PTRY,PRECIS)                        INIT  7
      ONE=1.D0                                                     INIT  8
      ZERO=0.D0                                                    INIT  1
      PREMIN=1.D-8                                                 INIT  3
      FACT=RANGE**(-.025)                                          INIT  4
      SMALL=ONE/RANGE                                              INIT  5
      DONE1=.FALSE.                                                INIT  6
      SIZE=RANGE                                                   INIT  7
      DO 110 J=1,80                                                INIT  8
        PTRY=PREMIN                                                INIT  9
        DO 120 K=1,150                                             INIT  0
          PTRY=.5*PTRY                                             INIT  1
          DELTRY=PTRY*SIZE                                         INIT  2
          IF (DELTRY .LT. SMALL)  GO TO 140                        INIT  3
          IF (DIFF(SIZE+DELTRY,SIZE) .LE. ZERO)  GO TO 130         INIT  4
 120    CONTINUE                                                   INIT  5
 130    IF (DONE1)  PRECIS=AMAX1(PTRY,PRECIS)                      INIT  6
        IF (.NOT.DONE1)  PRECIS=PTRY                               INIT  7
        DONE1=.TRUE.                                               INIT  8
        SIZE=FACT*SIZE                                             INIT  9
 110  CONTINUE                                                     INIT  0
 140  PRECIS=20.*PRECIS                                            INIT  1
      IF (PRECIS .GT. PREMIN)  CALL ERRMES (1,.TRUE.,IHOLER,NOUT)  INIT  2
      MIOERR=MAX0(2,MIOERR)                                        INIT  3
      EXMAX=ALOG(SRANGE)                                           INIT  4
      RETURN                                                       INIT  5
      END                                                          INIT  6
      SUBROUTINE INPUT (EXACT,G,MA,MEQ,MG,MINEQ,MREG,MWORK,MY,SQRTW,T,Y)INPUT8
      DOUBLE PRECISION PRECIS, RANGE                               INPUT9
      LOGICAL DOMOM, DOUSIN, DOUSNQ, DOUSOU, LAST, NONNEG, ONLY1, PRWT, INPUT0
   1  PRY, SIMULA, LUSER                                           INPUT1
      LOGICAL LERR                                                 INPUT2
      DIMENSION SQRTW(MY), T(MY), Y(MY), EXACT(MY), G(MG)          INPUT3
      CHARACTER LIN(6)
      CHARACTER IHOLER(6), LA(6,46), LA1(6,14),LA2(6,11),IFORMY(70),
     + LA3(6,14), LA4(6,7), ITITLE(80), IFORMT(70), IFORMW(70)
      COMMON /CBLOCK/ IFORMT, IFORMW, IFORMY, LA,ITITLE
      COMMON /SBLOCK/ PRECIS, RANGE, SRMIN,                        INPUT6
   1  ALPST(2), GMNMX(2), PLEVEL(2,2), RSVMNX(2,2), RUSER(100),    INPUT7
   2  EXMAX, SRANGE                                                INPUT8
      COMMON /IBLOCK/ IGRID, IPLRES, IPRINT, IQUAD, IUNIT, IWT,    INPUT9
   1  LINEPG, MIOERR, MQPITR, NEQ, NERFIT, NG, NINTT, NLINF, NORDER, INPUT0
   2  ICRIT(2), IPLFIT(2),
   3    IUSER(50), LSIGN(4,4), MOMNMX(2), NENDZ(2),                INPUT2
   4  NFLAT(4,2), NGL, NGLP1, NIN, NINEQ, NNSGN(2), NOUT, NQPROG(2), INPUT3
   5  NSGN(4), NY                                                  INPUT4
      COMMON /LBLOCK/ DOMOM, DOUSIN, DOUSNQ, DOUSOU, LAST, NONNEG, INPUT5
   1  ONLY1, PRWT, PRY, SIMULA,                                    INPUT6
   2  LUSER(30)                                                    INPUT7
      EQUIVALENCE (LA(1,1),LA1(1,1)), (LA(1,15),LA2(1,1)),         INPUT2
   1  (LA(1,26),LA3(1,1)), (LA(1,40),LA4(1,1))                     INPUT3
      DATA MLA/46/, IHOLER/'I','N','P','U','T',' '/                INPUT4
      DATA LA1/                                                    INPUT5
   1  'S','R','M','I','N',' ','A','L','P','S','T',' ',             INPUT6
   2  'G','M','N','M','X',' ','P','L','E','V','E','L',             INPUT7
   3  'R','S','V','M','N','X','R','U','S','E','R',' ',             INPUT8
   4  'I','G','R','I','D',' ','I','P','L','R','E','S',             INPUT9
   5  'I','P','R','I','N','T','I','Q','U','A','D',' ',             INPUT0
   6  'I','U','N','I','T',' ','I','W','T',3*' ',                      IU
   7  'L','I','N','E','P','G','M','I','O','E','R','R'/                IU
      DATA LA2/                                                    INPUT3
   1  'M','Q','P','I','T','R',                                     INPUT4
   2  'N','E','Q',3*' ','N','E','R','F','I','T',                    INPU4
   3  'N','G',' ',' ',' ',' ','N','I','N','T','T',' ',             INPUT6
   4  'N','L','I','N','F',' ','N','O','R','D','E','R',             INPUT7
   5  'I','C','R','I','T',' ',                                     INPUT8
```

```
      6 'I','F','O','R','M','T','I','F','O','R','M','W',                INPUT9
      7 'I','F','O','R','M','Y'/                                         INPUT0
        DATA LA3/                                                        INPUT1
      1 'I','P','L','F','I','T','I','U','S','E','R',' ',                 INPUT2
      2 'L','S','I','G','N',' ','M','O','M','N','M','X',                 INPUT3
      3 'N','E','N','D','Z',' ','N','F','L','A','T',' ',                 INPUT4
      4 'N','N','S','G','N',' ','N','Q','P','R','O','G',                 INPUT5
      5 'N','S','G','N',' ',' ','D','O','M','O','M',' ',                 INPUT6
      6 'D','O','U','S','I','N','D','O','U','S','N','Q',                 INPUT7
      7 'D','O','U','S','O','U','L','A','S','T',' ',' '/                 INPUT8
        DATA LA4/                                                        INPUT9
      1 'N','O','N','N','E','G','O','N','L','Y','1',' ',                 INPUT0
      2 'P','R','W','T',' ',' ','P','R','Y',' ',' ',' ',                 INPUT1
      3 'S','I','M','U','L','A','L','U','S','E','R',' ',                 INPUT2
      4 'E','N','D',' ',' ',' ',' '/                                     INPUT3
 5001 FORMAT (' ')                                                       INPUT4
 5100 FORMAT (80A1)                                                      INPUT5
      READ (NIN,5100) ITITLE                                             INPUT6
 5101 FORMAT ('1CONTIN - VERSION 1 (NOV 1980)',10X,80A1                  INPUT7
     1 //40X,'INPUT DATA FOR CHANGES TO COMMON VARIABLES'/)              INPUT8
      WRITE (NOUT,5101) ITITLE                                           INPUT9
      NIOERR=0                                                           INPUT0
 5200 FORMAT (1X,6A1,I8,E15.6)                                           INPUT1
  200 READ (NIN,5200) LIN,IIN,RIN                                        INPUT2
      WRITE (NOUT,5001)                                                  INPUT3
      WRITE (NOUT,5200) LIN,IIN,RIN                                      INPUT4
      DO 210 J=1,MLA                                                     INPUT5
        DO 220 K=1,6                                                     INPUT6
          IF (LIN(K) .NE. LA(K,J))  GO TO 210                            INPUT7
  220   CONTINUE                                                         INPUT8
        IF (J .EQ. MLA)  GO TO 300                                       INPUT9
        JJ=J                                                             INPUT0
        CALL STORIN (JJ,NIOERR,LIN,IIN,RIN)                              INPUT1
        GO TO 200                                                        INPUT2
  210 CONTINUE                                                           INPUT3
      CALL ERRMES (1,.FALSE.,IHOLER,NOUT)                                INPUT4
      WRITE (NOUT,5001)                                                  INPUT5
      NIOERR=NIOERR+1                                                    INPUT6
      IF (NIOERR .GE. MIOERR)  STOP                                      INPUT7
      GO TO 200                                                          INPUT8
  300 CALL READYT (MY,NIOERR,SQRTW,T,Y)                                  INPUT9
      CALL WRITIN (EXACT,G,MG,MY,SQRTW,T,Y)
      LERR=.FALSE.                                                       INPUT4
      DO 410 K=1,2                                                       INPUT5
        DO 420 J=1,2                                                     INPUT6
          IF (K.EQ.2 .OR. (IWT.NE.1 .AND. IWT.NE.4))  LERR=              INPUT7
     1LERR .OR.    PLEVEL(J,K).LT.0. .OR. PLEVEL(J,K)                    INPUT8
     2.GT.1. .OR. ICRIT(K).LT.1    .OR. ICRIT(K).GT.2                    INPUT9
          IF (NQPROG(K) .GT. 0)  LERR=LERR .OR. RSVMNX(J,K).LE.0.        INPUT0
  420   CONTINUE                                                         INPUT1
  410 CONTINUE                                                           INPUT2
      LERR=LERR .OR. MINO(IGRID,IQUAD,IWT,NG-1,NG+NLINF-NEQ).LT.1 .OR.   INPUT3
     1 MINO(NLINF,NEQ).LT.0 .OR.                                         INPUT4
     2 MAXO(IGRID-3,IQUAD-3,IWT-5,NEQ-MEQ,NG+NLINF+2-MINO(MG,MA),        INPUT5
     3 NG+NLINF+1-MREG,NORDER-5,                                         INPUT6
     4 MAXO(MG,NY)-MY,MAXO((MINEQ+2)*(MG+1)-4,MG+NLINF+1)-MWORK) .GT. 0  INPUT7
      IF (.NOT.LERR)  GO TO 500                                          INPUT8
      CALL ERRMES (2,.FALSE.,IHOLER,NOUT)                                INPUT9
 5420 FORMAT (' MY =',I5,5X,'MA =',I3,5X,'MG =',I3,5X,'MREG =',I3,5X,    INPUT0
     1 'MINEQ =',I3,5X,'MEQ =',I3,5X,'MWORK =',I5)                       INPUT1
      WRITE (NOUT,5420) MY,MA,MG,MREG,MINEQ,MEQ,MWORK                    INPUT2
      STOP                                                               INPUT3
  500 IF (NIOERR .NE. 0)  STOP                                           INPUT4
      RETURN                                                             INPUT5
      END                                                                INPUT6
      SUBROUTINE LDP (G,MDG,M,N,H,X,XNORM,W,INDEX,MODE,RANGE)            LDP  2
      DOUBLE PRECISION DIFF, FAC, G, H, ONE, RANGE, RNORM,               LDP  7
     1 SQRT, W, X, XNORM, ZERO                                           LDP  8
      INTEGER INDEX(M)                                                   LDP  9
      DIMENSION G(MDG,N), H(M), X(1), W(1)                               LDP  0
      SQRT(FAC)=DSQRT(FAC)                                               LDP  1
      ZERO=0.D0                                                          LDP  3
      ONE=1.D0                                                           LDP  5
      IF (N.LE.0)  GO TO 120                                             LDP  6
        DO 10 J=1,N                                                      LDP  7
   10   X(J)=ZERO                                                        LDP  8
```

```
           XNORM=ZERO                                                        LDP  9
           IF (M.LE.0)  GO TO 110                                            LDP  0
           IW=0                                                              LDP  2
              DO 30 J=1,M                                                    LDP  3
                 DO 20 I=1,N                                                 LDP  4
                    IW=IW+1                                                  LDP  5
  20                W(IW)=G(J,I)                                             LDP  6
                 IW=IW+1                                                     LDP  7
  30             W(IW)=H(J)                                                  LDP  8
           IF=IW+1                                                           LDP  9
              DO 40 I=1,N                                                    LDP  1
                 IW=IW+1                                                     LDP  2
  40             W(IW)=ZERO                                                  LDP  3
           W(IW+1)=ONE                                                       LDP  4
           NP1=N+1                                                           LDP  6
           IZ=IW+2                                                           LDP  7
           IY=IZ+NP1                                                         LDP  8
           IWDUAL=IY+M                                                       LDP  9
           CALL NNLS (W,NP1,NP1,M,W(IF),W(IY),RNORM,W(IWDUAL),W(IZ),INDEX,   LDP  1
         1            MODE,RANGE)                                            LDP  2
           IF (MODE.NE.1)  RETURN                                            LDP  4
           IF (RNORM)  130,130,50                                            LDP  5
  50       FAC=ONE                                                           LDP  6
           IW=IY-1                                                           LDP  7
              DO 60 I=1,M                                                    LDP  8
                 IW=IW+1                                                     LDP  9
  60          FAC=FAC-H(I)*W(IW)                                             LDP  1
           IF (DIFF(ONE+FAC,ONE))  130,130,70                                LDP  3
  70       FAC=ONE/FAC                                                       LDP  4
              DO 90 J=1,N                                                    LDP  5
                 IW=IY-1                                                     LDP  6
                    DO 80 I=1,M                                              LDP  7
                       IW=IW+1                                               LDP  8
  80                   X(J)=X(J)+G(I,J)*W(IW)                                LDP  0
  90             X(J)=X(J)*FAC                                               LDP  1
              DO 100 J=1,N                                                   LDP  2
 100             XNORM=XNORM+X(J)**2                                         LDP  3
           XNORM=SQRT(XNORM)                                                 LDP  4
 110       MODE=1                                                            LDP  6
           RETURN                                                            LDP  7
 120       MODE=2                                                            LDP  9
           RETURN                                                            LDP  0
 130       MODE=4                                                            LDP  2
           RETURN                                                            LDP  3
           END                                                               LDP  4
           SUBROUTINE LDPETC (FINDVZ,NNNNEQ,SSEARC,IICRIT,DDOMOM,PPLTPR,     LDETC2
         1 PRLDP,ALPHA,HEADNG,NEWPAG,ALPBES,VAR,                             LDETC3
         2 A,AA,AINEQ,BTEST,CQUAD,DEGFRE,DEGFRZ,EXACT,G,IERROR,              LDETC4
         3 ISTAGE,IWORK,LBIND,MA,MG,MINEQ,MREG,MWORK,MY,                     LDETC5
         4 NGLE,NGLY,PREJ,REG,RHSNEQ,S,SAVBES,SOLBES,                        LDETC6
         5 SOLUTN,SQRTW,T,VALPCV,VALPHA,VARREG,VARZ,WORK,Y,YLYFIT)           LDETC7
           DOUBLE PRECISION PRECIS, RANGE                                    LDETC8
           DOUBLE PRECISION A, AA, AINEQ, ALPBES, ALPHA, DUB, REG,           LDETC9
         1 RHSNEQ, S, SOLBES, SOLUTN, VALPCV, VALPHA, WORK, ZERO             LDETC0
           LOGICAL DOMOM, DOUSIN, DOUSNQ, DOUSOU, LAST, NONNEG, ONLY1, PRWT, LDETC1
         1 PRY, SIMULA, LUSER                                                LDETC2
           LOGICAL FINDVZ, SSEARC, PPLTPR, LBIND, PRLDP, DDOMOM,             LDETC3
         1 NEWPAG, HEADNG                                                    LDETC4
           DIMENSION SOLUTN(MG), VALPHA(MG), S(MG,3), A(MA,MG),              LDETC5
         1 AINEQ(MINEQ,MG), RHSNEQ(MINEQ), WORK(MWORK), IWORK(MA),           LDETC6
         2 REG(MREG,MG), VALPCV(MG), G(MG), EXACT(MG),                       LDETC7
         3 CQUAD(MG), SOLBES(MG), PREJ(2), SAVBES(7),                        LDETC8
         4 LBIND(MINEQ), AA(MG,MG), SQRTW(MY), T(MY), Y(MY), YLYFIT(MY)      LDETC9
           CHARACTER IHOLER(6), ISTAR(2), IFORMT(70), IFORMW(70),
         + IFORMY(70), LA(6,46), ITITLE(80)
           COMMON /CBKOCK/ IFORMT,IFORMW,IFORMY,LA,ITITLE
           COMMON /SBLOCK/ PRECIS, RANGE, SRMIN,                             LDETC1
         1 ALPST(2), GMNMX(2), PLEVEL(2,2), RSVMNX(2,2), RUSER(100),         LDETC2
         2 EXMAX, SRANGE                                                     LDETC3
           COMMON /IBLOCK/ IGRID, IPLRES, IPRINT, IQUAD, IUNIT, IWT,         LDETC4
         1 LINEPG, MIOERR, MQPITR, NEQ, NERFIT, NG, NINTT, NLINF, NORDER,    LDETC5
         2 ICRIT(2),  IPLFIT(2),                                             LDETC6
         3 IUSER(50), LSIGN(4,4), MOMNMX(2), NENDZ(2),                       LDETC7
```

```
   4 NFLAT(4,2), NGL, NGLP1, NIN, NINEQ, NNSGN(2), NOUT, NQPROG(2),
   5 NSGN(4), NY
     COMMON /LBLOCK/ DOMOM, DOUSIN, DOUSNQ, DOUSOU, LAST, NONNEG,
   1 ONLY1, PRWT, PRY, SIMULA,
   2 LUSER(30)
     DATA IHOLER/'L','D','F','E','T','C'/,ISTAR/' ','*'/
     ZERO=0.D0
     DEGFRE=0.
     LSTAR=1
     VAR=SRANGE
     VARREG=SRANGE
     DO 105 J=1,NGL
        SOLUTN(J)=VALPHA(J)
        S(J,3)=ZERO
 105 CONTINUE
     IF (NNNNEQ .EQ. 0)  GO TO 240
     CALL LDP (A,MA,NNNNEQ,NGLE,RHSNEQ,S(1,3),DUB,WORK,IWORK,IERROR,
   1 RANGE)
     GO TO (240,210,220,230),IERROR
 210 CALL ERRMES (1,.TRUE.,IHOLER,NOUT)
 220 DDUM=ALPHA/S(1,1)
5220 FORMAT ('0MAX. ITERATIONS IN NNLS FOR ALPHA/S(1) =',1PE9.2)
     WRITE (NOUT,5220) DDUM
     RETURN
 230 CALL ERRMES (2,.TRUE.,IHOLER,NOUT)
 240 VARREG=0.
     DO 250 ICOL=1,NGLE
        DUB=S(ICOL,2)*S(ICOL,3)
        VARREG=VARREG+(DUB+S(ICOL,2)**2*S(ICOL,1)*(A(ICOL,NGLP1)-
   1 S(ICOL,1)*REG(ICOL,NGLP1)))**2
        DO 255 IROW=1,NGL
           SOLUTN(IROW)=SOLUTN(IROW)+REG(IROW,ICOL)*DUB
 255    CONTINUE
 250 CONTINUE
     CALL CVNEQ (ALPHA,IERROR,NNNNEQ,SOLUTN,
   1 A,AA,AINEQ,DEGFRE,LBIND,MA,MG,MINEQ,MREG,MWORK,NGL,NGLE,
   2 NGLP1,NGLY,NOUT,RANGE,REG,S,VALPCV,WORK)
     CALL GETYLY (SOLUTN,
   1 CQUAD,G,IUNIT,IWT,MWORK,NG,NGL,NLINF,NY,SQRTW,T,WORK,Y,YLYFIT)
     VAR=0.
     DO 310 J=1,NY
        VAR=VAR+YLYFIT(J)**2
 310 CONTINUE
     VARREG=VARREG*ALPHA**2+VAR
     IF (VARZ.LT.VAR .OR. .NOT.FINDVZ .OR. IERROR.NE.1)  GO TO 320
     LSTAR=2
     BTEST=SRANGE
     ALPBES=ZERO
     DEGFRZ=DEGFRE
     VARZ=VAR
 320 PREJ(1)=-1.
     PREJ(2)=-1.
     IF (VARZ.GE.SRANGE .OR. IERROR.NE.1)  GO TO 325
     DDUM=AMAX1(0.,VAR/VARZ-1.)
     DDDUM=AMAX1(0.,FLOAT(NY)-DEGFRZ)
     PREJ(1)=FISHNI(DDUM*DDDUM/DEGFRZ,DEGFRZ,DDDUM,NOUT)
     PREJ(2)=1.
     IF (DEGFRZ-DEGFRE .GT. .1)  PREJ(2)=FISHNI(DDUM*DDDUM/ (DEGFRZ-
   1DEGFRE),DEGFRZ-DEGFRE,DDDUM,NOUT)
5999 FORMAT (' ')
 325 IF (NEWPAG)  WRITE (NOUT,5999)
     IF (.NOT.HEADNG)  GO TO 326
5300 FORMAT (/10X,80A1,10X,'PRELIMINARY UNWEIGHTED ANALYSIS')
     IF (ISTAGE .EQ. 1)  WRITE (NOUT,5300) ITITLE
5302 FORMAT (/10X,80A1)
     IF (ISTAGE .EQ. 2)  WRITE (NOUT,5302) ITITLE
5310 FORMAT (/6X,'ALPHA',4X,'ALPHA/S(1)',5X,
   1 'OBJ. FCTN.',7X,'VARIANCE',6X,'STD. DEV.',4X,'DEG FREEDOM',4X,
   2 'PROB1 TO REJECT',4X,'PROB2 TO REJECT')
     WRITE (NOUT,5310)
5320 FORMAT (1X,A1,1PE9.2,E14.2,2E15.5,E15.3,0PF15.3,2F19.3)
 326 DDUM=ALPHA/S(1,1)
     DDDUM=ALPHA
```

```
      STDDEV=SRANGE                                                      LDETC5
      IF (FLOAT(NY) .GT. DEGFRE) STDDEV=SQRT(VAR/(FLOAT(NY)-DEGFRE))     LDETC6
      IF (PRLDP) WRITE (NOUT,5320) ISTAR(LSTAR),DDDUM,DDUM,VARREG,VAR,   LDETC7
     1 STDDEV,DEGFRE,PREJ                                                 LDETC8
      IF (.NOT.PPLTPR) GO TO 328                                          LDETC9
      DO 327 J=1,NGL                                                      LDETC4
        YLYFIT(J)=SOLUTN(J)                                               LDETC5
  327 CONTINUE                                                            LDETC6
      CALL PLPRIN (G,YLYFIT,EXACT,NG,ONLY1,NOUT,SRANGE,                   LDETC7
     1 NLINF,NG,NGL)                                                      LDETC8
      IF (DOUSOU)  CALL USEROU (G,YLYFIT,EXACT,MG)                        LDETC9
      IF (DDOMOM)  CALL MOMENT (G,YLYFIT,CQUAD,NG, MOMNMX(1),MOMNMX(2),   LDETC0
     1NOUT)                                                               LDETC1
  328 IF (.NOT.SSEARC .OR. VARZ.GE.SRANGE)  GO TO 800                     LDETC2
      TEST=PREJ(IICRIT)-PLEVEL(IICRIT,ISTAGE)                             LDETC3
      IF (ALPHA .LT. ALPBES)   TEST=ABS(TEST)                             LDETC0
      IF (TEST .GE. BTEST)   GO TO 800                                    LDETC1
      SAVBES(1)=ALPHA/S(1,1)                                              LDETC2
      SAVBES(2)=VARREG                                                    LDETC3
      SAVBES(3)=VAR                                                       LDETC4
      SAVBES(4)=STDDEV                                                    LDETC5
      SAVBES(5)=DEGFRE                                                    LDETC6
      SAVBES(6)=PREJ(1)                                                   LDETC7
      SAVBES(7)=PREJ(2)                                                   LDETC8
      BTEST=ABS(TEST)                                                     LDETC9
      ALPBES=ALPHA                                                        LDETC0
      DO 330 J=1,NGL                                                      LDETC1
        SOLBES(J)=SOLUTN(J)                                               LDETC2
  330 CONTINUE                                                            LDETC3
  800 RETURN                                                              LDETC4
      END                                                                 LDETC5
      SUBROUTINE LH1405 (F,M2,M1,E,ME,X)                                  LH4053
      DOUBLE PRECISION DUM, E, F, X                                       LH4054
      DIMENSION F(1), E(ME,M1), X(M1)                                     LH4055
      DO 110 I=1,M2                                                       LH4056
        DUM=F(I)                                                          LH4057
        DO 120 J=1,M1                                                     LH4058
          DUM=DUM-E(I,J)*X(J)                                             LH4059
  120   CONTINUE                                                          LH4050
        F(I)=DUM                                                          LH4051
  110 CONTINUE                                                            LH4052
      RETURN                                                              LH4053
      END                                                                 LH4054
      SUBROUTINE MOMENT (X,Y,CQUAD,N,IDEGMN,IDEGMX,NOUT)                  MOENT4
      DIMENSION X(N), Y(N), CQUAD(N)                                      MOENT5
      DIMENSION AMOM(4,5), PKEND(4)                                       MOENT6
      DATA RMIN/1.E-3/                                                    MOENT7
      NM=MIN0(5,IDEGMX-IDEGMN+1)                                          MOENT8
      IF (NM .LT. 1)  RETURN                                              MOENT9
 5110 FORMAT (/9X,'TOTAL CURVE',8X,3(19X,'PEAK',I2,9X)/                   MOENT0
     1 ' J',3X,'MOMENT(J)',3X,'M(J)/M(J-1)',                              MOENT1
     2 3(11X,'MOMENT(J)',3X,'M(J)/M(J-1)'))                               MOENT2
      WRITE (NOUT,5110) (J,J=1,3)                                         MOENT3
      THRESH=ABS(Y(1))                                                    MOENT4
      DO 110 J=2,N                                                        MOENT5
        THRESH=AMAX1(THRESH,ABS(Y(J)))                                    MOENT6
  110 CONTINUE                                                            MOENT7
      THRESH=RMIN*THRESH                                                  MOENT8
      IPEAK=2                                                             MOENT9
      DO 120 JPEAK=1,4                                                    MOENT0
        DO 120 JDEG=1,NM                                                  MOENT1
          AMOM(JPEAK,JDEG)=0.                                             MOENT2
  120 CONTINUE                                                            MOENT3
      DLAST=Y(2)-Y(1)                                                     MOENT4
      DO 150 J=1,N                                                        MOENT5
        PKEND(IPEAK)=X(J)                                                 MOENT6
        IF (J.EQ.1 .OR. J.EQ.N)  GO TO 160                                MOENT7
        DNEXT=Y(J+1)-Y(J)                                                 MOENT8
        IF (DLAST.LT.-THRESH .AND. DNEXT.GT.THRESH)IPEAK=MIN0(IPEAK+1,4)  MOENT9
        IF (ABS(DNEXT) .GT. THRESH)  DLAST=DNEXT                          MOENT0
  160   IF (IDEGMN.LT.0 .AND. ABS(X(J)).LE.0.)  RETURN                    MOENT1
        TERM=Y(J)*CQUAD(J)                                                MOENT2
        IF(IDEGMN .NE. 0)  TERM=TERM*X(J)**IDEGMN                         MOENT3
```

```
         DO 170 JDEG=1,NM
            AMOM(IPEAK,JDEG)=AMOM(IPEAK,JDEG)+TERM
            IF (JDEG .LT. NM)  TERM=TERM*X(J)
  170    CONTINUE
  150 CONTINUE
      DO 180 JDEG=1,NM
         DO 180 JPEAK=2,IPEAK
            AMOM(1,JDEG)=AMOM(1,JDEG)+AMOM(JPEAK,JDEG)
  180 CONTINUE
 5180 FORMAT (1X,I2,1PE12.4,3E34.4)
      WRITE (NOUT,5180) IDEGMN,(AMOM(J,1),J=1,IPEAK)
      IF (NM .EQ. 1)  GO TO 300
      J=IDEGMN
      DO 210 JDEG=2,NM
         J=J+1
         DO 220 JPEAK=1,IPEAK
            IF (ABS(AMOM(JPEAK,JDEG-1)) .GT. 0.)  AMOM(JPEAK,JDEG-1)=
     1      AMOM(JPEAK,JDEG)/AMOM(JPEAK,JDEG-1)
  220    CONTINUE
 5220    FORMAT (1X,I2,1PE12.4,E14.4,3(E20.4,E14.4))
         WRITE (NOUT,5220) J,(AMOM(JPEAK,JDEG),AMOM(JPEAK,JDEG-1),
     1   JPEAK=1,IPEAK)
  210 CONTINUE
 5230 FORMAT (' CURRENT PEAK ENDS AND NEXT PEAK BEGINS AT',
     1 1PE11.3,10X,2(16X,E11.3,7X))
  300 IF (IPEAK .GT. 2)  WRITE (NOUT,5230)(PKEND(J),J=2,IPEAK)
      RETURN
      END
      SUBROUTINE NNLS (A,MDA,M,N,B,X,RNORM,W,ZZ,INDEX,MODE,RANGE)
      DOUBLE PRECISION A, ABS, ALPHA, ASAVE, B, CC, DIFF, DUMMY,
     1 FACTOR, RANGE, RNORM, SM, SQRT, SS, T, TWO, UNORM, UP, W,
     2 WMAX, X, ZERO, ZTEST, ZZ
      DIMENSION A(MDA,N), B(1), X(1), W(1), ZZ(1)
      INTEGER INDEX(N)
      ABS(T)=DABS(T)
      SQRT(T)=DSQRT(T)
      ZERO=0.D0
      TWO=2.D0
      FACTOR=1.D-4
      MODE=1
      IF (M.GT.0.AND.N.GT.0)  GO TO 10
      MODE=2
      RETURN
   10 ITER=0
      ITMAX=3*N
         DO 20 I=1,N
         X(I)=ZERO
   20    INDEX(I)=I
      IZ2=N
      IZ1=1
      NSETP=0
      NPP1=1
   30 CONTINUE
      IF (IZ1.GT.IZ2.OR.NSETP.GE.M)  GO TO 350
         DO 50 IZ=IZ1,IZ2
         J=INDEX(IZ)
         SM=ZERO
            DO 40 L=NPP1,M
   40       SM=SM+A(L,J)*B(L)
   50    W(J)=SM
   60 WMAX=ZERO
         DO 70 IZ=IZ1,IZ2
         J=INDEX(IZ)
         IF (W(J).LE.WMAX)  GO TO 70
         WMAX=W(J)
         IZMAX=IZ
   70    CONTINUE
      IF (WMAX)  350,350,80
   80 IZ=IZMAX
      J=INDEX(IZ)
      ASAVE=A(NPP1,J)
      CALL H12 (1,NPP1,NPP1+1,M,A(1,J),1,UP,DUMMY,1,1,0,RANGE)
      UNORM=ZERO
```

```
         IF (NSETP.EQ.0)  GO TO 100                                        NNLS 2
             DO 90 L=1,NSETP                                               NNLS 3
90           UNORM=UNORM+A(L,J)**2                                         NNLS 4
         UNORM=SQRT(UNORM)                                                 NNLS 5
100      IF (DIFF(UNORM+ABS(A(NPP1,J))*FACTOR,UNORM))  130,130,110         NNLS 6
110          DO 120 L=1,M                                                  NNLS 1
120          ZZ(L)=B(L)                                                    NNLS 2
         CALL H12 (2,NPP1,NPP1+1,M,A(1,J),1,UP,ZZ,1,1,1,RANGE)             NNLS 3
         ZTEST=ZZ(NPP1)/A(NPP1,J)                                          NNLS 4
         IF (ZTEST)   130,130,140                                          NNLS 0
130      A(NPP1,J)=ASAVE                                                   NNLS 4
         W(J)=ZERO                                                         NNLS 5
         GO TO 60                                                          NNLS 6
140          DO 150 L=1,M                                                  NNLS 3
150          B(L)=ZZ(L)                                                    NNLS 4
         INDEX(IZ)=INDEX(IZ1)                                              NNLS 6
         INDEX(IZ1)=J                                                      NNLS 7
         IZ1=IZ1+1                                                         NNLS 8
         NSETP=NPP1                                                        NNLS 9
         NPP1=NPP1+1                                                       NNLS 0
         IF (IZ1.GT.IZ2)  GO TO 170                                        NNLS 2
             DO 160 JZ=IZ1,IZ2                                             NNLS 3
             JJ=INDEX(JZ)                                                  NNLS 4
160          CALL H12 (2,NSETP,NPP1,M,A(1,J),1,UP,A(1,JJ),1,MDA,1,RANGE)   NNLS 5
170      CONTINUE                                                          NNLS 6
         IF (NSETP.EQ.M)  GO TO 190                                        NNLS 8
             DO 180 L=NPP1,M                                               NNLS 9
180          A(L,J)=ZERO                                                   NNLS 0
190      CONTINUE                                                          NNLS 1
         W(J)=ZERO                                                         NNLS 3
         ASSIGN 200 TO NEXT                                                NNLS 6
         GO TO 400                                                         NNLS 7
200      CONTINUE                                                          NNLS 8
210      ITER=ITER+1                                                       NNLS 4
         IF (ITER.LE.ITMAX)  GO TO 220                                     NNLS 5
         MODE=3                                                            NNLS 6
         GO TO 350                                                         NNLS 7
220      CONTINUE                                                          NNLS 8
         ALPHA=TWO                                                         NNLS 3
             DO 240 IP=1,NSETP                                             NNLS 4
             L=INDEX(IP)                                                   NNLS 5
             IF (ZZ(IP))   230,230,240                                     NNLS 6
230          T=-X(L)/(ZZ(IP)-X(L))                                         NNLS 8
             IF (ALPHA.LE.T)  GO TO 240                                    NNLS 9
             ALPHA=T                                                       NNLS 0
             JJ=IP                                                         NNLS 1
240          CONTINUE                                                      NNLS 2
         IF (ALPHA.EQ.TWO)  GO TO 330                                      NNLS 7
             DO 250 IP=1,NSETP                                             NNLS 2
             L=INDEX(IP)                                                   NNLS 3
250          X(L)=X(L)+ALPHA*(ZZ(IP)-X(L))                                 NNLS 4
         I=INDEX(JJ)                                                       NNLS 9
260      X(I)=ZERO                                                         NNLS 0
         IF (JJ.EQ.NSETP)  GO TO 290                                       NNLS 2
         JJ=JJ+1                                                           NNLS 3
             DO 280 J=JJ,NSETP                                             NNLS 4
             II=INDEX(J)                                                   NNLS 5
             INDEX(J-1)=II                                                 NNLS 6
             CALL G1 (A(J-1,II),A(J,II),CC,SS,A(J-1,II))                   NNLS 7
             A(J,II)=ZERO                                                  NNLS 8
                 DO 270 L=1,N                                              NNLS 9
                 IF (L.NE.II)  CALL G2 (CC,SS,A(J-1,L),A(J,L))             NNLS 0
270              CONTINUE                                                  NNLS 1
280          CALL G2 (CC,SS,B(J-1),B(J))                                   NNLS 2
290      NPP1=NSETP                                                        NNLS 3
         NSETP=NSETP-1                                                     NNLS 4
         IZ1=IZ1-1                                                         NNLS 5
         INDEX(IZ1)=I                                                      NNLS 6
             DO 300 JJ=1,NSETP                                             NNLS 4
             I=INDEX(JJ)                                                   NNLS 5
             IF (X(I))  260,260,300                                        NNLS 6
300          CONTINUE                                                      NNLS 7
             DO 310 I=1,M                                                  NNLS 1
```

```
310       ZZ(I)=B(I)                                                NNLS 2
      ASSIGN 320 TO NEXT                                            NNLS 3
      GO TO 400                                                     NNLS 4
320   CONTINUE                                                      NNLS 5
      GO TO 210                                                     NNLS 6
330       DO 340 IP=1,NSETP                                         NNLS 9
          I=INDEX(IP)                                               NNLS 0
340       X(I)=ZZ(IP)                                               NNLS 1
      GO TO 30                                                      NNLS 3
350   SM=ZERO                                                       NNLS 0
      IF (NPP1.GT.M)  GO TO 370                                     NNLS 1
          DO 360 I=NPP1,M                                           NNLS 2
360       SM=SM+B(I)**2                                             NNLS 3
      GO TO 390                                                     NNLS 4
370       DO 380 J=1,N                                              NNLS 5
380       W(J)=ZERO                                                 NNLS 6
390   RNORM=SQRT(SM)                                                NNLS 7
      RETURN                                                        NNLS 8
400       DO 430 L=1,NSETP                                          NNLS 3
          IP=NSETP+1-L                                              NNLS 4
          IF (L.EQ.1)  GO TO 420                                    NNLS 5
              DO 410 II=1,IP                                        NNLS 6
                                                                    NNLS 7
410           ZZ(II)=ZZ(II)-A(II,JJ)*ZZ(IP+1)                       NNLS 8
420       JJ=INDEX(IP)                                              NNLS 9
430       ZZ(IP)=ZZ(IP)/A(IP,JJ)                                    NNLS 0
      GO TO NEXT, (200,320)                                         NNLS 1
      END
      FUNCTION PGAUSS (X)                                           PGUSS6
      AX=ABS(X)                                                     PGUSS7
      PGAUSS=1.+AX*(.196854+AX*(.115194+AX*(3.44E-4+AX*.019527)))   PGUSS8
      PGAUSS=1./PGAUSS**2                                           PGUSS9

PGAUSS=.5*PGAUSS**2                                           PGUSS0
      IF (X .GT. 0.)  PGAUSS=1.-PGAUSS                              PGUSS1
      RETURN                                                        PGUSS2
      END                                                           PGUSS3
      SUBROUTINE PLPRIN (X,Y1,Y2,N,ONLY1,NOUT,SRANGE,NLINF,NG,MY1)  PLRIN6
      LOGICAL ONLY1                                                 PLRIN7
      DIMENSION X(N), Y1(MY1), Y2(N)                                PLRIN8
      CHARACTER ICHAR(4), IH(108)
      DATA ICHAR/' ','X','O','*'/                                   PLRIN9
C
C     PRINT OUT DATA AND FIT TO FILE 'datafit' TO USE FOR PLOTTING
C
C
      IF (.NOT. ONLY1) THEN
          IJK=N/2
          IANG=IJK
          IF(IJK.GT.256) THEN
              IANG=IJK
              IJK=256
          ENDIF
          OPEN(4,FILE='data',STATUS='NEW')
          OPEN(3,FILE='fit',STATUS='NEW')
          WRITE(4,*) IJK
          WRITE(3,*) IJK
          WRITE(4,500) (X(J),Y2(J),J=1,IJK)
          WRITE(3,500) (X(J),Y1(J),J=1,IJK)
500       FORMAT(E10.3,1X,E10.3)
          CLOSE(4)
          CLOSE(3)
          OPEN(4,FILE='data1',STATUS='NEW')
          OPEN(3,FILE='fit1',STATUS='NEW')
          WRITE(4,*) IJK
          WRITE(3,*) IJK
          WRITE(4,500) (X(J),Y2(J),J=IANG+1,IANG+IJK)
          WRITE(3,500) (X(J),Y1(J),J=IANG+1,IANG+IJK)
          CLOSE(4)
          CLOSE(3)
      ENDIF                                                         PLRIN0
      YMIN=SRANGE                                                   PLRIN1
      YMAX=-SRANGE                                                  PLRIN2
      DO 120 J=1,N                                                  PLRIN3
          YMIN=AMIN1(YMIN,Y1(J))                                    PLRIN4
          YMAX=AMAX1(YMAX,Y1(J))
```

```
          IF (ONLY1)  GO TO 120                                 PLRIN5
          YMIN=AMIN1(YMIN,Y2(J))                                PLRIN6
          YMAX=AMAX1(YMAX,Y2(J))                                PLRIN7
  120 CONTINUE                                                  PLRIN8
      DUM=YMAX-YMIN                                             PLRIN9
      IF (DUM .LE. 0.)  DUM=1.                                  PLRINO
      R=107.99/DUM                                              PLRIN1
      WRITE (NOUT,5120)                                         PLRIN2
 5120 FORMAT (/4X,'ORDINATE',3X,'ABSCISSA')                     PLRIN3
      L2=1                                                      PLRIN4
      DO 150 J=1,N                                              PLRIN5
         DO 155 L1=1,108                                        PLRIN6
            IH(L1)=ICHAR(1)                                     PLRIN7
  155    CONTINUE                                               PLRIN8
         L1=INT((Y1(J)-YMIN)*R)+1                               PLRIN9
         IH(L1)=ICHAR(2)                                        PLRINO
         IF (ONLY1)  GO TO 160                                  PLRIN1
         L2=INT((Y2(J)-YMIN)*R)+1                               PLRIN2
         IH(L2)=ICHAR(3)                                        PLRIN3
         IF (L1 .EQ. L2)  IH(L2)=ICHAR(4)                       PLRIN4
  160    WRITE (NOUT,5160) Y1(J),X(J),IH                        PLRIN5
 5160    FORMAT (1X,1P2E11.3,108A1)                             PLRIN6
  150 CONTINUE                                                  PLRIN7
      IF (NLINF .LE. 0)  GO TO 800                              PLRIN8
      L2=N5+1                                                   PLRIN9
 5200 FORMAT ('OLINEAR COEFFICIENTS =',1P8E13.4/(22X,8E13.4))   PLRINO
      WRITE (NOUT,5200) (Y1(J),J=L2,MY1)                        PLRIN1
  800 RETURN                                                    PLRIN2
      END                                                       PLRIN3
      SUBROUTINE PLRES (YLYFIT,NMAX,N,PRUNS,RALPS1,NOUT,LINEPG,ITITLE)  PLRES6
      DIMENSION YLYFIT(NMAX), LCHARJ(20),LABEL(6), BOUND(21)    PLRES7
      CHARACTER IHOLER(6), JCHAR(8), LINE1(20), LINE(131)
     + , ITITLE(80)
      DATA JCHAR/'X','-','U','L',' ','O','-','+'/,              PLRES9
    1 IHOLER/'P','L','R','E','S',' '/, MPAGE/30/                PLRES0
      IF (LINEPG .GE. 17)  GO TO 100                            PLRES1
      CALL ERRMES (1,.FALSE.,IHOLER,NOUT)                       PLRES2
      RETURN                                                    PLRES3
  100 MPLOT=(LINEPG-3)/16                                       PLRES4
      MLINE=MIN0(20,(LINEPG-3)/MPLOT-3)                         PLRES5
      RMIN=YLYFIT(1)                                            PLRES6
      RMAX=YLYFIT(1)                                            PLRES7
      DO 110 J=2,N                                              PLRES8
      RMIN=AMIN1(RMIN,YLYFIT(J))                                PLRES9
  110 RMAX=AMAX1(RMAX,YLYFIT(J))                                PLRES0
 5200 FORMAT (' ',9X,80A1//                                     PLRES1
    1 ' PLOT OF WEIGHTED RESIDUALS (FOR ALPHA/S(1) =',          PLRES2
    2 1PE9.2,') MAX = U =',E8.1,5X,'MIN = L =',E8.1,9X,         PLRES3
    3 'RANDOM RUNS PROB. =',0PF7.4)                             PLRES4
      WRITE (NOUT,5200) ITITLE,RALPS1,RMAX,RMIN,PRUNS           PLRES5
      DELTA=(RMAX-RMIN)/FLOAT(MLINE-1)                          PLRES6
      BOUND(1)=RMAX+.5*DELTA                                    PLRES7
      K=MLINE+1                                                 PLRES8
      DO 120 J=2,K                                              PLRES9
      BOUND(J)=BOUND(J-1)-DELTA                                 PLRES0
  120 IF (BOUND(J)*BOUND(J-1) .LT. 0.)  JAXIS=J-1               PLRES1
      LABEL(1)=-110                                             PLRES2
      DO 130 J=2,6                                              PLRES3
  130 LABEL(J)=LABEL(J-1)+20                                    PLRES4
      K=MLINE-1                                                 PLRES5
      DO 140 J=2,K                                              PLRES6
      LINE1(J)=JCHAR(5)                                         PLRES7
  140 LCHARJ(J)=5                                               PLRES8
      LINE1(1)=JCHAR(3)                                         PLRES9
      LINE1(JAXIS)=JCHAR(6)                                     PLRES0
      LINE1(MLINE)=JCHAR(4)                                     PLRES1
      LCHARJ(1)=7                                               PLRES2
      LCHARJ(JAXIS)=2                                           PLRES3
      LCHARJ(MLINE)=7                                           PLRES4
      NPOINT=0                                                  PLRES5
      DO 200 NPAGE=1,MPAGE                                      PLRES6
      IF (NPAGE .GT. 1) WRITE( NOUT,5999)                       PLRES7
```

```
5999 FORMAT ('1')                                                           PLRES8
     DO 210 NPLOT=1,MPLOT                                                   PLRES9
5001 FORMAT (' ')                                                           PLRES0
     WRITE (NOUT,5001)                                                      PLRES1
     NST=NPOINT+1                                                           PLRES2
     NEND=NPOINT+130                                                        PLRES3
     NPOINT=NEND                                                            PLRES4
     NLIM=MINO(NEND,N)                                                      PLRES5
     DO 220 NLINE=1,MLINE                                                   PLRES6
     LCHAR=LCHARJ(NLINE)                                                    PLRES7
     LINE(1)=LINE1(NLINE)                                                   PLRES8
     BMAX=BOUND(NLINE)                                                      PLRES9
     BMIN=BOUND(NLINE+1)                                                    PLRES0
     K=1                                                                    PLRES1
     DO 230 J=NST,NLIM                                                      PLRES2
     K=K+1                                                                  PLRES3
     LINE(K)=JCHAR(LCHAR)                                                   PLRES4
     IF (YLYFIT(J).LT.BMAX .AND. YLYFIT(J).GE.BMIN)  LINE(K)=JCHAR(1)       PLRES5
 230 CONTINUE                                                               PLRES6
     K=NLIM-NST+2                                                           PLRES7
     IF (NLINE.NE.1 .AND. NLINE.NE.MLINE)  GO TO 235                        PLRES8
     DO 232 J=11,K,10                                                       PLRES9
 232 IF (LINE(J) .NE. JCHAR(1))  LINE(J)=JCHAR(8)                           PLRES0
5230 FORMAT (1X,A1,130A1)                                                   PLRES1
 235 WRITE (  NOUT,5230) (LINE(J),J=1,K)                                    PLRES2
 220 CONTINUE                                                               PLRES3
     DO 240 J=1,6                                                           PLRES4
 240 LABEL(J)=LABEL(J)+130                                                  PLRES5
5240 FORMAT (3X,6(16X,I4)/)                                                 PLRES6
     WRITE (  NOUT,5240) LABEL                                              PLRES7
     IF (NLIM .EQ. N)  RETURN                                               PLRES8
 210 CONTINUE                                                               PLRES9
 200 CONTINUE                                                               PLRES0
     CALL ERRMES (2,.FALSE.,IHOLER,NOUT)                                    PLRES1
     RETURN                                                                 PLRES2
     END                                                                    PLRES3
     SUBROUTINE QRBD (IPASS,Q,E,NN,V,MDV,NRV,C,MDC,NCC,RANGE)               QRBD 7
     DOUBLE PRECISION ABS, AMAX1, C, CS, DIFF, DNORM, E, F,                 QRBD 8
    1 G, H,                                                                 QRBD 9
    2 ONE, Q, RANGE, SN, SQRT, SQRTRG, T, TWO, V, X, Y, Z, ZERO             QRBD 0
     LOGICAL WNTV ,HAVERS,FAIL                                              QRBD 1
     DIMENSION Q(NN),E(NN),V(MDV,1),C(MDC,1)                                QRBD 2
     AMAX1(ZERO,ONE)=DMAX1(ZERO,ONE)                                        QRBD 3
     ABS(ONE)=DABS(ONE)                                                     QRBD 4
     SQRT(ONE)=DSQRT(ONE)                                                   QRBD 5
     ZERO=0.D0                                                              QRBD 7
     ONE=1.D0                                                               QRBD 9
     TWO=2.D0                                                               QRBD 1
     SQRTRG=SQRT(RANGE)                                                     QRBD 2
     N=NN                                                                   QRBD 4
     IPASS=1                                                                QRBD 5
     IF (N.LE.0)  RETURN                                                    QRBD 6
     N10=10*N                                                               QRBD 7
     WNTV=NRV.GT.0                                                          QRBD 8
     HAVERS=NCC.GT.0                                                        QRBD 9
     FAIL=.FALSE.                                                           QRBD 0
     NQRS=0                                                                 QRBD 1
     E(1)=ZERO                                                              QRBD 2
     DNORM=ZERO                                                             QRBD 3
         DO 10 J=1,N                                                        QRBD 4
  10     DNORM=AMAX1(ABS(Q(J))+ABS(E(J)),DNORM)                             QRBD 5
         DO 200 KK=1,N                                                      QRBD 6
         K=N+1-KK                                                           QRBD 7
  20      IF(K.EQ.1)  GO TO 50                                              QRBD 1
          IF(DIFF(DNORM+Q(K),DNORM))  50,25,50                              QRBD 2
  25      CS=ZERO                                                           QRBD 7
          SN=-ONE                                                           QRBD 8
              DO 40 II=2,K                                                  QRBD 9
              I=K+1-II                                                      QRBD 0
              F=-SN*E(I+1)                                                  QRBD 1
              E(I+1)=CS*E(I+1)                                              QRBD 2
              CALL G1 (Q(I),F,CS,SN,Q(I))                                   QRBD 3
              IF (.NOT.WNTV)  GO TO 40                                      QRBD 6
```

```
                DO 30 J=1,NRV                          QRBD 7
30              CALL G2 (CS,SN,V(J,I),V(J,K))          QRBD 8
40          CONTINUE                                   QRBD 1
50          DO 60 LL=1,K                               QRBD 6
            L=K+1-LL                                   QRBD 7
            IF(DIFF(DNORM+E(L),DNORM))  55,100,55     QRBD 8
55          IF(DIFF(DNORM+Q(L-1),DNORM))  60,70,60    QRBD 9
60          CONTINUE                                   QRBD 0
        GO TO 100                                      QRBD 3
70      CS=ZERO                                        QRBD 6
        SN=-ONE                                        QRBD 7
            DO 90 I=L,K                                QRBD 8
            F=-SN*E(I)                                 QRBD 9
            E(I)=CS*E(I)                               QRBD 0
            IF(DIFF(DNORM+F,DNORM))  75,100,75        QRBD 1
75          CALL G1 (Q(I),F,CS,SN,Q(I))                QRBD 2
            IF (.NOT.HAVERS)  GO TO 90                 QRBD 3
                DO 80 J=1,NCC                          QRBD 4
80              CALL G2 (CS,SN,C(I,J),C(L-1,J))        QRBD 5
90          CONTINUE                                   QRBD 6
100     Z=Q(K)                                         QRBD 9
        IF (L.EQ.K)  GO TO 170                         QRBD 0
        X=Q(L)                                         QRBD 3
        Y=Q(K-1)                                       QRBD 4
        G=E(K-1)                                       QRBD 5
        H=E(K)                                         QRBD 6
        F=((Y-Z)*(Y+Z)+(G-H)*(G+H))/(TWO*H*Y)          QRBD 7
        G=ABS(F)                                       QRBD 1
        IF (G .LT. SQRTRG)  G=SQRT(ONE+G**2)           QRBD 2
        IF (F.LT.ZERO)  GO TO 110                      QRBD 3
        T=F+G                                          QRBD 4
        GO TO 120                                      QRBD 5
110     T=F-G                                          QRBD 6
120     F=((X-Z)*(X+Z)+H*(Y/T-H))/X                    QRBD 7
        CS=ONE                                         QRBD 0
        SN=ONE                                         QRBD 1
        LP1=L+1                                        QRBD 2
            DO 160 I=LP1,K                             QRBD 3
            G=E(I)                                     QRBD 4
            Y=Q(I)                                     QRBD 5
            H=SN*G                                     QRBD 6
            G=CS*G                                     QRBD 7
            CALL G1 (F,H,CS,SN,E(I-1))                 QRBD 8
            F=X*CS+G*SN                                QRBD 9
            G=-X*SN+G*CS                               QRBD 0
            H=Y*SN                                     QRBD 1
            Y=Y*CS                                     QRBD 2
            IF (.NOT.WNTV)  GO TO 140                  QRBD 3
                DO 130 J=1,NRV                         QRBD 6
130             CALL G2 (CS,SN,V(J,I-1),V(J,I))        QRBD 7
140         CALL G1 (F,H,CS,SN,Q(I-1))                 QRBD 8
            F=CS*G+SN*Y                                QRBD 9
            X=-SN*G+CS*Y                               QRBD 0
            IF (.NOT.HAVERS)  GO TO 160                QRBD 1
                DO 150 J=1,NCC                         QRBD 2
150             CALL G2 (CS,SN,C(I-1,J),C(I,J))        QRBD 3
160         CONTINUE                                   QRBD 7
        E(L)=ZERO                                      QRBD 8
        E(K)=F                                         QRBD 9
        Q(K)=X                                         QRBD 0
        NQRS=NQRS+1                                    QRBD 1
        IF (NQRS.LE.N10)  GO TO 20                     QRBD 2
        FAIL=.TRUE.                                    QRBD 5
170     IF (Z.GE.ZERO)  GO TO 190                      QRBD 8
        Q(K)=-Z                                        QRBD 9
        IF (.NOT.WNTV)  GO TO 190                      QRBD 0
            DO 180 J=1,NRV                             QRBD 1
180         V(J,K)=-V(J,K)                             QRBD 2
190     CONTINUE                                       QRBD 3
200     CONTINUE                                       QRBD 6
    IF (N.EQ.1)  RETURN                                QRBD 7
        DO 210 I=2,N                                   QRBD 8
        IF (Q(I).GT.Q(I-1))  GO TO 220                 QRBD 9
```

```
 210        CONTINUE                                            QRBD 0
       IF (FAIL) IPASS=2                                         QRBD 1
       RETURN                                                    QRBD 2
 220        DO 270 I=2,N                                         QRBD 5
            T=Q(I-1)                                             QRBD 6
            K=I-1                                                QRBD 7
               DO 230 J=I,N                                      QRBD 8
               IF (T.GE.Q(J))  GO TO 230                         QRBD 9
               T=Q(J)                                            QRBD 0
               K=J                                               QRBD 1
 230           CONTINUE                                          QRBD 2
            IF (K.EQ.I-1) GO TO 270                              QRBD 3
            Q(K)=Q(I-1)                                          QRBD 4
            Q(I-1)=T                                             QRBD 5
            IF (.NOT.HAVERS) GO TO 250                           QRBD 6
               DO 240 J=1,NCC                                    QRBD 7
               T=C(I-1,J)                                        QRBD 8
               C(I-1,J)=C(K,J)                                   QRBD 9
 240           C(K,J)=T                                          QRBD 0
 250        IF (.NOT.WNTV) GO TO 270                             QRBD 1
               DO 260 J=1,NRV                                    QRBD 2
               T=V(J,I-1)                                        QRBD 3
               V(J,I-1)=V(J,K)                                   QRBD 4
 260           V(J,K)=T                                          QRBD 5
 270        CONTINUE                                             QRBD 6
       IF (FAIL) IPASS=2                                         QRBD 9
       RETURN                                                    QRBD 0
       END                                                       QRBD 1
       FUNCTION RANDOM(DIX)                                      RADOM9
       DOUBLE PRECISION A,P,DIX,B15,B16,XHI,XALO,LEFTLO,FHI,K    RADOM5
       DATA A/16807.D0/,B15/32768.D0/,B16/65536.D0/,P/2147483647.D0/  RADOM8
       XHI = DIX / B16                                           RADOM1
       XHI = XHI - DMOD(XHI,1.D0)                                RADOM2
       XALO=(DIX-XHI*B16)*A                                      RADOM4
       LEFTLO = XALO/B16                                         RADOM6
       LEFTLO = LEFTLO - DMOD(LEFTLO,1.D0)                       RADOM7
       FHI = XHI*A + LEFTLO                                      RADOM9
       K = FHI/B15                                               RADOM1
       K = K - DMOD(K,1.D0)                                      RADOM2
       DIX = (((XALO-LEFTLO*B16) - P) + (FHI-K*B15)*B16) + K     RADOM5
       IF (DIX .LT. 0.D0)  DIX = DIX + P                         RADOM7
       RANDOM=DIX*4.656612875D-10                                RADOM9
       RETURN                                                    RADOM0
       END                                                       RADOM1
       SUBROUTINE READYT (MY,NIDERR,SQRTW,T,Y)
       DOUBLE PRECISION PRECIS, RANGE                            REDYT9
                                                                 REDYT0
       LOGICAL DOMOM, DOUSIN, DOUSNQ, DOUSOU, LAST, NONNEG, ONLY1, PRWT,  REDYT1
      1 PRY, SIMULA, LUSER                                       REDYT2
       DIMENSION SQRTW(MY), T(MY), Y(MY)                         REDYT3
       CHARACTER IHOLER(6), LAA(6,2), LIN(6),IFORMT(70), IFORMW(70)
      + , IFORMY(70), LA(6,46), ITITLE(80)
       COMMON /CBLOCK/ IFORMT, IFORMW, IFORMY, LA, ITITLE
       COMMON /SBLOCK/ PRECIS, RANGE, SRMIN,                     REDYT5
      1 ALPST(2), GMNMX(2), PLEVEL(2,2), RSVMNX(2,2), RUSER(100),  REDYT6
      2 EXMAX, SRANGE                                            REDYT7
       COMMON /IBLOCK/ IGRID, IPLRES, IPRINT, IQUAD, IUNIT, IWT,  REDYT8
      1 LINEPG, MIDERR, MQPITR, NEQ, NERFIT, NG, NINTT, NLINF, NORDER,  REDYT9
      2 ICRIT(2), IPLFIT(2),                                     REDYT0
      3  IUSER(50), LSIGN(4,4), MOMNMX(2), NENDZ(2),             REDYT1
      4 NFLAT(4,2), NGL, NGLP1, NIN, NINEQ, NNSGN(2), NOUT, NQPROG(2),  REDYT2
      5 NSGN(4), NY                                              REDYT3
       COMMON /LBLOCK/ DOMOM, DOUSIN, DOUSNQ, DOUSOU, LAST, NONNEG,  REDYT4
      1 ONLY1, PRWT, PRY, SIMULA,                                REDYT5
      2 LUSER(30)                                                REDYT6
       DATA IHOLER/'R','E','A','D','Y','T'/, LAA/                REDYT7
      1 'N','S','T','E','N','D','N','Y',' ',' ',' ',' '/         REDYT8
       IF (NINTT .LE. 0) GO TO 200                               REDYT9
       NY=0                                                      REDYT3
       DO 110 J=1,NINTT                                          REDYT4
5110   FORMAT (1X,6A1,I8,2E15.7)                                 REDYT5
       READ (NIN,5110) LIN,NT,TSTART,TEND                        REDYT6
       WRITE (NOUT,5110) LIN,NT,TSTART,TEND                      REDYT7
       DO 120 K=1,6                                              REDYT8
```

```
      IF (LIN(K) .NE. LAA(K,1))  GO TO 130
120 CONTINUE
      GO TO 140
130 CALL ERRMES (1,.FALSE.,IHOLER,NOUT)
      GO TO 190
140 IF (NT.GE.2 .AND. NT+NY.LE.MY)  GO TO 150
      CALL ERRMES (2,.FALSE.,IHOLER,NOUT)
      GO TO 190
150 DUM=(TEND-TSTART)/FLOAT(NT-1)
      NY=NY+1
      T(NY)=TSTART
      DO 160 K=2,NT
      NY=NY+1
160 T(NY)=T(NY-1)+DUM
      GO TO 110
190 NIOERR=NIOERR+1
      IF (NIOERR .GE. MIOERR)  STOP
110 CONTINUE
      GO TO 300
200 READ (NIN,5110) LIN,NY
      WRITE (NOUT,5110) LIN,NY
      DO 210 K=1,6
        IF (LIN(K) .NE. LAA(K,2))  GO TO 220
210 CONTINUE
      GO TO 230
220 CALL ERRMES (3,.FALSE.,IHOLER,NOUT)
      GO TO 235
230 IF (NY .LE. MY)  GO TO 240
      CALL ERRMES (4,.FALSE.,IHOLER,NOUT)
235 NIOERR=NIOERR+1
      RETURN
240 READ (NIN,6007) (T(J),J=1,NY)
300  IF(.NOT.SIMULA) READ (NIN,6008) (Y(J),J=1,NY)
6007   FORMAT(5E15.6)
6008   FORMAT(4E17.11)
      IF (IWT .EQ. 4)  GO TO 420
      DO 410 J=1,NY
      SQRTW(J)=1.
410 CONTINUE
420 IF (IWT .EQ. 4)  READ (NIN,6007) (SQRTW(J),J=1,NY)
      IF (DOUSIN)  CALL USERIN (T,Y,SQRTW,MY)
      DO 430 J=1,NY
      IF (SQRTW(J) .GE. 0.)  GO TO 440
      CALL ERRMES (5,.FALSE.,IHOLER,NOUT)
5440 FORMAT (1X,1P10E13.5)
      WRITE (NOUT,5440) (SQRTW(K),K=1,NY)
      NIOERR=NIOERR+1
      GO TO 800
440 SQRTW(J)=SQRT(SQRTW(J))
430 CONTINUE
800 RETURN
      END
      SUBROUTINE RGAUSS (X1,X2,TWOPI,DIX)
      DOUBLE PRECISION DIX
      X1=SQRT(-2.*ALOG(RANDOM(DIX)))
      DUM=TWOPI*RANDOM(DIX)
      X2=X1*SIN(DUM)
      X1=X1*COS(DUM)
      RETURN
      END
      SUBROUTINE RUNRES (ILEVEL,SOL,NEWPAG,RALPS1,
     1 CQUAD,G,IPLFIT,IPLRES,ISTAGE,ITITLE,IUNIT,IWT,LINEPG,MWORK,NG,
     2 NGL,NLINF,NOUT,NY,SQRTW,SRANGE,T,WORK,Y,YLYFIT)
      DOUBLE PRECISION  SOL, WORK
      LOGICAL NEWPAG
      CHARACTER ITITLE(80)
      DIMENSION SOL(NGL), WORK(MWORK), SQRTW(NY), CQUAD(NG), G(NG),
     1 T(NY), Y(NY), YLYFIT(NY),   IPLFIT(2)
      PRUNS=GETPRU (SOL,
     1 CQUAD,G,IUNIT,IWT,MWORK,NG,NGL,NLINF,NY,SQRTW,T,WORK,
     2 Y,YLYFIT)
      IF (ILEVEL.LE.IPLRES)  GO TO 150
```

```
5100 FORMAT ('1',9X,80A1)                                                      RURES4
     IF (NEWPAG)  WRITE (NOUT,5100) ITITLE                                     RURES5
5110 FORMAT ('0(FOR ALPHA/S(1) =',1PE9.2,                                      RURES6
    1 ') PROB. THAT A RANDOMLY CHOSEN ORDER OF SIGNS WOULD HAVE',              RURES7
    2 ' NO MORE RUNS THAN THE RESIDUALS =',0PF7.4)                             RURES8
     WRITE (NOUT,5110) RALPS1,PRUNS                                            RURES9
     GO TO 200                                                                 RURES0
 150 CALL PLRES (YLYFIT,NY,NY,PRUNS,RALPS1,NOUT,LINEPG,ITITLE)
 200 IF (ILEVEL .GT. IPLFIT(ISTAGE)) GO TO 800
     DO 210 J=1,NY
     YLYFIT(J)=Y(J)-YLYFIT(J)/SQRTW(J)
 210 CONTINUE
5210 FORMAT (//'0PLOT OF DATA (O) AND FIT TO DATA (X).',
    1 '  ORDINATES LISTED ARE FIT VALUES.')
     WRITE (NOUT,5210)                                                         RURES1
     CALL PLPRIN (T,YLYFIT,Y,NY,.FALSE.,NOUT,SRANGE,0,0,NY)                    RURES2
     DO 220 J=1,NY                                                             RURES6
        YLYFIT(J)=(Y(J)-YLYFIT(J))*SQRTW(J)                                    RURES7
 220 CONTINUE                                                                  RURES8
 800 RETURN                                                                    RURES9
     END                                                                       RURES0
     SUBROUTINE SEQACC (                                                       SEACC3
    1 A,CQUAD,G,ISTAGE,IUNIT,IWT,MA,MG,NG,NGL,NGLP1,NLINF,NY,                  SEACC4
    2 RANGE,SQRTW,T,Y)                                                         SEACC5
     DOUBLE PRECISION A, RANGE, RHO, ZERO                                      SEACC6
     DIMENSION A(MA,MG), T(NY), Y(NY), SQRTW(NY), G(NG), CQUAD(NG)             SEACC7
     ZERO=0.D0                                                                 SEACC9
     L=0                                                                       SEACC0
     NGL=NG+NLINF                                                              SEACC1
     NGLP1=NGL+1                                                               SEACC2
     DO 200 IT=1,NY                                                            SEACC3
        IP=L+1                                                                 SEACC4
        IIT=IT                                                                 SEACC5
        CALL GETROW (IIT,A(IP,1),.TRUE.,ISTAGE,MA,IUNIT,                       SEACC6
    1   SQRTW,NY,NGL,IWT,NG,CQUAD,G,T,NLINF,Y)                                 SEACC7
        IF (L.LE.0 .OR. NY.LE.NGL)  GO TO 230                                  SEACC8
        J=MIN0(NGLP1,L)                                                        SEACC9
        DO 220 I=1,J                                                           SEACC0
           II=I                                                                SEACC1
           CALL H12 (1,II,IP,IP,A(1,I),1,RHO,A(1,I+1),1,MA,NGLP1-I,RANGE)      SEACC2
 220    CONTINUE                                                               SEACC3
 230    L=MIN0(NGLP1,IP)                                                       SEACC4
 200 CONTINUE                                                                  SEACC5
     IF (NY .LE. NGL)  GO TO 350                                               SEACC6
     DO 300 J=2,NGL                                                            SEACC7
        L=J-1                                                                  SEACC8
        DO 310 K=1,L                                                           SEACC9
           A(J,K)=ZERO                                                         SEACC0
 310    CONTINUE                                                               SEACC1
 300 CONTINUE                                                                  SEACC2
     GO TO 800                                                                 SEACC3
 350 L=NY+1                                                                    SEACC4
     DO 360 J=L,NGL                                                            SEACC5
        DO 370 K=1,NGLP1                                                       SEACC6
           A(J,K)=ZERO                                                         SEACC7
 370    CONTINUE                                                               SEACC8
 360 CONTINUE                                                                  SEACC9
 800 RETURN                                                                    SEACC0
     END                                                                       SEACC1
     SUBROUTINE SETGA1 (NNINEQ,                                                SEGA14
    1 A,AINEQ,MA,MG,MINEQ,MREG,NGL,NGLE,REG)                                   SEGA15
     DOUBLE PRECISION A, AINEQ, DUM, REG, ZERO                                 SEGA16
     DIMENSION AINEQ(MINEQ,MG), REG(MREG,MG), A(MA,MG)                         SEGA17
     ZERO=0.D0                                                                 SEGA19
     DO 120 IROW=1,NNINEQ                                                      SEGA10
        DO 130 ICOL=1,NGLE                                                     SEGA11
           DUM=ZERO                                                            SEGA12
           DO 140 J=1,NGL                                                      SEGA13
              DUM=DUM+AINEQ(IROW,J)*REG(J,ICOL)                                SEGA14
 140       CONTINUE                                                            SEGA15
           A(IROW,ICOL)=DUM                                                    SEGA16
 130    CONTINUE                                                               SEGA17
```

```
  120 CONTINUE
      RETURN
      END
      SUBROUTINE SETGRD (CQUAD,G,GMNMX,IGRID,IQUAD,MG,NG,NOUT)
      DIMENSION G(MG), CQUAD(MG), GMNMX(2)
      CHARACTER IHOLER(6)
      DATA IHOLER/'S','E','T','G','R','D'/
      IF (IGRID .NE. 3)  GO TO 200
      CALL USERGR (G,CQUAD,MG)
      GO TO 300
  200 IF (IGRID.EQ.2 .AND. AMIN1(GMNMX(1),GMNMX(2)).LE.0.)
     1  CALL ERRMES (1,.FALSE.,IHOLER,NOUT)
      G(1)=GMNMX(1)
      DELTA=(USERTR(GMNMX(2),1)-USERTR(GMNMX(1),1))/FLOAT(NG-1)
      DO 210 J=2,NG
         DUM=USERTR(G(J-1),1)+DELTA
         G(J)=USERTR(DUM,2)
  210 CONTINUE
  300 IF (NG .LE. 2)  GO TO 350
      DELOLD=G(2)-G(1)
      DO 310 J=3,NG
         DEL=G(J)-G(J-1)
         IF (DEL*DELOLD .GT. 0.)  GO TO 315
         CALL ERRMES (2,.FALSE.,IHOLER,NOUT)
 5310    FORMAT (1X,1P10E13.3)
         WRITE (NOUT,5310) (G(K),K=1,NG)
         STOP
  315    DELOLD=DEL
  310 CONTINUE
  350 IF (IGRID .EQ. 3)  GO TO 800
      IF (IQUAD .NE. 1)  GO TO 420
      DO 410 J=1,NG
         CQUAD(J)=1.
  410 CONTINUE
      GO TO 800
  420 IF (IQUAD .NE. 2)  GO TO 450
      CALL CQTRAP (G,CQUAD,NG)
      GO TO 500
  450 IF (IQUAD .NE. 3)  CALL ERRMES (3,.TRUE.,IHOLER,NOUT)
      CQUAD(1)=DELTA/3.
      CQ2=2.*CQUAD(1)
      CQ4=CQ2+CQ2
      JJ=NG-1
      DO 460 J=2,JJ,2
         CQUAD(J)=CQ4
         CQUAD(J+1)=CQ2
  460 CONTINUE
      IF (MOD(NG,2) .EQ. 0)  GO TO 470
      CQUAD(NG)=CQUAD(1)
      GO TO 500
  470 CQUAD(NG)=1.5*CQUAD(1)
      CQUAD(NG-1)=CQUAD(1)+CQUAD(NG)
  500 IF (IGRID .NE. 2)  GO TO 800
      DO 510 J=1,NG
         CQUAD(J)=CQUAD(J)/USERTR(G(J),3)
  510 CONTINUE
  800 RETURN
      END
      SUBROUTINE SETNNG (AINEQ,MINEQ,NG,NGLP1,NINEQ)
      DOUBLE PRECISION AINEQ, ONE, ZERO
      DIMENSION AINEQ(MINEQ,NGLP1)
      ZERO=0.D0
      ONE=1.D0
      DO 210 J=1,NG
         NINEQ=NINEQ+1
         DO 220 K=1,NGLP1
            AINEQ(NINEQ,K)=ZERO
  220    CONTINUE
         AINEQ(NINEQ,J)=ONE
  210 CONTINUE
      RETURN
      END
      SUBROUTINE SETREG (MG,MREG,NENDZ,NG,NGL,NGLE,NGLP1,NORDER,
```

```
1 NOUT,NREG,PRECIS,REG)                                              SEREG6
  DOUBLE PRECISION ABS, AMAX1, PRECIS, REG, RMAX, RMIN, SQRT,        SEREG7
1 ONE, ZERO                                                          SEREG8
  DIMENSION REG(MREG,MG), NENDZ(2)                                   SEREG9
  DIMENSION DC(6,6)                                                  SEREG0
  CHARACTER IHOLER(6)
  DATA DC/1., 5*0.,    -1., 1., 4*0.,    1., -2., 1., 3*0.,          SEREG1
1 -1., 3., -3., 1., 2*0.,    1., -4., 6., -4., 1., 0.,               SEREG2
2 -1., 5., -10., 10., -5., 1./,                                      SEREG3
3 IHOLER/'S','E','T','R','E','G'/                                    SEREG4
  ABS(RMIN)=DABS(RMIN)                                               SEREG5
  AMAX1(RMIN,RMAX)=DMAX1(RMIN,RMAX)                                  SEREG6
  SQRT(RMIN)=DSQRT(RMIN)                                             SEREG7
  ZERO=0.D0                                                          SEREG9
  ONE=1.D0                                                           SEREG1
  IF (NORDER .GE. 0)  GO TO 200                                      SEREG2
  CALL USERRG (REG,MREG,MG,NREG)                                     SEREG6
  IF (NREG .LE. 0)  CALL ERRMES (1,.TRUE.,IHOLER,NOUT)               SEREG7
  GO TO 300                                                          SEREG8
200 IF (NORDER .GT. 5)  CALL ERRMES (2,.TRUE.,IHOLER,NOUT)           SEREG9
  IF (MINO(NENDZ(1),NENDZ(2)).GE.0 .AND.  NENDZ(1)+NENDZ(2)          SEREG0
1.LE.NORDER)  GO TO 205                                              SEREG1
  CALL ERRMES (3,.FALSE.,IHOLER,NOUT)                                SEREG2
  NENDZ(1)=MAX0(0,MINO(NENDZ(1),NORDER))                             SEREG3
  NENDZ(2)=MAX0(0,MINO(NORDER-NENDZ(1),NENDZ(2)))                    SEREG4
205 NREG=NG+NENDZ(1)+NENDZ(2)-NORDER                                  SEREG5
  IF (MAX0(NREG,NGLE) .GE. MREG)  CALL ERRMES (4,.TRUE.,IHOLER,NOUT) SEREG6
  NORDP1=NORDER+1                                                    SEREG7
  DO 210 J=1,NREG                                                    SEREG8
    DO 220 K=1,NGLP1                                                 SEREG9
      REG(J,K)=ZERO                                                  SEREG0
220  CONTINUE                                                        SEREG1
    L=J-NENDZ(1)-1                                                   SEREG2
    DO 230 K=1,NORDP1                                                SEREG3
      L=L+1                                                          SEREG4
      IF (L.GE.1 .AND. L.LE.NG) REG(J,L)=DC(K,NORDP1)                SEREG5
230  CONTINUE                                                        SEREG6
210 CONTINUE                                                         SEREG7
300 RMAX=ZERO                                                        SEREG2
  DO 310 J=1,NREG                                                    SEREG3
    DO 315 K=1,NGL                                                   SEREG4
      RMAX=AMAX1(RMAX,ABS(REG(J,K)))                                 SEREG5
315  CONTINUE                                                        SEREG6
310 CONTINUE                                                         SEREG7
  RMIN=RMAX*AMAX1(1.E-4*ONE,SQRT(1.E-1*PRECIS))                      SEREG8
  DO 320 ICOL=1,NGL                                                  SEREG2
    DO 330 IROW=1,NREG                                               SEREG3
      IF (ABS(REG(IROW,ICOL)) .GT. ZERO)  GO TO 320                  SEREG4
330  CONTINUE                                                        SEREG5
    NREG=NREG+1                                                      SEREG6
    IF (NREG .GE. MREG)  CALL ERRMES (5,.TRUE.,IHOLER,NOUT)          SEREG7
    DO 335 J=1,NGLP1                                                 SEREG8
      REG(NREG,J)=ZERO                                               SEREG9
335  CONTINUE                                                        SEREG0
    REG(NREG,ICOL)=RMIN                                              SEREG1
320 CONTINUE                                                         SEREG2
  IF (NREG .GE. NGLE)  GO TO 800                                     SEREG3
  K=NGLE-NREG                                                        SEREG8
  DO 350 J=1,NGL                                                     SEREG9
    DO 360 IROW=1,NREG                                               SEREG0
      IF (ABS(REG(IROW,J)) .LT. RMIN)  GO TO 360                     SEREG1
      DO 370 ICOL=1,NGL                                              SEREG2
        IF (ICOL.NE.J .AND. ABS(REG(IROW,J)).GE.RMIN)  GO TO 360     SEREG3
370    CONTINUE                                                      SEREG4
      GO TO 350                                                      SEREG5
360  CONTINUE                                                        SEREG6
    K=K-1                                                            SEREG7
    IROW=NGLE-K                                                      SEREG8
    DO 380 ICOL=1,NGLP1                                              SEREG9
      REG(IROW,ICOL)=ZERO                                            SEREG0
380  CONTINUE                                                        SEREG1
    REG(IROW,J)=RMIN                                                 SEREG2
    IF (K) 390,390,350                                               SEREG3
```

```
350 CONTINUE                                                              SEREG4
      CALL ERRMES (6,.TRUE.,IHOLER,NOUT)                                  SEREG5
390 NREG=NGLE                                                             SEREG6
800 RETURN                                                                SEREG7
      END                                                                 SEREG8
      SUBROUTINE SETSGN (INSGN,NSGNI,LSIGN,NOUT,LLSIGN,NG,SOLBES,         SESGN3
     1 SRANGE)                                                            SESGN4
      DOUBLE PRECISION SOLBES                                             SESGN5
      DIMENSION LSIGN(4,INSGN), LLSIGN(5), SOLBES(NG)                     SESGN6
      CHARACTER IHOLER(6)                                                 SESGN7
      DATA IHOLER/'S','E','T','S','G','N'/                                SESGN8
      IF (NSGNI.LT.1 .OR. NSGNI.GT.4 .OR. IABS(LSIGN(1,INSGN)).NE.1)      SESGN9
     1 CALL ERRMES (1,.TRUE.,IHOLER,NOUT)                                 SESGN0
      LLSIGN(1)=LSIGN(1,INSGN)                                            SESGN1
      LLSIGN(NSGNI+1)=NG                                                  SESGN2
      IF (NSGNI .EQ. 1) GO TO 800                                         SESGN3
      DO 110 ISGN=2,NSGNI                                                 SESGN4
        LLSIGN(ISGN)=LSIGN(ISGN,INSGN)                                    SESGN5
        IF (IABS(LLSIGN(ISGN)) .GT. IABS(LLSIGN(ISGN-1))                  SESGN6
     1 .AND. IABS(LLSIGN(ISGN)) .LT. NG    .AND. LLSIGN(ISGN)*            SESGN7
     2LLSIGN(ISGN-1) .LT. 0) GO TO 110                                    SESGN8
        IF (ISGN.NE.2 .OR. NSGNI.NE.2) CALL ERRMES(2,.TRUE.,IHOLER,       SESGN9
     1NOUT)                                                               SESGN0
        F=FLOAT(LLSIGN(1))                                                SESGN5
        PK=SRANGE                                                         SESGN6
        DO 120 J=1,NG                                                     SESGN7
          DUM=F*SOLBES(J)                                                 SESGN8
          IF (DUM .GE. PK) GO TO 120                                      SESGN9
          PK=DUM                                                          SESGN0
          LLSIGN(2)=-ISIGN(J,LLSIGN(1))                                   SESGN1
120     CONTINUE                                                          SESGN2
110 CONTINUE                                                              SESGN3
800 RETURN                                                                SESGN4
      END                                                                 SESGN5
      SUBROUTINE SETVAL (ALPHA,INIT,NNINEQ,                               SEVAL8
     1 A,AINEQ,MA,MG,MINEQ,MREG,NGL,NGLE,REG,RHSNEQ,S,VALPCV,VALPHA,      SEVAL9
     2 VK1Y1)                                                             SEVAL0
      DOUBLE PRECISION A, AINEQ, ALPHA, ALPHA2, DDUM, DUM, FACT,          SEVAL1
     1 ONE, REG, RHSNEQ, S, SQRT, VALPCV, VALPHA, VK1Y1                   SEVAL2
      LOGICAL INIT                                                        SEVAL3
      DIMENSION S(MG,3), VK1Y1(MG), REG(MREG,MG), A(MA,MG),               SEVAL4
     1 VALPHA(MG), VALPCV(MG), AINEQ(MINEQ,MG), RHSNEQ(MINEQ)             SEVAL5
      SQRT(DUM)=DSQRT(DUM)                                                SEVAL6
      ONE=1.D0                                                            SEVAL8
      IF (.NOT.INIT) GO TO 108                                            SEVAL9
      DO 105 J=1,NGLE                                                     SEVAL0
        S(J,2)=ONE                                                        SEVAL1
105 CONTINUE                                                              SEVAL2
108 ALPHA2=ALPHA**2                                                       SEVAL3
      DO 110 J=1,NGL                                                      SEVAL4
        VALPCV(J)=VK1Y1(J)                                                SEVAL5
        VALPHA(J)=VK1Y1(J)                                                SEVAL6
110 CONTINUE                                                              SEVAL7
      NGLP1=NGL+1                                                         SEVAL8
      DO 120 J=1,NGLE                                                     SEVAL9
        DDUM=ONE/(S(J,1)**2+ALPHA2)                                       SEVAL0
        DUM=(ALPHA2*REG(J,NGLP1)+S(J,1)*A(J,NGLP1))*DDUM                  SEVAL1
        DDUM=SQRT(DDUM)                                                   SEVAL2
        FACT=DDUM/S(J,2)                                                  SEVAL3
        S(J,2)=DDUM                                                       SEVAL4
        DO 125 K=1,NGL                                                    SEVAL5
          VALPHA(K)=VALPHA(K)+DUM*REG(K,J)                                SEVAL6
125     CONTINUE                                                          SEVAL7
        IF (NNINEQ .LE. 0) GO TO 120                                      SEVAL8
        DUM=REG(J,NGLP1)                                                  SEVAL2
        DO 130 K=1,NGL                                                    SEVAL3
          VALPCV(K)=VALPCV(K)+DUM*REG(K,J)                                SEVAL4
130     CONTINUE                                                          SEVAL5
        DO 140 K=1,NNINEQ                                                 SEVAL9
          A(K,J)=FACT*A(K,J)                                              SEVAL0
140     CONTINUE                                                          SEVAL1
120 CONTINUE                                                              SEVAL2
      IF (NNINEQ .LE. 0) GO TO 800                                        SEVAL3
```

```
      DO 150 K=1,NNINEQ                                              SEVAL7
         DUM=AINEQ(K,NGLP1)                                          SEVAL8
         DO 160 J=1,NGL                                              SEVAL9
            DUM=DUM-AINEQ(K,J)*VALPHA(J)                             SEVAL0
160      CONTINUE                                                    SEVAL1
         RHSNEQ(K)=DUM                                               SEVAL2
150   CONTINUE                                                       SEVAL3
800   RETURN                                                         SEVAL4
      END                                                            SEVAL5
      SUBROUTINE SETWT (                                             SETWT5
     1 CQUAD,G,IUNIT,IWT,MWORK,MY,NERFIT,NG,NGL,NLINF,NOUT,NY,PRWT,  SETWT6
     2 SOLBES,SQRTW,SRANGE,T,WORK,Y,YLYFIT)                          SETWT7
      DOUBLE PRECISION SOLBES, WORK                                  SETWT8
      LOGICAL PRWT                                                   SETWT9
      DIMENSION SOLBES(NGL), WORK(MWORK), SQRTW(MY), CQUAD(NG),      SETWT0
     1 G(NG), T(MY), Y(MY), YLYFIT(MY)                               SETWT1
      CHARACTER IHOLER(6)                                            SETWT2
      DATA IHOLER/'S','E','T','W','T',' '/                           SETWT3
      CALL GETYLY (SOLBES,                                           SETWT4
     1 CQUAD,G,IUNIT,IWT,MWORK,NG,NGL,NLINF,NY,SQRTW,T,WORK,Y,YLYFIT) SETWT5
      ERRFIT=0.                                                      SETWT6
      IF (NERFIT.LE.0)   GO TO 200                                   SETWT7
      ABSMIN=SRANGE                                                  SETWT5
      DO 110 J=1,NY                                                  SETWT6
         DUM=ABS(Y(J)-YLYFIT(J))                                     SETWT7
         IF (DUM .GE. ABSMIN)   GO TO 110                            SETWT8
         ABSMIN=DUM                                                  SETWT9
         L=J                                                         SETWT0
110   CONTINUE                                                       SETWT1
      JMAX=MIN0(NY,L+NERFIT/2)                                       SETWT2
      JMIN=MAX0(1,JMAX-NERFIT+1)                                     SETWT3
      DUM=0.                                                         SETWT4
      DO 120 J=JMIN,JMAX                                             SETWT5
         DUM=DUM+YLYFIT(J)**2                                        SETWT6
120   CONTINUE                                                       SETWT7
      ERRFIT=SQRT(DUM/FLOAT(JMAX-JMIN+1))                            SETWT8
200   IF (IWT .NE. 5)   GO TO 250                                    SETWT9
      CALL USERWT (Y,YLYFIT,MY,ERRFIT,SQRTW)                         SETWT0
      GO TO 700                                                      SETWT1
250   IF (IWT.NE.2 .AND. IWT.NE.3)   CALL ERRMES (1,.TRUE.,IHOLER,NOUT) SETWT2
      DO 260 J=1,NY                                                  SETWT3
         DUM=AMAX1(ABS(Y(J)-YLYFIT(J)),ERRFIT)                       SETWT4
         IF (DUM .LE. 0.)   CALL ERRMES (2,.TRUE.,IHOLER,NOUT)       SETWT5
         SQRTW(J)=1./DUM                                             SETWT6
         IF (IWT .EQ. 2)   SQRTW(J)=SQRT(SQRTW(J))                   SETWT7
260   CONTINUE                                                       SETWT8
5260  FORMAT (//' ERRFIT =',1PE9.2//20X,                             SETWT9
     1 'SQUARE ROOTS OF LEAST SQUARES WEIGHTS'//                     SETWT0
     2 (1X,1P10E13.4))                                               SETWT1
700   IF (PRWT)   WRITE (NOUT,5260) ERRFIT,(SQRTW(J),J=1,NY)         SETWT2
      RETURN                                                         SETWT3
      END                                                            SETWT4
      SUBROUTINE STORIN (JL,NIDERR,LIN,IIN,RIN)                      STRIN4
      DOUBLE PRECISION PRECIS, RANGE                                 STRIN5
      LOGICAL DOMOM, DOUSIN, DOUSNQ, DOUSOU, LAST, NONNEG, ONLY1, PRWT, STRIN6
     1 PRY, SIMULA, LUSER                                            STRIN7
      LOGICAL LEQUIV(10)                                             STRIN8
      CHARACTER IFORMT(70),IFORMW(70),IFORMY(70),LA(6,46),ITITLE(80)
      DIMENSION LIN(6), IEQUIV(15)                                   STRIN9
      COMMON /SBLOCK/ PRECIS, RANGE, SRMIN,                          STRINO
     1 ALPST(2), GMNMX(2), PLEVEL(2,2), RSVMNX(2,2), RUSER(100),     STRIN1
     2 EXMAX, SRANGE                                                 STRIN2
      COMMON /CBLOCK/ IFORMT,IFORMW,IFORMY, LA,ITITLE
      COMMON /IBLOCK/ IGRID, IPLRES, IPRINT, IQUAD, IUNIT, IWT,      STRIN3
     1 LINEPG, MIDERR, MQPITR, NEQ, NERFIT, NG, NINTT, NLINF, NORDER, STRIN4
     2 ICRIT(2),  IPLFIT(2),                                         STRIN5
     3  IUSER(50), LSIGN(4,4), MOMNMX(2), NENDZ(2),                  STRIN6
     4 NFLAT(4,2), NGL, NGLP1, NIN, NINEQ, NNSGN(2), NOUT, NQPROG(2), STRIN7
     5 NSGN(4), NY                                                   STRIN8
      COMMON /LBLOCK/ DOMOM, DOUSIN, DOUSNQ, DOUSOU, LAST, NONNEG,   STRIN9
     1 ONLY1, PRWT, PRY, SIMULA,                                     STRINO
     2 LUSER(30)                                                     STRIN1
```

```
      EQUIVALENCE (IGRID,IEQUIV(1)), (DOMOM,LEQUIV(1))                    STRIN2
      IFINT(RIN)=INT(RIN*1.001)                                           STRIN3
      IF (JL .GT. 1)   GO TO 200                                          STRIN4
      SRMIN=RIN                                                           STRIN5
      RETURN                                                              STRIN6
  200 IF (JL .GT. 6)   GO TO 300                                          STRIN7
      JLL=JL-1                                                            STRIN8
      GO TO (202,203,204,205,206),JLL                                     STRIN9
  202 IF (IIN.LT.1 .OR. IIN.GT.2)  GO TO 805                              STRIN0
      ALPST(IIN)=RIN                                                      STRIN1
      RETURN                                                              STRIN2
  203 IF (IIN.LT.1 .OR. IIN.GT.2)  GO TO 805                              STRIN3
      GMNMX(IIN)=RIN                                                      STRIN4
      RETURN                                                              STRIN5
 5204 FORMAT (4F5.2)                                                      STRIN6
  204 READ (NIN,5204) PLEVEL                                              STRIN7
      WRITE (NOUT,5204) PLEVEL                                            STRIN8
      RETURN                                                              STRIN9
 5205 FORMAT (4E10.3)                                                     STRIN0
  205 READ (NIN,5205) RSVMNX                                              STRIN1
      WRITE (NOUT,5205) RSVMNX                                            STRIN2
      RETURN                                                              STRIN3
  206 IF (IIN.LT.1 .OR. IIN.GT.100)  GO TO 805                            STRIN8
      RUSER(IIN)=RIN                                                      STRIN9
      RETURN                                                              STRIN0
  300 IF (JL .GT. 21)   GO TO 400                                         STRIN1
      IEQUIV(JL-6)=IIN                                                    STRIN2
      RETURN                                                              STRIN3
  400 IF (JL .GT. 34)   GO TO 500                                         STRIN4
      JLL=JL-21                                                           STRIN5
      GO TO (422,423,424,425,426,427,428,429,430,431,432,433,434),JLL     STRIN6
  422 IF (IIN.LT.1 .OR. IIN.GT.2)  GO TO 805                              STRIN7
      ICRIT(IIN)=IFINT(RIN)                                               STRIN8
      RETURN                                                              STRIN9
 5423 FORMAT (1X,70A1)                                                    STRIN0
  423 READ (NIN,5423) IFORMT                                              STRIN1
      WRITE (NOUT,5423) IFORMT                                            STRIN2
      RETURN                                                              STRIN3
  424 READ (NIN,5423) IFORMW                                              STRIN4
      WRITE (NOUT,5423) IFORMW                                            STRIN5
      RETURN                                                              STRIN6
  425 READ (NIN,5423) IFORMY                                              STRIN7
      WRITE (NOUT,5423) IFORMY                                            STRIN8
      RETURN                                                              STRIN9
  426 IF (IIN.LT.1 .OR. IIN.GT.2)  GO TO 805                              STRIN0
      IPLFIT(IIN)=IFINT(RIN)                                              STRIN1
      RETURN                                                              STRIN2
  427 IF (IIN.LT.1 .OR. IIN.GT.50)  GO TO 805                             STRIN7
      IUSER(IIN)=IFINT(RIN)                                               STRIN8
      RETURN                                                              STRIN9
 5428 FORMAT (16I5)                                                       STRIN0
  428 READ (NIN,5428) LSIGN                                               STRIN1
      WRITE (NOUT,5428) LSIGN                                             STRIN2
      RETURN                                                              STRIN3
  429 IF (IIN.LT.1 .OR. IIN.GT.2)  GO TO 805                              STRIN4
      MOMNMX(IIN)=IFINT(RIN)                                              STRIN5
      RETURN                                                              STRIN6
  430 IF (IIN.LT.1 .OR. IIN.GT.2)  GO TO 805                              STRIN7
      NENDZ(IIN)=IFINT(RIN)                                               STRIN8
      RETURN                                                              STRIN9
  431 READ (NIN,5428) NFLAT                                               STRIN0
      WRITE (NOUT,5428) NFLAT                                             STRIN1
      RETURN                                                              STRIN2
  432 IF (IIN.LT.1 .OR. IIN.GT.2)  GO TO 805                              STRIN3
      NNSGN(IIN)=IFINT(RIN)                                               STRIN4
      RETURN                                                              STRIN5
  433 IF (IIN.LT.1 .OR. IIN.GT.2)  GO TO 805                              STRIN6
      NQPROG(IIN)=IFINT(RIN)                                              STRIN7
      RETURN                                                              STRIN8
  434 IF (IIN.LT.1 .OR. IIN.GT.4)  GO TO 805                              STRIN9
      NSGN(IIN)=IFINT(RIN)                                                STRIN0
      RETURN                                                              STRIN1
```

```
 500 IF (JL .GT. 44) GO TO 645                                      STRIN2
     LEQUIV(JL-34)=.NOT.LEQUIV(JL-34)                               STRIN3
     RETURN                                                         STRIN4
 645 IF (IIN.LT.1 .OR. IIN.GT.30)  GO TO 805                        STRIN9
     LUSER(IIN)=.NOT.LUSER(IIN)                                     STRINO
     RETURN                                                         STRIN1
 805 WRITE (NOUT,5805) IIN,LIN                                      STRIN2
5805 FORMAT (' SUBSCRIPT =',I3,' OF ',6A1,' IS OUT OF RANGE.  ',    STRIN3
    1 44('xx'))                                                     STRIN4
     NIOERR=NIOERR+1                                                STRIN5
     IF (NIOERR .GE. MIOERR)  STOP                                  STRIN6
     RETURN                                                         STRIN7
     END                                                            STRIN8
     SUBROUTINE SVDRS2 (A,MDA,MM,NN,B,MDB,NB,S,IERROR,RANGE)        SVRS27
     DOUBLE PRECISION A, B, ONE, RANGE, S, T, ZERO                  SVRS28
     DIMENSION A(MDA,1),B(MDB,1),S(NN,3)                            SVRS29
     ZERO=0.D0                                                      SVRS21
     ONE=1.D0                                                       SVRS23
     N=NN                                                           SVRS29
     IERROR=6                                                       SVRS20
     IF (N.LE.0.OR.MM.LE.0)  RETURN                                 SVRS21
     IERROR=1                                                       SVRS22
     J=N                                                            SVRS23
  10 CONTINUE                                                       SVRS24
        DO 20 I=1,MM                                                SVRS25
        IF (A(I,J))   50,20,50                                      SVRS26
  20    CONTINUE                                                    SVRS27
     IF (J.EQ.N)  GO TO 40                                          SVRS21
        DO 30 I=1,MM                                                SVRS22
  30    A(I,J)=A(I,N)                                               SVRS23
  40 CONTINUE                                                       SVRS24
     A(1,N)=J                                                       SVRS25
     N=N-1                                                          SVRS26
  50 CONTINUE                                                       SVRS27
     J=J-1                                                          SVRS28
     IF (J.GE.1)  GO TO 10                                          SVRS29
     NS=0                                                           SVRS22
     IF (N.EQ.0)  GO TO 240                                         SVRS23
     I=1                                                            SVRS26
     M=MM                                                           SVRS27
  60 IF (I.GT.N.OR.I.GE.M)   GO TO 150                              SVRS28
     IF (A(I,I))   90,70,90                                         SVRS29
  70    DO 80 J=1,N                                                 SVRS20
        IF (A(I,J))   90,80,90                                      SVRS21
  80    CONTINUE                                                    SVRS22
     GO TO 100                                                      SVRS23
  90 I=I+1                                                          SVRS24
     GO TO 60                                                       SVRS25
 100 IF(NB.LE.0)  GO TO 115                                         SVRS28
        DO 110 J=1,NB                                               SVRS29
        T=B(I,J)                                                    SVRS20
        B(I,J)=B(M,J)                                               SVRS21
 110    B(M,J)=T                                                    SVRS22
 115    DO 120 J=1,N                                                SVRS23
 120    A(I,J)=A(M,J)                                               SVRS24
     IF (M.GT.N)  GO TO 140                                         SVRS25
        DO 130 J=1,N                                                SVRS26
 130    A(M,J)=ZERO                                                 SVRS27
 140 CONTINUE                                                       SVRS28
     M=M-1                                                          SVRS20
     GO TO 60                                                       SVRS21
 150 CONTINUE                                                       SVRS23
     L=MINO(M,N)                                                    SVRS29
        DO 170 J=1,L                                                SVRS23
        IF (J.GE.M)  GO TO 160                                      SVRS24
        JJ=J                                                        SVRS25
        CALL H12 (1,JJ,J+1,M,A(1,J),1,T,A(1,J+1),1,MDA,N-J,RANGE)   SVRS26
        CALL H12 (2,JJ,J+1,M,A(1,J),1,T,B,1,MDB,NB,RANGE)           SVRS27
 160    IF (J.GE.N-1)  GO TO 170                                    SVRS28
        CALL H12 (1,J+1,J+2,N,A(J,1),MDA,S(J,3),A(J+1,1),MDA,1,M-J, SVRS29
    1   RANGE)                                                      SVRS20
 170  CONTINUE                                                      SVRS21
     IF (N.EQ.1)  GO TO 190                                         SVRS25
```

```
          DO 180 J=2,N                                                    SVRS26
          S(J,1)=A(J,J)                                                   SVRS27
180       S(J,2)=A(J-1,J)                                                 SVRS28
190    S(1,1)=A(1,1)                                                      SVRS29
       NS=N                                                               SVRS21
       IF (M.GE.N)  GO TO 200                                             SVRS22
       NS=M+1                                                             SVRS23
       S(NS,1)=ZERO                                                       SVRS24
       S(NS,2)=A(M,M+1)                                                   SVRS25
200    CONTINUE                                                           SVRS26
          DO 230 K=1,N                                                    SVRS21
          I=N+1-K                                                         SVRS22
          IF(I.GT.MINO(M,N-2))  GO TO 210                                 SVRS23
          CALL H12 (2,I+1,I+2,N,A(I,1),MDA,S(I,3),A(1,I+1),1,MDA,N-I,     SVRS24
     1    RANGE)                                                          SVRS25
210       DO 220 J=1,N                                                    SVRS26
220       A(I,J)=ZERO                                                     SVRS27
230       A(I,I)=ONE                                                      SVRS28
       CALL QRBD (IPASS,S(1,1),S(1,2),NS,A,MDA,N,B,MDB,NB,RANGE)          SVRS22
       GO TO (240,310), IPASS                                             SVRS23
240    CONTINUE                                                           SVRS24
       IF (NS.GE.N)  GO TO 260                                            SVRS25
       NSP1=NS+1                                                          SVRS26
          DO 250 J=NSP1,N                                                 SVRS27
250       S(J,1)=ZERO                                                     SVRS28
260    CONTINUE                                                           SVRS29
       IF (N.EQ.NN)  RETURN                                               SVRS20
       NP1=N+1                                                            SVRS21
          DO 280 J=NP1,NN                                                 SVRS22
          S(J,1)=A(1,J)                                                   SVRS25
          DO 270 I=1,N                                                    SVRS26
270       A(I,J)=ZERO                                                     SVRS27
280       CONTINUE                                                        SVRS28
          DO 300 K=NP1,NN                                                 SVRS29
          I=S(K,1)                                                        SVRS21
          S(K,1)=ZERO                                                     SVRS22
          DO 290 J=1,NN                                                   SVRS23
          A(K,J)=A(I,J)                                                   SVRS24
290       A(I,J)=ZERO                                                     SVRS25
          A(I,K)=ONE                                                      SVRS26
300       CONTINUE                                                        SVRS27
       RETURN                                                             SVRS28
310    IERROR=5                                                           SVRS20
       RETURN                                                             SVRS21
       END                                                                SVRS22
       SUBROUTINE UPDDON (                                                SVRS23
     1 NSGNM1,LLSIGN,LSDONE,MDONE,NDONE,NNQUSR,LBIND,MINEQ,               UPDON0
     2 NG,VARI,VDONE)                                                     UPDON1
       LOGICAL LBIND, STORE                                               UPDON2
       DIMENSION LLSIGN(5), LSDONE(MDONE,3,2), LBIND(MINEQ),              UPDON3
     1 VDONE(MDONE)                                                       UPDON4
       STORE=NSGNM1 .GE. 1                                                UPDON5
       IF (.NOT.STORE)  GO TO 700                                         UPDON6
       VDONE(NDONE)=VARI                                                  UPDON7
       DO 110 J=1,NSGNM1                                                  UPDON8
         L=IABS(LLSIGN(J+1))                                              UPDON9
         KK=L-IABS(LLSIGN(J))-1                                           UPDON0
         LL=L+NNQUSR+1                                                    UPDON1
         IF (KK .EQ. 0)   GO TO 130                                       UPDON2
         DO 120 K=1,KK                                                    UPDON3
           LL=LL-1                                                        UPDON4
           IF (.NOT.LBIND(LL))  GO TO 130                                 UPDON5
120      CONTINUE                                                         UPDON6
         LL=LL-1                                                          UPDON7
130      LSDONE(NDONE,J,1)=MINO(LL-NNQUSR+1,L)                            UPDON8
         KK=IABS(LLSIGN(J+2))-L-1                                         UPDON9
         LL=NNQUSR-1+L                                                    UPDON0
         IF (KK .EQ. 0)   GO TO 150                                       UPDON1
         DO 140 K=1,KK                                                    UPDON2
           LL=LL+1                                                        UPDON3
           IF (.NOT.LBIND(LL))  GO TO 150                                 UPDON4
140      CONTINUE                                                         UPDON5
         LL=LL+1                                                          UPDON6
```

```
150   LSDONE(NDONE,J,2)=MAX0(LL-NNQUSR-1,L)                           UPDON8
      IF (LSDONE(NDONE,J,1) .EQ. L)  LSDONE(NDONE,J,1)=-L            UPDON9
      IF (LSDONE(NDONE,J,2) .EQ. L)  LSDONE(NDONE,J,2)=-L            UPDON0
110 CONTINUE                                                         UPDON1
    IF (NDONE .LE. 1)  GO TO 700                                     UPDON5
    KK=NDONE-1                                                       UPDON6
    DO 210 K=1,KK                                                    UPDON7
      DO 220 J=1,NSGNM1                                              UPDON8
        IF (IABS(LSDONE(NDONE,J,1)) .NE. IABS(LSDONE(K,J,1))         UPDON9
   1    .OR.   IABS(LSDONE(NDONE,J,2)) .NE. IABS(LSDONE(K,J,2)))     UPDON0
   2    GO TO 210                                                    UPDON1
220   CONTINUE                                                       UPDON2
      VARI=VDONE(K)                                                  UPDON3
      STORE=.FALSE.                                                  UPDON4
      GO TO 700                                                      UPDON5
210 CONTINUE                                                         UPDON6
700 IF (.NOT.STORE)   NDONE=NDONE-1                                  UPDON7
    RETURN                                                           UPDON8
    END                                                              UPDON9
    SUBROUTINE UPDLLS (NSGNI,JSTAGE,NOUT,VARTRY,VARI,LLSTRY,         UPLLS2
   1 LLSIGN,INC,DONE)                                                UPLLS3
    LOGICAL DONE                                                     UPLLS4
    DIMENSION JSTAGE(NSGNI), VARTRY(NSGNI), LLSTRY(5,NSGNI),         UPLLS5
   1 LLSIGN(5), INC(NSGNI)                                           UPLLS6
    CHARACTER IHOLER(6)                                              UPLLS7
    DATA IHOLER/'U','P','D','L','L','S'/                             UPLLS8
    IF (NSGNI .LE. 1)  GO TO 790                                     UPLLS9
    NSGNP1=NSGNI+1                                                   UPLLS0
    DONE=.FALSE.                                                     UPLLS1
    L=NSGNP1                                                         UPLLS2
    DO 200 JLL=2,NSGNI                                               UPLLS3
      L=L-1                                                          UPLLS7
      JSTAGE(L)=JSTAGE(L)+1                                          UPLLS5
      IF (JSTAGE(L) .LT. 1)  CALL ERRMES (1,.TRUE.,IHOLER,NOUT)      UPLLS6
      IF (JSTAGE(L)-2)  300,400,500                                  UPLLS7
300   IF (L .LT. NSGNI)  GO TO 330                                   UPLLS8
      VARTRY(L)=VARI                                                 UPLLS3
      DO 310 J=1,NSGNP1                                              UPLLS4
        LLSTRY(J,L)=IABS(LLSIGN(J))                                  UPLLS5
310   CONTINUE                                                       UPLLS6
      GO TO 350                                                      UPLLS7
330   VARTRY(L)=VARTRY(L+1)                                          UPLLS2
      DO 340 J=1,NSGNP1                                              UPLLS3
        LLSTRY(J,L)=LLSTRY(J,L+1)                                    UPLLS4
340   CONTINUE                                                       UPLLS5
350   DO 360 LL=2,NSGNI                                              UPLLS0
        LLSIGN(LL)=ISIGN(LLSTRY(LL,L),LLSIGN(LL))                    UPLLS1
360   CONTINUE                                                       UPLLS2
      LL=LLSTRY(L,L)+INC(L)                                          UPLLS3
      LLSIGN(L)=ISIGN(LL,LLSIGN(L))                                  UPLLS4
      IF (LL.GT.LLSTRY(L-1,L) .AND. LL.LT.LLSTRY(L+1,L))  GO TO 800  UPLLS8
      IF (LL.LE.LLSTRY(L-1,L) .OR. L.GE.NSGNI)  GO TO 370            UPLLS2
      LLSIGN(L+1)=ISIGN(LLSTRY(L+1,L)+1,LLSIGN(L+1))                 UPLLS6
      IF (IABS(LLSIGN(L+1)) .LT. LLSTRY(L+2,L))  GO TO 800           UPLLS7
      IF (L+1 .GE. NSGNI)  GO TO 370                                 UPLLS2
      LLSIGN(L+2)=ISIGN(LLSTRY(L+2,L)+1,LLSIGN(L+2))                 UPLLS6
      IF (IABS(LLSIGN(L+2)) .LT. LLSTRY(L+3,L))  GO TO 800           UPLLS7
370   IF (JSTAGE(L) .GT. 1)  GO TO 510                               UPLLS2
      JSTAGE(L)=2                                                    UPLLS3
      GO TO 420                                                      UPLLS4
400   IF (VARI-VARTRY(L))  300,410,420                               UPLLS1
410   JSTAGE(L)=1                                                    UPLLS6
      GO TO 300                                                      UPLLS7
420   INC(L)=-1                                                      UPLLS2
      GO TO 350                                                      UPLLS3
500   IF (VARI .LE. VARTRY(L))  GO TO 300                            UPLLS0
510   DO 520 LL=L,NSGNI                                              UPLLS5
        JSTAGE(LL)=0                                                 UPLLS6
        INC(LL)=1                                                    UPLLS7
520   CONTINUE                                                       UPLLS8
      VARI=VARTRY(L)                                                 UPLLS9
200 CONTINUE                                                         UPLLS0
790 DONE=.TRUE.                                                      UPLLS4
```

```
800   RETURN                                                              UPLLS5
      END                                                                 UPLLS6
      SUBROUTINE UPDSGN (NNSGNI,LLLSGN,                                   UPSGN8
     1 A,AINEQ,IISIGN,MA,MG,MINEQ,MREG,NGLE,NGLP1,NNINEQ,                 UPSGN9
     2 NNQUSR,NONNEG,NOUT,REG,RHSNEQ,S,VALPHA)                            UPSGN0
      DOUBLE PRECISION A, AINEQ, ONE, REG, RHSNEQ, S, VALPHA, ZERO        UPSGN1
      LOGICAL NONNEG                                                      UPSGN2
      DIMENSION LLLSGN(5), A(MA,MG), REG(MREG,MG), S(MG,3),               UPSGN3
     1 RHSNEQ(MINEQ), VALPHA(MG), IISIGN(MG), AINEQ(MINEQ,MG)             UPSGN4
      CHARACTER IHOLER(6)                                                 UPSGN5
      DATA IHOLER/'U','P','D','S','G','N'/                                UPSGN6
      ZERO=0.D0                                                           UPSGN8
      ONE=1.D0                                                            UPSGN0
      IROW=NNQUSR                                                         UPSGN1
      IIROW=NNINEQ                                                        UPSGN2
      NNSGNP=NNSGNI+1                                                     UPSGN3
      DO 110 JS=1,NNSGNP                                                  UPSGN4
        LS=LLLSGN(JS)                                                     UPSGN5
        ICMIN=IABS(LS)                                                    UPSGN6
        IF (JS .LE. NNSGNI)  GO TO 114                                    UPSGN7
        IF (NONNEG .AND. LLLSGN(NNSGNI).GT.0)   GO TO 116                 UPSGN8
        GO TO 110                                                         UPSGN9
114     ICMAX=IABS(LLLSGN(JS+1))-1                                        UPSGN0
        IF (ICMIN .GT. ICMAX)  CALL ERRMES (1,.TRUE.,IHOLER,NOUT)         UPSGN1
        IF (.NOT.NONNEG .OR. LS.GT.0)  GO TO 130                          UPSGN2
116     IIROW=IIROW+1                                                     UPSGN6
        IF (IIROW .GT. MINEQ)  CALL ERRMES (2,.TRUE.,IHOLER,NOUT)         UPSGN7
        DO 120 IICOL=1,NGLE                                               UPSGN8
          A(IIROW,IICOL)=REG(ICMIN,IICOL)*S(IICOL,2)                      UPSGN9
120     CONTINUE                                                          UPSGN0
        RHSNEQ(IIROW)=-VALPHA(ICMIN)                                      UPSGN1
        DO 125 IICOL=1,NGLP1                                              UPSGN2
          AINEQ(IIROW,IICOL)=ZERO                                         UPSGN3
125     CONTINUE                                                          UPSGN4
        AINEQ(IIROW,ICMIN)=ONE                                            UPSGN5
        IF (JS. GT. NNSGNI)  GO TO 110                                    UPSGN6
130     DO 140 ICOL=ICMIN,ICMAX                                           UPSGN0
          IROW=IROW+1                                                     UPSGN1
          IF (IROW .GT. NNINEQ)  CALL ERRMES (3,.TRUE.,IHOLER,NOUT)       UPSGN2
          IF (IISIGN(ICOL)*LS .GT. 0)  GO TO 140                          UPSGN3
          IISIGN(ICOL)=-IISIGN(ICOL)                                      UPSGN4
          DO 145 IICOL=1,NGLE                                             UPSGN5
            A(IROW,IICOL)=-A(IROW,IICOL)                                  UPSGN6
145       CONTINUE                                                        UPSGN7
          RHSNEQ(IROW)=-RHSNEQ(IROW)                                      UPSGN8
140     CONTINUE                                                          UPSGN9
110   CONTINUE                                                            UPSGN0
      RETURN                                                              UPSGN1
      END                                                                 UPSGN2
      SUBROUTINE USEREQ (AEQ,CQUAD,MEQ,MG)                                USREQ4
      DOUBLE PRECISION PRECIS, RANGE                                      USREQ5
      DOUBLE PRECISION AEQ                                                USREQ6
      LOGICAL DOMOM, DOUSIN, DOUSNQ, DOUSOU, LAST, NONNEG, ONLY1, PRWT,   USREQ7
     1 PRY, SIMULA, LUSER                                                 USREQ8
      DIMENSION AEQ(MEQ,MG), CQUAD(MG)                                    USREQ9
      COMMON /SBLOCK/ PRECIS, RANGE, SRMIN,                               USREQ0
     1 ALPST(2), GMNMX(2), PLEVEL(2,2), RSVMNX(2,2), RUSER(100),          USREQ1
     2 EXMAX, SRANGE                                                      USREQ2
      COMMON /IBLOCK/ IGRID, IPLRES, IPRINT, IQUAD, IUNIT, IWT,           USREQ3
     1 LINEPG, MIOERR, MQPITR, NEQ, NERFIT, NG, NINTT, NLINF, NORDER,     USREQ4
     2 ICRIT(2), IPLFIT(2),
     3  IUSER(50), LSIGN(4,4), MOMNMX(2), NENDZ(2),                       USREQ6
     4 NFLAT(4,2), NGL, NGLP1, NIN, NINEQ, NNSGN(2), NOUT, NQPROG(2),     USREQ7
     5 NSGN(4), NY                                                        USREQ8
      COMMON /LBLOCK/ DOMOM, DOUSIN, DOUSNQ, DOUSOU, LAST, NONNEG,        USREQ9
     1 ONLY1, PRWT, PRY, SIMULA,                                          USREQ0
     2 LUSER(30)                                                          USREQ1
      ZERO=0.D0                                                           USREQ3
      ONE=1.D0                                                            USREQ5
      IF (NEQ.GE.1 .AND. NEQ.LE.3)  GO TO 105                             USREQ0
5105  FORMAT (/' NEQ =',I3,' IS NOT 1, 2 OR 3 IN USEREQ.')                USREQ1
      WRITE (NOUT,5105) NEQ                                               USREQ2
      STOP                                                                USREQ3
```

```
  105 L=MIN0(NEQ,2)                                              USREQ4
      DO 110 J=1,L                                               USREQ5
        DO 120 K=1,NGL                                           USREQ6
          AEQ(J,K)=ZERO                                          USREQ7
  120   CONTINUE                                                 USREQ8
        AEQ(J,NGLP1)=RUSER(J)                                    USREQ9
  110 CONTINUE                                                   USREQ0
      AEQ(1,NG)=ONE                                              USREQ1
      IF (NEQ .GT. 1)  AEQ(2,1)=ONE                              USREQ2
      IF (NEQ .NE. 3)  GO TO 800                                 USREQ3
      DO 130 K=1,NGL                                             USREQ4
        AEQ(3,K)=ZERO                                            USREQ5
        IF (K .LE. NG)  AEQ(3,K)=CQUAD(K)                        USREQ6
  130 CONTINUE                                                   USREQ7
      AEQ(3,NGLP1)=RUSER(6)                                      USREQ8
  800 RETURN                                                     USREQ9
      END                                                        USREQ0
      FUNCTION USEREX (IROW,T,MY)                                USREX3
      DOUBLE PRECISION PRECIS, RANGE                             USREX4
      LOGICAL DOMOM, DOUSIN, DOUSNQ, DOUSOU, LAST, NONNEG, ONLY1, PRWT, USREX5
     1 PRY, SIMULA, LUSER                                        USREX6
      DIMENSION T(MY)                                            USREX7
      COMMON /SBLOCK/ PRECIS, RANGE, SRMIN,                      USREX8
     1 ALPST(2), GMNMX(2), PLEVEL(2,2), RSVMNX(2,2), RUSER(100), USREX9
     2 EXMAX, SRANGE                                             USREX0
      COMMON /IBLOCK/ IGRID, IPLRES, IPRINT, IQUAD, IUNIT, IWT,  USREX1
     1 LINEPG, MIOERR, MQPITR, NEQ, NERFIT, NG, NINTT, NLINF, NORDER, USREX2
     2 ICRIT(2), IPLFIT(2),
     3  IUSER(50), LSIGN(4,4), MOMNMX(2), NENDZ(2),              USREX4
     4 NFLAT(4,2), NGL, NGLP1, NIN, NINEQ, NNSGN(2), NOUT, NQPROG(2), USREX5
     5 NSGN(4), NY                                               USREX6
      COMMON /LBLOCK/ DOMOM, DOUSIN, DOUSNQ, DOUSOU, LAST, NONNEG, USREX7
     1 ONLY1, PRWT, PRY, SIMULA,                                 USREX8
     2 LUSER(30)                                                 USREX9
      EX=RUSER(5)*T(IROW)                                        USREX6
      USEREX=RUSER(9)                                            USREX7
      IF (EX .LT. EXMAX)  USEREX=USEREX+RUSER(4)*EXP(-EX)        USREX8
      RETURN                                                     USREX9
      END                                                        USREX0
      SUBROUTINE USERGR (G,CQUAD,MG)                             USRGR2
      DOUBLE PRECISION PRECIS, RANGE                             USRGR3
      LOGICAL DOMOM, DOUSIN, DOUSNQ, DOUSOU, LAST, NONNEG, ONLY1, PRWT, USRGR4
     1 PRY, SIMULA, LUSER                                        USRGR5
      DIMENSION G(MG), CQUAD(MG)                                 USRGR6
      COMMON /SBLOCK/ PRECIS, RANGE, SRMIN,                      USRGR7
     1 ALPST(2), GMNMX(2), PLEVEL(2,2), RSVMNX(2,2), RUSER(100), USRGR8
     2 EXMAX, SRANGE                                             USRGR9
      COMMON /IBLOCK/ IGRID, IPLRES, IPRINT, IQUAD, IUNIT, IWT,  USRGR0
     1 LINEPG, MIOERR, MQPITR, NEQ, NERFIT, NG, NINTT, NLINF, NORDER, USRGR1
     2 ICRIT(2), IPLFIT(2),
     3  IUSER(50), LSIGN(4,4), MOMNMX(2), NENDZ(2),              USRGR3
     4 NFLAT(4,2), NGL, NGLP1, NIN, NINEQ, NNSGN(2), NOUT, NQPROG(2), USRGR4
     5 NSGN(4), NY                                               USRGR5
      COMMON /LBLOCK/ DOMOM, DOUSIN, DOUSNQ, DOUSOU, LAST, NONNEG, USRGR6
     1 ONLY1, PRWT, PRY, SIMULA,                                 USRGR7
     2 LUSER(30)                                                 USRGR8
      READ (NIN,5100) (G(J),J=1,NG)                              USRGR3
 5100 FORMAT (5E15.6)                                            USRGR4
      CALL CQTRAP (G,CQUAD,NG)                                   USRGR8
      RETURN                                                     USRGR9
      END                                                        USRGR0
      SUBROUTINE USERIN (T,Y,SQRTW,MY)                           USRIN3
      DOUBLE PRECISION PRECIS, RANGE                             USRIN4
      LOGICAL DOMOM, DOUSIN, DOUSNQ, DOUSOU, LAST, NONNEG, ONLY1, PRWT, USRIN5
     1 PRY, SIMULA, LUSER                                        USRIN6
      DIMENSION T(MY), Y(MY), SQRTW(MY)                          USRIN7
      COMMON /SBLOCK/ PRECIS, RANGE, SRMIN,                      USRIN8
     1 ALPST(2), GMNMX(2), PLEVEL(2,2), RSVMNX(2,2), RUSER(100), USRIN9
     2 EXMAX, SRANGE                                             USRIN0
      COMMON /IBLOCK/ IGRID, IPLRES, IPRINT, IQUAD, IUNIT, IWT,  USRIN1
     1 LINEPG, MIOERR, MQPITR, NEQ, NERFIT, NG, NINTT, NLINF, NORDER, USRIN2
     2 ICRIT(2), IPLFIT(2),
     3  IUSER(50), LSIGN(4,4), MOMNMX(2), NENDZ(2),              USRIN4
```

```
      4 NFLAT(4,2), NGL, NGLP1, NIN, NINEQ, NNSGN(2), NOUT, NQPROG(2),    USRIN5
      5 NSGN(4), NY                                                       USRIN6
       COMMON /LBLOCK/ DOMOM, DOUSIN, DOUSNQ, DOUSOU, LAST, NONNEG,        USRIN7
      1 ONLY1, PRWT, PRY, SIMULA,                                         USRIN8
      2 LUSER(30)                                                          USRIN9
C
       HFANG=RUSER(12)*8.7266464E-3
       QK=4.E0*3.1415927*SIN(HFANG)*RUSER(14)/RUSER(13)
       RUSER(20)=QK
       DC=1.380622E10*(RUSER(10)+2.7316E2)/(6.E0*3.1415927*RUSER(11))
       Q2DC=QK*QK*DC
C
C   SOME OF THESE ADDED LINES ARE TO IMPLEMENT FINDING SIMULTANEOUS
C   SOLUTIONS OF DATA COLLECTED AT DIFFERENT ANGLES
C
       IEND=NY
       IF(.NOT.LUSER(11)) GO TO 1
       HFANG2=RUSER(17)*8.7266464E-3
       QK2=QK*SIN(HFANG2)/SIN(HFANG)
       RUSER(21)=QK2
       Q2DC2=QK2*QK2*DC
       IEND=IUSER(11)-1
       ISTART=IUSER(11)
C
     1 DO 2 J=1,IEND
     2 Y(J)=Y(J)-RUSER(15)
       IF(.NOT.LUSER(11)) GO TO 6
       DO 3 J=ISTART,NY
     3 Y(J)=Y(J)-RUSER(16)
C
C   ADDED SECTION TO EXTRAPOLATE TO ACF(0) TO GET TRUE AMPLITUDE.
C   EXTRAPOLATION IS BASED ON THE FIRST 4 DATA POINTS.
C
     6 NEXTR=IUSER(12)
       CALL EXTRP(T,Y,1,NEXTR,YNORM)
       YNORM=SQRT(1./YNORM)
       RUSER(22)=YNORM
       IF(.NOT.LUSER(11)) GO TO 4
       CALL EXTRP(T,Y,ISTART,NEXTR,YNORM2)
       YNORM2=SQRT(1./YNORM2)
       RUSER(23)=YNORM2/SQRT(RUSER(18))
C
     4 IF(LUSER(16)) GO TO 5
       DO 110 J=1,NY
       Y(J)=SIGN(SQRT(ABS(Y(J))),Y(J))
   110 CONTINUE
C
     5 DO 10 K=1,IEND
    10 T(K)=T(K)*Q2DC
       DO 15 K=1,IEND
    15 Y(K)=Y(K)*YNORM
       IF(.NOT.LUSER(11)) GO TO 800
C
       DO 11 K=ISTART,NY
    11 T(K)=T(K)*Q2DC2
       DO 16 K=ISTART,NY
    16 Y(K)=Y(K)*YNORM2
C
C   THE FOLLOWING LINES ARE NOT VERY USEFUL. THEY WERE ADDED TO ALLOW
C   WEIGHTING OUT OF ONE OF THE TWO SETS OF DATA IN SIMULTANEOUS TWO
C   ANGLE FITS. THEY SHOULD BE REPLACED BY A WEIGHTING SCHEME TO
C   CORRECTLY WEIGHT THE DATA FROM THE TWO ANGLE BY THE TOTAL SCATTERED
C   INTENSITY.
C
       IF(.NOT.LUSER(12)) GO TO 800
       DO 23 J=1,IEND
    23 SQRTW(J)=1.
       DO 25 J=ISTART,NY
    25 SQRTW(J)=RUSER(25)
       IF(.NOT.LUSER(14)) GO TO 800
       DO 27 J=1,IEND
    27 SQRTW(J)=RUSER(26)
       DO 28 J=ISTART,NY
```

```
   28 SQRTW(J)=1.
  800 CONTINUE                                                                  USRIN7
      RETURN
      END                                                                       USRIN8
      SUBROUTINE EXTRP(T,Y,IFIRST,NEXTR,COEFF1)
      REAL T(1), Y(1)
      DOUBLE PRECISION AEXTR(2,2), AEX(2,2), B1, B2, DENOM
      AEXTR(1,2)=0.
      AEXTR(2,2)=0.
      B1=0.
      B2=0.
      DO 100 J=IFIRST,IFIRST+NEXTR-1
         AEXTR(1,2)=AEXTR(1,2)+T(J)
         AEXTR(2,2)=AEXTR(2,2)+T(J)*T(J)
         B1=B1+Y(J)
         B2=B2+Y(J)*T(J)
  100 CONTINUE
      AEXTR(1,1)=NEXTR
      AEXTR(2,1)=AEXTR(1,2)
      DO 110 I=1,2
      DO 110 J=1,2
         AEX(I,J)=AEXTR(I,J)
  110 CONTINUE
      DENOM=AEX(1,1)*AEX(2,2)-AEX(1,2)*AEX(2,1)
      AEX(1,1)=B1
      AEX(2,1)=B2
      AEX(1,2)=AEXTR(1,2)
      AEX(2,2)=AEXTR(2,2)
      COEFF1=(AEX(1,1)*AEX(2,2)-AEX(1,2)*AEX(2,1))/DENOM
      RETURN
      END
      FUNCTION USERK (JT,T,JG,G)                                                USERK1
      REAL MIE
      DOUBLE PRECISION PRECIS, RANGE                                            USERK2
      LOGICAL DOMOM, DOUSIN, DOUSNQ, DOUSOU, LAST, NONNEG, ONLY1, PRWT,         USERK3
     1 PRY, SIMULA, LUSER                                                       USERK4
      DIMENSION T(JT), G(JG)                                                    USERK5
      CHARACTER IHOLER(6)
      COMMON /SBLOCK/ PRECIS, RANGE, SRMIN,                                     USERK7
     1 ALPST(2), GMNMX(2), PLEVEL(2,2), RSVMNX(2,2), RUSER(100),                USERK8
     2 EXMAX, SRANGE                                                            USERK9
      COMMON /IBLOCK/ IGRID, IPLRES, IPRINT, IQUAD, IUNIT, IWT,                 USERK0
     1 LINEPG, MIOERR, MOPITR, NEQ, NERFIT, NG, NINTT, NLINF, NORDER,           USERK1
     2 ICRIT(2), IPLFIT(2),
     3  IUSER(50), LSIGN(4,4), MOMNMX(2), NENDZ(2),                             USERK3
     4 NFLAT(4,2), NGL, NGLP1, NIN, NINEQ, NNSGN(2), NOUT, NQPROG(2),           USERK4
     5 NSGN(4), NY                                                              USERK5
      COMMON /LBLOCK/ DOMOM, DOUSIN, DOUSNQ, DOUSOU, LAST, NONNEG,              USERK6
     1 ONLY1, PRWT, PRY, SIMULA,                                                USERK7
     2 LUSER(30)                                                                USERK8
      DATA IHOLER/'U','S','E','R','K',' '/                                      USERK9
      IF (JT.GT.NY .OR. JG.GT.NG .OR. MINO(JT,JG).LE.0)   CALL ERRMES (1,USERK0
     1.TRUE.,IHOLER,NOUT)                                                       USERK1
      EX=T(JT)/G(JG)                                                            USERK5
      R=G(JG)*1E-3
      USERK=0.                                                                  USERK6
      IF (EX .GT. EXMAX) RETURN
      WGHT=1.
      IF (LUSER(15)) GO TO 4
      IF(.NOT.LUSER(11)) GO TO 5
    4 WGHT=1.
      IF(JT.LT.IUSER(11)) WGHT=WGHT*RUSER(22)
      IF(JT.GE.IUSER(11)) WGHT=WGHT*RUSER(23)
    5 USERK=WGHT*EXP(-EX)
      RETURN                                                                    USERK8
      END                                                                       USERK9
c   mie.fs
c
c   Userk.mie calculates the size parameter (x) and relative
c   refractive index (refrel) for a given sphere refractive
c   index, medium refractive index, radius, and free space
c   wavelength. It then calls bhmie, the subroutine that computes
c   the amplitude scatering matrix and efficiencies.
```

```
c
      real function mie(radius,ruser,iangle)
      parameter (maxang=1)
      real theta(10), ruser(100)
      complex refrel,s1(maxang),s2(maxang)
c
c   refmed = (real) refractive index of surrounding medium.
c
      refmed=ruser(14)
c
c   refractive index of sphere = refre + i*refim.  For now, assume PSL.
c
      refre=1.6
      refim=0.0
      refrel=cmplx(refre,refim)/refmed
c
c   Radius (rad) and wavelength (wavel) same units.  Get various quantities
c   ready to call bhmie.
c
      wavel=ruser(13)
      x=2.*3.14159265*radius*refmed/wavel
      nang=1
      convrt=1.7453293e-2
      theta(1)=ruser(iangle)*convrt
      call bhmie(theta,x,refrel,nang,s1,s2,qext,qsca,qback)
c
c   s1 and s2 are used to calculate the (perpendicular) mie intensities.
c
      do 10 j=1,nang
         s11=0.5*cabs(s2(j))*cabs(s2(j))
         s11=s11+0.5*cabs(s1(j))*cabs(s1(j))
         s12=0.5*cabs(s2(j))*cabs(s2(j))
         s12=s12-0.5*cabs(s1(j))*cabs(s1(j))
         mie=s11-s12
   10 continue
      return
      end
c
c   Subroutine bhmie calculates amplitude scattering matrix
c   elements and efficiencies for extinction, total scattering
c   and backscattering for a given size parameter and
c   relative refractie index.
c
      subroutine bhmie(theta,x,refrel,nang,s1,s2,qext,qsca,qback)
      parameter (maxang=1)
      dimension amu(10),theta(10),pi(10),tau(10),pi0(10),pi1(10)
      complex d(300),y,refrel,xi,xi0,xi1,an,bn,s1(maxang),s2(maxang)
      double precision psi0,psi1,psi,dn,dx
      dx=x
      y=x*refrel
c
c   Series terminated after nstop terms.
c
      xstop=x+4.*x**.3333+2.0
      nstop=xstop
      ymod=cabs(y)
      nmx=amax1(xstop,ymod)+15
      dang=1.570796327/float(nang-1)
      do 555 j=1,nang
  555 amu(j)=cos(theta(j))
c
c   Logarithmic derivative d(j) calculated by downward
c   recurrence beginning with initial alue 0.0 + i*0.0
c   at j=nmx
c
      d(nmx)=cmplx(0.0,0.0)
      nn=nmx-1
      do 120 n=1,nn
      rn=nmx-n+1
  120 d(nmx-n)=(rn/y)-(1./(d(nmx-n+1)+rn/y))
      do 666 j=1,nang
      pi0(j)=0.0
  666 pi1(j)=1.0
```

```
      nn=2*nang-1
      do 777 j=1,nn
      s1(j)=cmplx(0.0,0.0)
  777 s2(j)=cmplx(0.0,0.0)
c
c   Ricatti-Bessel functions with real arguement x
c   calculated by upward recurrence.
c
      psi0=dcos(dx)
      psi1=dsin(dx)
      chi0=-sin(x)
      chi1=cos(x)
      apsi0=psi0
      apsi1=psi1
      xi0=cmplx(apsi0,-chi0)
      xi1=cmplx(apsi1,-chi1)
      qsca=0.0
      n=1
  200 dn=n
      rn=n
      fn=(2.*rn+1.)/(rn*(rn+1.))
      psi=(2.*dn-1.)*psi1/dx-psi0
      apsi=psi
      chi=(2.*rn-1.)*chi1/x-chi0
      xi=cmplx(apsi,-chi)
      an=(d(n)/refrel+rn/x)*apsi-apsi1
      an=an/((d(n)/refrel+rn/x)*xi-xi1)
      bn=(refrel*d(n)+rn/x)*apsi-apsi1
      bn=bn/((refrel*d(n)+rn/x)*xi-xi1)
      qsca=qsca+(2.*rn+1.)*(cabs(an)*cabs(an)+cabs(bn)*cabs(bn))
      do 789 j=1,nang
      jj=2*nang-j
      pi(j)=pi1(j)
      tau(j)=rn*amu(j)*pi(j)-(rn+1.)*pi0(j)
      p=(-1.)**(n-1)
      s1(j)=s1(j)+fn*(an*pi(j)+bn*tau(j))
      t=(-1.)**n
      s2(j)=s2(j)+fn*(an*tau(j)+bn*pi(j))
      if(j.eq.jj) go to 789
      s1(jj)=s1(jj)+fn*(an*pi(j)*p+bn*tau(j)*t)
      s2(jj)=s2(jj)+fn*(an*tau(j)*t+bn*pi(j)*p)
  789 continue
      psi0=psi1
      psi1=psi
      apsi1=psi1
      chi0=chi1
      chi1=chi
      xi1=cmplx(apsi1,-chi1)
      n=n+1
      rn=n
      do 999 j=1,nang
      pi1(j)=((2.*rn-1.)/(rn-1.))*amu(j)*pi(j)
      pi1(j)=pi1(j)-rn*pi0(j)/(rn-1.)
  999 pi0(j)=pi(j)
      if(n-1-nstop) 200,300,300
  300 qsca=(2./(x*x))*qsca
      qext=(4./(x*x))*real(s1(1))
      qback=(4./(x*x))*cabs(s1(2*nang-1))*cabs(s1(2*nang-1))
      return
      end
      SUBROUTINE USERNQ (AINEQ,MG,MINEQ)                                USRNQ8
      DOUBLE PRECISION PRECIS, RANGE                                    USRNQ9
      DOUBLE PRECISION AINEQ, ONE, ZERO                                 USRNQ0
      LOGICAL DOMOM, DOUSIN, DOUSNQ, DOUSOU, LAST, NONNEG, ONLY1, PRWT, USRNQ1
     1 PRY, SIMULA, LUSER                                               USRNQ2
      DIMENSION AINEQ(MINEQ,MG)                                         USRNQ3
      COMMON /SBLOCK/ PRECIS, RANGE, SRMIN,                             USRNQ4
     1 ALPST(2), GMNMX(2), PLEVEL(2,2), RSVMNX(2,2), RUSER(100),        USRNQ5
     2 EXMAX, SRANGE                                                    USRNQ6
      COMMON /IBLOCK/ IGRID, IPLRES, IPRINT, IQUAD, IUNIT, IWT,         USRNQ7
     1 LINEPG, MIDERR, MQFITR, NEQ, NERFIT, NG, NINTT, NLINF, NORDER,   USRNQ8
     2 ICRIT(2), IPLFIT(2),
     3 IUSER(50), LSIGN(4,4), MOMNMX(2), NENDZ(2),                      USRNQ0
```

```
      4 NFLAT(4,2), NGL, NGLP1, NIN, NINEQ, NNSGN(2), NOUT, NQPROG(2),    USRNQ1
      5 NSGN(4), NY                                                        USRNQ2
        COMMON /LBLOCK/ DOMOM, DOUSIN, DOUSNQ, DOUSOU, LAST, NONNEG,        USRNQ3
      1 ONLY1, PRWT, PRY, SIMULA,                                          USRNQ4
      2 LUSER(30)                                                          USRNQ5
        ZERO=0.D0                                                          USRNQ7
        ONE=1.D0                                                           USRNQ9
        IF (NLINF .LE. 0) RETURN                                           USRNQ4
        NINEQ=NLINF                                                        USRNQ5
        DO 110 J=1,NINEQ                                                   USRNQ6
          DO 120 K=1,NGLP1                                                 USRNQ7
            AINEQ(J,K)=ZERO                                                USRNQ8
  120   CONTINUE                                                           USRNQ9
        K=NG+J                                                             USRNQO
        AINEQ(J,K)=ONE                                                     USRNQ1
  110 CONTINUE                                                             USRNQ2
      RETURN                                                               USRNQ3
      END                                                                  USRNQ4
      SUBROUTINE USEROU (G,SOL,EXACT,MG)                                   USROU1
      DOUBLE PRECISION PRECIS, RANGE                                       USROU2
      LOGICAL DOMOM, DOUSIN, DOUSNQ, DOUSOU, LAST, NONNEG, ONLY1, PRWT,    USROU3
    1 PRY, SIMULA, LUSER                                                   USROU4
      DIMENSION G(MG), SOL(MG), EXACT(MG)                                  USROU5
      DIMENSION FCAP(4,16), F(4)                                           USROU3
      COMMON /SBLOCK/ PRECIS, RANGE, SRMIN,                                USROU4
    1 ALPST(2), GMNMX(2), PLEVEL(2,2), RSVMNX(2,2), RUSER(100),            USROU5
    2 EXMAX, SRANGE                                                        USROU6
      COMMON /IBLOCK/ IGRID, IPLRES, IPRINT, IQUAD, IUNIT, IWT,            USROU7
    1 LINEPG, MIOERR, MQPITR, NEQ, NERFIT, NG, NINTT, NLINF, NORDER,       USROU8
    2 ICRIT(2), IPLFIT(2),
    3  IUSER(50), LSIGN(4,4), MOMNMX(2), NENDZ(2),                         USROUO
    4 NFLAT(4,2), NGL, NGLP1, NIN, NINEQ, NNSGN(2), NOUT, NQPROG(2),       USROU1
    5 NSGN(4), NY                                                          USROU2
      COMMON /LBLOCK/ DOMOM, DOUSIN, DOUSNQ, DOUSOU, LAST, NONNEG,         USROU3
    1 ONLY1, PRWT, PRY, SIMULA,                                            USROU4
    2 LUSER(30)                                                            USROU5
      DATA NSPECT/16/, NCLASS/4/, FCAP/                                    USROU6
    1      .79,.00,.05,.16 ,   .41,.16,.23,.20 ,    .23,.40,.13,.24 ,      USROU7
    2      .28,.14,.17,.41 ,   .45,.24,.06,.25 ,    .09,.34,.34,.23 ,      USROU8
    3      .02,.51,.09,.38 ,   .39,.00,.24,.37 ,    .07,.52,.26,.15 ,      USROU9
    4      .24,.15,.18,.43 ,   .51,.24,.12,.13 ,    .62,.05,.17,.16 ,      USROUO
    5      .37,.15,.26,.22 ,                        .28,.33,.03,.36 ,      USROU1
    6                          .54,.12,.19,.15 ,    .26,.44,.13,.17 /      USROU2
      SUMF=0.                                                              USROU3
      DO 110 J=1,NCLASS                                                    USROU4
        F(J)=0.                                                            USROU5
        DO 120 K=1,NSPECT                                                  USROU6
          F(J)=F(J)+SOL(K)*FCAP(J,K)                                       USROU7
  120   CONTINUE                                                           USROU8
        SUMF=SUMF+F(J)                                                     USROU9
  110 CONTINUE                                                             USROUO
      DO 140 J=1,NCLASS                                                    USROU1
        F(J)=F(J)/SUMF                                                     USROU2
  140 CONTINUE                                                             USROU3
      SUMF=SUMF/RUSER(14)                                                  USROU4
 5140 FORMAT (/8X,'HELIX',3X,'BETA-SHEET',4X,'BETA-TURN',4X,               USROU9
    1 'REMAINDER',6X,'SCALE FACTOR'/4F13.2,F18.3)                          USROUO
      WRITE (NOUT,5140) F,SUMF                                             USROU1
      RETURN                                                               USROU2
      END                                                                  USROU3
      SUBROUTINE USERRG (REG,MREG,MG,NREG)                                 USRRG2
      DOUBLE PRECISION PRECIS, RANGE                                       USRRG3
      DOUBLE PRECISION REG                                                 USRRG4
      LOGICAL DOMOM, DOUSIN, DOUSNQ, DOUSOU, LAST, NONNEG, ONLY1, PRWT,    USRRG5
    1 PRY, SIMULA, LUSER                                                   USRRG6
      DIMENSION REG(MREG,MG)                                               USRRG7
      COMMON /SBLOCK/ PRECIS, RANGE, SRMIN,                                USRRG8
    1 ALPST(2), GMNMX(2), PLEVEL(2,2), RSVMNX(2,2), RUSER(100),            USRRG9
    2 EXMAX, SRANGE                                                        USRRGO
      COMMON /IBLOCK/ IGRID, IPLRES, IPRINT, IQUAD, IUNIT, IWT,            USRRG1
    1 LINEPG, MIOERR, MQPITR, NEQ, NERFIT, NG, NINTT, NLINF, NORDER,       USRRG2
    2 ICRIT(2), IPLFIT(2),
    3  IUSER(50), LSIGN(4,4), MOMNMX(2), NENDZ(2),                         USRRG4
```

```
      4 NFLAT(4,2), NGL, NGLP1, NIN, NINEQ, NNSGN(2), NOUT, NQPROG(2),       USRRG5
      5 NSGN(4), NY                                                          USRRG6
        COMMON /LBLOCK/ DOMOM, DOUSIN, DOUSNQ, DOUSOU, LAST, NONNEG,          USRRG7
      1 ONLY1, PRWT, PRY, SIMULA,                                            USRRG8
      2 LUSER(30)                                                             USRRG9
        NREG=NG                                                              USRRG4
        DO 110 J=1,NREG                                                       USRRG5
          DO 120 K=1,NGL                                                      USRRG6
            REG(J,K)=0.                                                       USRRG7
  120     CONTINUE                                                            USRRG8
          REG(J,J)=1.                                                         USRRG9
  110   CONTINUE                                                              USRRG0
        J=IUSER(1)                                                            USRRG1
        K=J+NG-1                                                              USRRG2
        IF (LUSER(1)) GO TO 200                                               USRRG3
 5200   FORMAT (5E15.6)                                                       USRRG4
        READ (NIN,5200) (RUSER(L),L=J,K)                                      USRRG5
        WRITE (NOUT,5200) (RUSER(L),L=J,K)                                    USRRG6
        LUSER(1)=.TRUE.                                                       USRRG7
  200   IROW=0                                                                USRRG8
        DO 210 L=J,K                                                          USRRG9
          IROW=IROW+1                                                         USRRG0
          REG(IROW,NGLP1)=RUSER(L)                                            USRRG1
  210   CONTINUE                                                              USRRG2
        RETURN                                                                USRRG3
        END                                                                   USRRG4
        SUBROUTINE USERSI (EXACT,MY,T,Y)                                      USRSI1
        DOUBLE PRECISION PRECIS, RANGE                                        USRSI2
        DOUBLE PRECISION DUB                                                  USRSI3
        LOGICAL DOMOM, DOUSIN, DOUSNQ, DOUSOU, LAST, NONNEG, ONLY1, PRWT,     USRSI4
      1 PRY, SIMULA, LUSER                                                    USRSI5
        CHARACTER IFORMT(70), IFORMW(70), IFORMY(70),LA(6,46), ITITLE(80)
        DIMENSION T(MY), EXACT(MY), Y(MY)                                     USRSI6
        DIMENSION RN(2)                                                       USRSI7
        COMMON /CBLOCK/ IFORMT, IFORMW, IFORMY,LA, ITITLE
        COMMON /SBLOCK/ PRECIS, RANGE, SRMIN,                                 USRSI8
      1 ALPST(2), GMNMX(2), PLEVEL(2,2), RSVMNX(2,2), RUSER(100),             USRSI9
      2 EXMAX, SRANGE                                                         USRSI0
        COMMON /IBLOCK/ IGRID, IPLRES, IPRINT, IQUAD, IUNIT, IWT,             USRSI1
      1 LINEPG, MIOERR, MQPITR, NEQ, NERFIT, NG, NINTT, NLINF, NORDER,        USRSI2
      2 ICRIT(2), IPLFIT(2),
      3 IUSER(50), LSIGN(4,4), MOMNMX(2), NENDZ(2),                           USRSI4
      4 NFLAT(4,2), NGL, NGLP1, NIN, NINEQ, NNSGN(2), NOUT, NQPROG(2),        USRSI5
      5 NSGN(4), NY                                                           USRSI6
        COMMON /LBLOCK/ DOMOM, DOUSIN, DOUSNQ, DOUSOU, LAST, NONNEG,          USRSI7
      1 ONLY1, PRWT, PRY, SIMULA,                                             USRSI8
      2 LUSER(30)                                                             USRSI9
        TWOPI=6.283185307200                                                  USRSI0
        DUB=DBLE(FLOAT(IUSER(3)))                                             USRSI1
        L=NY                                                                  USRSI2
        DO 150 J=1,L                                                          USRSI3
          JJ=J                                                                USRSI4
          EXACT(J)=1.+USEREX(JJ,T,MY)**2                                      USRSI0
          K=2-MOD(J,2)                                                        USRSI5
          IF (K .EQ. 1) CALL RGAUSS (RN(1),RN(2),TWOPI,DUB)                   USRSI6
          Y(J)=EXACT(J)+RUSER(3)*RN(K)*SQRT(EXACT(J))                         USRSI5
          EXACT(J)=SIGN(SQRT(ABS(EXACT(J)-1.)),EXACT(J)-1.)                   USRSI4
          Y(J)=SIGN(SQRT(ABS(Y(J)-1.)),Y(J)-1.)                               USRSI5
  150   CONTINUE                                                              USRSI6
        RETURN                                                                USRSI7
        END                                                                   USRSI8
        SUBROUTINE USERSX (EXACT,G,MG)                                        USRSX6
        DOUBLE PRECISION PRECIS, RANGE                                        USRSX7
        LOGICAL DOMOM, DOUSIN, DOUSNQ, DOUSOU, LAST, NONNEG, ONLY1, PRWT,     USRSX8
      1 PRY, SIMULA, LUSER                                                    USRSX9
        DIMENSION EXACT(MG), G(MG)                                            USRSX0
        COMMON /SBLOCK/ PRECIS, RANGE, SRMIN,                                 USRSX1
      1 ALPST(2), GMNMX(2), PLEVEL(2,2), RSVMNX(2,2), RUSER(100),             USRSX2
      2 EXMAX, SRANGE                                                         USRSX3
        COMMON /IBLOCK/ IGRID, IPLRES, IPRINT, IQUAD, IUNIT, IWT,             USRSX4
      1 LINEPG, MIOERR, MQPITR, NEQ, NERFIT, NG, NINTT, NLINF, NORDER,        USRSX5
      2 ICRIT(2), IPLFIT(2),
```

```
      3 IUSER(50), LSIGN(4,4), MOMNMX(2), NENDZ(2),
      4 NFLAT(4,2), NGL, NGLP1, NIN, NINEQ, NNSGN(2), NOUT, NQPROG(2),        USRSX8
      5 NSGN(4), NY                                                           USRSX9
        COMMON /LBLOCK/ DOMOM, DOUSIN, DOUSNQ, DOUSOU, LAST, NONNEG,          USRSX0
      1 ONLY1, PRWT, PRY, SIMULA,                                             USRSX1
      2 LUSER(30)                                                             USRSX2
        IF (RUSER(8).GE.1. .AND. RUSER(8).LE.20.)   GO TO 120                 USRSX7
 5120 FORMAT (/' RUSER(8) =',E12.4,' IS OUT OF RANGE IN USERSX.')             USRSX8
        WRITE (NOUT,5120) RUSER(8)                                            USRSX9
        STOP                                                                  USRSX0
  120 EXMIN=-ALOG(SRANGE)                                                     USRSX1
      FACTL=GAMLN(RUSER(8)+1.)                                                USRSX2
      DO 150 J=1,NG                                                           USRSX3
         EXACT(J)=0.                                                          USRSX4
         IF (G(J))  160,150,180                                               USRSX5
  160    WRITE (NOUT,5160)                                                    USRSX6
 5160    FORMAT (/' NEGATIVE G IN USEREX.')                                   USRSX7
         STOP                                                                 USRSX8
  180    EX=RUSER(8)*ALOG(G(J))-G(J)-FACTL                                    USRSX9
         IF (EX .GE. EXMIN)   EXACT(J)=EXP(EX)                                USRSX0
  150 CONTINUE                                                                USRSX1
      RETURN                                                                  USRSX2
      END                                                                     USRSX3
      FUNCTION USERTR (X,IFUNCT)                                              USRTR8
      DOUBLE PRECISION PRECIS, RANGE                                          USRTR9
      LOGICAL DOMOM, DOUSIN, DOUSNQ, DOUSOU, LAST, NONNEG, ONLY1, PRWT,       USRTR0
     1 PRY, SIMULA, LUSER                                                     USRTR1
      COMMON /SBLOCK/ PRECIS, RANGE, SRMIN,                                   USRTR2
     1 ALPST(2), GMNMX(2), PLEVEL(2,2), RSVMNX(2,2), RUSER(100),              USRTR3
     2 EXMAX, SRANGE                                                          USRTR4
      COMMON /IBLOCK/ IGRID, IPLRES, IPRINT, IQUAD, IUNIT, IWT,               USRTR5
     1 LINEPG, MIOERR, MQPITR, NEQ, NERFIT, NG, NINTT, NLINF, NORDER,         USRTR6
     2 ICRIT(2), IPLFIT(2),
     3 IUSER(50), LSIGN(4,4), MOMNMX(2), NENDZ(2),
     4 NFLAT(4,2), NGL, NGLP1, NIN, NINEQ, NNSGN(2), NOUT, NQPROG(2),         USRTR9
     5 NSGN(4), NY                                                            USRTR0
      COMMON /LBLOCK/ DOMOM, DOUSIN, DOUSNQ, DOUSOU, LAST, NONNEG,            USRTR1
     1 ONLY1, PRWT, PRY, SIMULA,                                              USRTR2
     2 LUSER(30)                                                              USRTR3
      CHARACTER IHOLER(6)                                                     USRTR4
      DATA IHOLER/'U','S','E','R','T','R'/                                    USRTR5
      IF (IFUNCT.LT.1 .OR. IFUNCT.GT.3)   CALL ERRMES (1,.TRUE., IHOLER,      USRTR6
     1NOUT)                                                                   USRTR7
      IF (IGRID .NE. 1)   GO TO 200                                           USRTR8
      USERTR=1.                                                               USRTR3
      IF (IFUNCT .NE. 3)   USERTR=X                                           USRTR4
      RETURN                                                                  USRTR5
  200 IF (IGRID .NE. 2)   CALL ERRMES (2,.TRUE.,IHOLER,NOUT)                  USRTR6
      GO TO (210,220,230),IFUNCT                                              USRTR7
  210 USERTR=ALOG(X)                                                          USRTR1
      RETURN                                                                  USRTR2
  220 USERTR=EXP(X)                                                           USRTR6
      RETURN                                                                  USRTR7
  230 USERTR=1./X                                                             USRTR1
      RETURN                                                                  USRTR2
      END                                                                     USRTR3
      SUBROUTINE USERWT (Y,YLYFIT,MY,ERRFIT,SQRTW)                            USRWT1
      DOUBLE PRECISION PRECIS, RANGE                                          USRWT2
      LOGICAL DOMOM, DOUSIN, DOUSNQ, DOUSOU, LAST, NONNEG, ONLY1, PRWT,       USRWT3
     1 PRY, SIMULA, LUSER                                                     USRWT4
      DIMENSION Y(MY), YLYFIT(MY), SQRTW(MY)                                  USRWT5
      COMMON /SBLOCK/ PRECIS, RANGE, SRMIN,                                   USRWT6
     1 ALPST(2), GMNMX(2), PLEVEL(2,2), RSVMNX(2,2), RUSER(100),              USRWT7
     2 EXMAX, SRANGE                                                          USRWT8
      COMMON /IBLOCK/ IGRID, IPLRES, IPRINT, IQUAD, IUNIT, IWT,               USRWT9
     1 LINEPG, MIOERR, MQPITR, NEQ, NERFIT, NG, NINTT, NLINF, NORDER,         USRWT0
     2 ICRIT(2), IPLFIT(2),
     3 IUSER(50), LSIGN(4,4), MOMNMX(2), NENDZ(2),
     4 NFLAT(4,2), NGL, NGLP1, NIN, NINEQ, NNSGN(2), NOUT, NQPROG(2),         USRWT3
     5 NSGN(4), NY                                                            USRWT4
      COMMON /LBLOCK/ DOMOM, DOUSIN, DOUSNQ, DOUSOU, LAST, NONNEG,            USRWT5
```

```
      1 ONLY1, PRWT, PRY, SIMULA,                                      USRWT6
      2 LUSER(30)                                                      USRWT7
         DO 110 J=1,NY                                                  USRWT2
            DUM=AMAX1(ABS(Y(J)-YLYFIT(J)),ERRFIT)                       USRWT3
            SQRTW(J)=2.*DUM/SQRT(DUM*DUM+1.)                            USRWT4
  110    CONTINUE                                                       USRWT5
         RETURN                                                         USRWT6
         END                                                            USRWT7
         SUBROUTINE WRITIN (EXACT,G,MG,MY,SQRTW,T,Y)
         DOUBLE PRECISION PRECIS, RANGE                                 WRTIN9
         LOGICAL DOMOM, DOUSIN, DOUSNQ, DOUSOU, LAST, NONNEG, ONLY1, PRWT, WRTIN0
      1 PRY, SIMULA, LUSER                                              WRTIN1
         LOGICAL LEQUIV(10)                                             WRTIN2
         DIMENSION EXACT(MY), SQRTW(MY), T(MY), Y(MY)
         DIMENSION IEQUIV(15), G(MG)                                    WRTIN4
         CHARACTER IFORMT(70), IFORMW(70), IFORMY(70), LA(6,46),ITITLE(80)
         COMMON /CBLOCK/ IFORMT, IFORMW, IFORMY, LA, ITITLE
         COMMON /SBLOCK/ PRECIS, RANGE, SRMIN,                          WRTIN5
      1 ALPST(2), GMNMX(2), PLEVEL(2,2), RSVMNX(2,2), RUSER(100),       WRTIN6
      2 EXMAX, SRANGE                                                   WRTIN7
         COMMON /IBLOCK/ IGRID, IPLRES, IPRINT, IQUAD, IUNIT, IWT,      WRTIN8
      1 LINEPG, MIOERR, MQPITR, NEQ, NERFIT, NG, NINTT, NLINF, NORDER,  WRTIN9
      2 ICRIT(2), IPLFIT(2),
      3 IUSER(50), LSIGN(4,4), MOMNMX(2), NENDZ(2),
      4 NFLAT(4,2), NGL, NGLP1, NIN, NINEQ, NNSGN(2), NOUT, NQPROG(2),  WRTIN2
      5 NSGN(4), NY                                                     WRTIN3
         COMMON /LBLOCK/ DOMOM, DOUSIN, DOUSNQ, DOUSOU, LAST, NONNEG,   WRTIN4
      1 ONLY1, PRWT, PRY, SIMULA,                                       WRTIN5
      2 LUSER(30)                                                       WRTIN6
         EQUIVALENCE (IGRID,IEQUIV(1)), (DOMOM,LEQUIV(1))               WRTIN7
 5999 FORMAT ('1')                                                      WRTIN8
         IF (IPRINT .GE. 3) WRITE(NOUT,5999)                            WRTIN9
 5003 FORMAT (//1X)                                                     WRTIN0
         IF (IPRINT .LT. 3) WRITE(NOUT,5003)                            WRTIN1
 5100 FORMAT (40X,'FINAL VALUES OF CONTROL VARIABLES')                  WRTIN2
         WRITE (NOUT,5100)                                              WRTIN3
 5110 FORMAT (1X,6A1,' =',1P10E12.5/(9X,10E12.5))                       WRTIN4
         WRITE (NOUT,5110) (LA(K,1),K=1,6),SRMIN                        WRTIN5
         WRITE (NOUT,5110) (LA(K,2),K=1,6),ALPST                        WRTIN6
         WRITE (NOUT,5110) (LA(K,3),K=1,6),GMNMX                        WRTIN7
         WRITE (NOUT,5110) (LA(K,4),K=1,6),PLEVEL                       WRTIN8
         WRITE (NOUT,5110) (LA(K,5),K=1,6),RSVMNX                       WRTIN9
         WRITE (NOUT,5110) (LA(K,6),K=1,6),RUSER                        WRTIN0
         JJ=6                                                           WRTIN1
 5210 FORMAT (1X,6A1,' =',10I12/(9X,10I12))                             WRTIN2
         DO 210 J=1,15                                                  WRTIN3
            JJ=JJ+1                                                     WRTIN4
            WRITE (NOUT,5210) (LA(K,JJ),K=1,6),IEQUIV(J)                WRTIN5
  210    CONTINUE                                                       WRTIN6
         WRITE (NOUT,5210) (LA(K,22),K=1,6),ICRIT                       WRTIN7
 5220 FORMAT (1X,6A1,' = ',80A1)                                        WRTIN8
         WRITE (NOUT,5220) (LA(K,23),K=1,6),IFORMT                      WRTIN9
         WRITE (NOUT,5220) (LA(K,24),K=1,6),IFORMW                      WRTIN0
         WRITE (NOUT,5220) (LA(K,25),K=1,6),IFORMY                      WRTIN1
         WRITE (NOUT,5210) (LA(K,26),K=1,6),IPLFIT                      WRTIN2
         WRITE (NOUT,5210) (LA(K,27),K=1,6),IUSER                       WRTIN3
         WRITE (NOUT,5210) (LA(K,28),K=1,6),LSIGN                       WRTIN4
         WRITE (NOUT,5210) (LA(K,29),K=1,6),MOMNMX                      WRTIN5
         WRITE (NOUT,5210) (LA(K,30),K=1,6),NENDZ                       WRTIN6
         WRITE (NOUT,5210) (LA(K,31),K=1,6),NFLAT                       WRTIN7
         WRITE (NOUT,5210) (LA(K,32),K=1,6),NNSGN                       WRTIN8
         WRITE (NOUT,5210) (LA(K,33),K=1,6),NQPROG                      WRTIN9
         WRITE (NOUT,5210) (LA(K,34),K=1,6),NSGN                        WRTIN0
         JJ=34                                                          WRTIN1
 5310 FORMAT (1X,6A1,' =',10L12/(9X,10L12))                             WRTIN2
         DO 310 J=1,10                                                  WRTIN3
            JJ=JJ+1                                                     WRTIN4
            WRITE (NOUT,5310) (LA(K,JJ),K=1,6),LEQUIV(J)                WRTIN5
  310    CONTINUE                                                       WRTIN6
         WRITE (NOUT,5310) (LA(K,45),K=1,6),LUSER                       WRTIN7
         IF (.NOT.SIMULA .AND. NY.LE.MY) CALL WRITYT (EXACT, G,IPRINT,IWT,WRTIN8
     1MG,NOUT,NY,PRY,SIMULA,SQRTW,T,Y)                                  WRTIN9
 5320 FORMAT (9HOPRECIS =,1PD9.2,10X,8HSRANGE =,E9.2,                   WRTIN2
```

```
1 5X,'RANGE =',D9.2)                                                    WRTIN3
      WRITE (NOUT,5320) PRECIS, SRANGE, RANGE                           WRTIN4
      RETURN                                                            WRTIN5
      END                                                               WRTIN6
      SUBROUTINE WRITYT (EXACT,G,IPRINT,IWT,MG,NOUT,NY,PRY,SIMULA,      WRTYT6
     1 SQRTW,T,Y)                                                       WRTYT7
      LOGICAL PRY, SIMULA                                               WRTYT8
      DIMENSION EXACT(NY), SQRTW(NY), T(NY), Y(NY), G(MG)               WRTYT9
      IF (.NOT.PRY) GO TO 700                                           WRTYT0
5999  FORMAT ('1')                                                      WRTYT1
      IF (IPRINT .GE. 3)  WRITE (NOUT,5999)                             WRTYT2
5003  FORMAT (//1X)                                                     WRTYT3
      IF (IPRINT .LT. 3)  WRITE(NOUT,5003)                              WRTYT4
      IF (SIMULA) GO TO 200                                             WRTYT5
5110  FORMAT (5(12X,'T',12X,'Y')/(2X,1PE11.3,E13.5,E13.3,E13.5,         WRTYT6
     1 E13.3,E13.5,E13.3,E13.5,E13.3,E13.5))                            WRTYT7
      IF (IWT .NE. 4)  WRITE (NOUT,5110) (T(J),Y(J),J=1,NY)             WRTYT8
5120  FORMAT (3(17X,'T',12X,'Y',8X,'SQRTW')/(5X,1P3E13.5,5X,3E13.5,     WRTYT9
     1 5X,3E13.5))                                                      WRTYT0
      IF (IWT .EQ. 4)  WRITE (NOUT,5120) (T(J),Y(J),SQRTW(J),J=1,NY)    WRTYT1
      GO TO 700                                                         WRTYT2
5210  FORMAT (2(17X,'T',12X,'Y',8X,'EXACT',8X,'ERROR'))                 WRTYT3
 200  IF (IWT .NE. 4)  WRITE (NOUT,5210)                                WRTYT4
5211  FORMAT (2(12X,'T',12X,'Y',8X,'EXACT',8X,'ERROR',8X,               WRTYT5
     1 'SQRTW'))                                                        WRTYT6
      IF (IWT .EQ. 4)  WRITE (NOUT,5211)                                WRTYT7
      DO 210 J=2,NY,2                                                   WRTYT8
        DUM=Y(J-1)-EXACT(J-1)                                           WRTYT9
        DDUM=Y(J)-EXACT(J)                                              WRTYT0
5220    FORMAT (5X,1P4E13.5,5X,4E13.5)                                  WRTYT1
        IF (IWT .NE. 4)  WRITE (NOUT,5220) T(J-1),Y(J-1),EXACT(J-1),DUM,WRTYT2
     1 T(J),Y(J),EXACT(J),DDUM                                          WRTYT3
5221    FORMAT (2X,1PE11.3,4E13.5,E13.3,4E13.5)                         WRTYT4
        IF (IWT .EQ. 4)  WRITE (NOUT,5221) T(J-1),Y(J-1),EXACT(J-1),DUM,WRTYT5
     1 SQRTW(J-1),T(J),Y(J),EXACT(J),DDUM,SQRTW(J)                      WRTYT6
 210  CONTINUE                                                          WRTYT7
      IF (MOD(NY,2) .EQ. 0)  GO TO 700                                  WRTYT8
      DUM=Y(NY)-EXACT(NY)                                               WRTYT9
      IF (IWT .NE. 4)  WRITE (NOUT,5220) T(NY),Y(NY),EXACT(NY),DUM      WRTYT0
      IF (IWT .EQ. 4)  WRITE (NOUT,5221) T(NY),Y(NY),EXACT(NY),DUM,     WRTYT1
     1 SQRTW(NY)                                                        WRTYT2
 700  RETURN                                                            WRTYT3
      END                                                               WRTYT4
      FUNCTION USERLF (JY,JLINF,T,NYDIM)                                USRLF5
      DOUBLE PRECISION PRECIS, RANGE                                    USRLF6
      LOGICAL DOMOM, DOUSIN, DOUSNQ, DOUSOU, LAST, NONNEG, ONLY1, PRWT, USRLF7
     1 PRY, SIMULA, LUSER                                               USRLF8
      DIMENSION T(NYDIM)                                                USRLF9
      CHARACTER IHOLER(6)                                               
      COMMON /SBLOCK/ PRECIS, RANGE, SRMIN,                             USRLF0
     1 ALPST(2), GMNMX(2), PLEVEL(2,2), RSVMNX(2,2), RUSER(100),        USRLF1
     2 EXMAX, SRANGE                                                    USRLF2
      COMMON /IBLOCK/ IGRID, IPLRES, IPRINT, IQUAD, IUNIT, IWT,         USRLF3
     1 LINEPG, MIDERR, MQPITR, NEQ, NERFIT, NG, NINTT, NLINF, NORDER,   USRLF4
     2 ICRIT(2), IPLFIT(2),                                             
     3 IUSER(50), LSIGN(4,4), MOMNMX(2), NENDZ(2),                      
     4 NFLAT(4,2), NGL, NGLP1, NIN, NINEQ, NNSGN(2), NOUT, NQPROG(2),   USRLF7
     5 NSGN(4), NY                                                      USRLF8
      COMMON /LBLOCK/ DOMOM, DOUSIN, DOUSNQ, DOUSOU, LAST, NONNEG,      USRLF9
     1 ONLY1, PRWT, PRY, SIMULA,                                        USRLF0
     2 LUSER(30)                                                        USRLF1
      DATA IHOLER/'U','S','E','R','L','F'/                              USRLF2
      IF (JY.GT.NY .OR. JY.LE.0)  CALL ERRMES (1,.TRUE.,IHOLER,NOUT     USRLF3
      IF (JLINF.LT.1 .OR. JLINF.GT.2)  CALL ERRMES (2,.TRUE.,IHOLER,    USRLF8
     1 NOUT)                                                            USRLF9
      USERLF=0.                                                         USRLF0
      IF ((JY.LE.IUSER(2) .AND. JLINF.EQ.1) .OR. (JY.GT.IUSER(2)        USRLF1
     1 .AND. JLINF.EQ.2) .OR. IUSER(2).LE.0)  USERLF=1.                 USRLF2
      RETURN                                                            USRLF3
      END                                                               USRLF4
```

APPENDIX C

```
c  condense.fm
c
c  This routine takes two 256 channel 1096 data sets and condenses the
c  data to two 60 channel data sets for use in cont2ang.fm
c
      parameter (ntmax=276,nt=256)
      double precision acf(ntmax), acf2(ntmax)
      double precision t(ntmax), t2(ntmax)
      real param(10)
      character*30 label(10)
      character*20 ifile1, ifile2, ofile
      logical last
c
      ifile1='
      ofile=ifile1
      ifile2=ifile1
      print *,'Enter input filename for first angle:'
      read(*,470) ifile1
      print *, 'Enter input filename for second angle:'
      read(*,470) ifile2
      print *,'Enter output filename :'
      read(*,470) ofile
 470  format(a)
      open(1,file=ifile1,status='old')
      open(2,file=ifile2,status='old')
      open(3,file=ofile,status='new')
c
c  Read in run parameters and labels. Order of these is somewhat
c  random, since the parameters and label are set up in a reasonable
c  order in the data sets produced by the acf generating program
c  generate.
c
      read(1,400) label(1),samtim,param(4),param(5),
     +(param(j),j=1,3),(label(j),j=2,6)
 400  format(/,a75,//,12x,e8.1,////////,12x,f5.1,/,10x,f6.2,/,17x,f6.2,
     +/,11x,f6.1,/,6x,f6.1,///,5(a75,/),/)
      read(1,410) (acf(j),j=1,nt)
 410  format(4x,5d15.0)
c
c  Generate array of sample times for first acf.
c
      do 10 j=1,nt
        t(j)=samtim*j
 10   continue
c
c  Read in data for second angle.
c
      read(2,400) label(1),samtim,param(4),param(5),
     +(param(j),j=1,3),(label(j),j=2,6)
      read(2,410) (acf2(j),j=1,nt)
      do 20 j=1,nt
        t2(j)=samtim*j
 20   continue
c
c  Condense data.
c
      call cond(17,17,48,2,acf)
      call cond(17,17,48,2,t)
      call cond(17,17,48,2,acf2)
      call cond(17,17,48,2,t2)
c
      call cond(33,49,128,5,acf)
      call cond(33,49,128,5,t)
      call cond(33,49,128,5,acf2)
      call cond(33,49,128,5,t2)
c
      call cond(49,129,248,10,acf)
      call cond(49,129,248,10,t)
      call cond(49,129,248,10,acf2)
      call cond(49,129,248,10,t2)
c
c  Write out condensed acfs and time vectors to ofile in cont2ang format.
c
```

```
      ncond=60
      write(3,450) (t(j),j=1,ncond)
      write(3,450) (t2(j),j=1,ncond)
      write(3,460) (acf(j),j=1,ncond)
      write(3,460) (acf2(j),j=1,ncond)
  450 format(5e15.6)
  460 format(4e17.11)
      stop
      end c  cond.fs
c
      subroutine cond(newst,oldst,oldend,intval,x)
      integer newst, oldst, oldend, intval
      double precision x(1)
      n=newst
      do 20 j=oldst,oldend,intval
        x(n)=x(j)
        if(intval.gt.1) then
          do 10 i=1,intval-1
            x(n)=x(j+i)+x(n)
   10     continue
          x(n)=x(n)/intval
        endif
        n=n+1
   20 continue
      return
      end
```

APPENDIX D

```
PSL 90NM/170NM=DIA, ANG= 144 & 63.2 1:1.3 inten at 63 11/7/85
NQPROG    1      5.0
NG       25
GMNMX     1   0.300000E+03
GMNMX     2   0.300000E+05
NLINF     2
IWT       1
NINTT    -1
DOUSIN
RUSER    10   0.200000E+02
RUSER    11   0.990000E+00
RUSER    12   1.440000E+02
RUSER    13   0.632800E+04
RUSER    14   0.133000E+01
RUSER    15   3.757100E+07
RUSER    16   5.736900E+08
RUSER    17   0.632000E+02
RUSER    18   .9000000E+00
RUSER    25   1.000000E+00
RUSER    26   1.000000E+00
LUSER    11
LUSER    12
LUSER    13
LUSER    18
LUSER    19
IUSER     2       60.
IUSER    11   0.610000E+02
IUSER    12       2.
END
NY      120
```

What is claimed is:

1. System for measuring the size distribution v(r) of particles dispersed in a fluid sample, where r is representative of particle size, comprising:

A. illumination means for illuminating said sample with a light beam directed along an input axis, B. detector means for detecting the intensity of light from said light beam at m points angularly displaced from said input axis at a plurality of angles $\theta_1, \ldots, \theta_m$, where m is an integer equal to or greater than one, said detector means including:

i. means for generating m intensity signals, each of said intensity signals being representative of the detected intensity of said light from said light beam as a function of time at a corresponding one of said m points, ii. means for detecting the intensity of scattered light from said light beam at said m points and means for generating m average signals, each of said m average signals being representative of the average intensity of said scattered light from said light beam at the corresponding one of said m points, and iii. means for detecting the intensity of scattered light from said beam at n points different from said m points and angularly displaced from said input axis at n angles, where n is an integer equal to or greater than zero, said detector means further including means for generating n average signals, each of said n average signals being representative of the average intensity of said scattered light at the corresponding one of said n points, C. autocorrelation means for generating m correlation signals where each of said correlation signals being representative of the autocorrelation function of a corresponding one of said intensity signals and being equal to an associated transformation of said distribution v(r), D. size processing means responsive to said correlation signals and said average signals, including:
   i. means for generating a composite correlation signal representative of a weighted direct sum of said m correlation signals,
   ii. means for determining a composite transformation operator $J^{-1}$ related to said associated transformations and said n average signals, wherein one of said composite correlation signal and said composite transformation operator is substantially scaled to the average intensities of said light beam at the respective ones of said m points,
   iii. means for transforming said composite correlation signal in accordance with said determined composite transformation operator $J^{-1}$ to generate a size distribution signal representative of said distribution v(r).

2. System according to claim 1 wherein said illumination means includes means for directly illuminating said m points with a portion of said light beam.

3. System according to claim 1 wherein said illumination means includes means for preventing any of said beam from directly illuminating any of said m points.

4. System according to claim 1 wherein said autocorrelation means includes an autocorrelator means for generating said m correlation signals as time domain autocorrelation signals $g_i(t)$ where t is time and i=1, ..., m, each of said m autocorrelation signals corresponding to the autocorrelation of a corresponding one of said m intensity signals.

5. System according to claim 1 wherein said autocorrelation means includes a power spectrum means for generating said m correlation signal as frequency domain power spectrum signals $G_i(f)$ where f is frequency and i=1, ..., m, each of said m power spectrum signals corresponding to the power spectrum of a corresponding one of said m intensity signals.

6. System according to claim 1 wherein said associated transformations are linear transformations and wherein said composite transformation operator $J^{-1}$ is the generalized inverse of the operator corresponding to the direct sum of the operators for said associated transformations.

7. System according to claim 6 wherein said inverse transformation operator $J^{-1}$ corresponds to the inverse of the matrix corresponding to the direct sum of the matrices of said associated transformations.

8. System according to claim 6 wherein said inverse transformation operator $J^{-1}$ corresponds to $[J^tJ+\alpha H]^{-1}J^t$ where J is the matrix corresponding the direct sum of the matrices corresponding to said associated transformations, $J^t$ is the transpose of the matrix J, H is a conditioning matrix, and alpha ($\alpha$) is a smoothing parameter.

9. System according to claim 6 wherein said inverse transformation operator $J^{-1}$ corresponds to $[J^tJ+\alpha H]^{-1}J^t$ where J is the matrix corresponding the direct sum of the matrices corresponding to said associated transformations, $J^t$ is the transpose of the matrix J, H is a conditioning matrix, and alpha ($\alpha$) is a smoothing parameter and where all components of the vector representative of said distribution function v(r) are constrained to be greater than or equal to zero.

10. System according to claim 1 wherein said associated transformations are non-linear and wherein said size distribution is characterized by v(r,p), where p is a characterization parameter vector having k components, and wherein said composite transformation operator $J^{-1}$ is the p solution algorithm for $$\frac{\partial}{\partial p_l} \sum_{i=1}^{m} \sum_{j=1}^{q} \{J_{ij}[v(r,\underline{p})] - g_i(t_j)\}^2 = 0, l = 1, \ldots, k$$

where i is an integer 1, ..., m, j is an integer 1, ..., q, l is an integer 1, ..., k, $p_l$ is the $l^{th}$ component of p and where $g_i(t_j)$ is the autocorrelation function of the intensity signal for the $i^{th}$ of said angle at the $j^{th}$ time interval and $J_{ij}$ is an operator related to the associated transformations.

11. A system according to claim 1 wherein said composite correlation signal generating means includes means for controlling said weighted direct sum of said m correlation signals to be unity normalized, and wherein said composite operator determining means includes means for controlling said composite transformation generator to be substantially scaled to the average intensities of light scattered from said light beam at the respective ones of said m points.

12. A system according to claim 1 wherein said composite operator generating means includes means for controlling said composite correlation signal to be substantially scaled to the average intensities of light scattered from said light beam at the respective ones of said m points.

13. System for measuring the size distribution v(r) of particles dispersed in a fluid sample, where r is representative of particle size, comprising:

A. illumination means for illuminating said sample with a light beam directed along an input axis, B. detector means for detecting the intensity of light from said light beam for m measurements under m associated measuring conditions, where m is an integer equal to or greater than one, said detector means including:
   i. means for generating m intensity signals, each of said intensity signals being representative of the detected intensity of said light from said light beam as a function of time at the corresponding one of said m measurement conditions,
   ii. means for detecting the intensity of scattered light from said light beam for said m measurements and means for generating m average signals, each of said m average signals being representative of the average intensity of said scattered light from said light beam at the corresponding one of said m measurement conditions, and iii. means for detecting the intensity of scattered light from said beam for n measurements at n associated measurement conditions different from said m measurement conditions, where n is an integer equal to or greater than zero, said detector means further including means for generating n average signals, each of said n average signals being representative of the average intensity of said scattered light at the corresponding one of said n measurement conditions, C. autocorrelation means for generating m correlation signals where each of said correlation signals being representative of the autocorrelation function of a corresponding one of said intensity signals and being equal to an associated transformation of said distribution v(r), D. size processing means responsive to said correlation signals and said average signals, including:
  i. means for generating a composite correlation signal representative of a weighted direct sum of said m correlation signals,
  ii. means for determining a composite transformation operator $J^{-1}$ related to said associated transformations and said n average signals, wherein one of said composite correlation signal and said composite transformation operator is substantially scaled to the average intensities of said light beam at the respective ones of said m measurement conditions,
  iii. means for transforming said composite correlation signal in accordance with said determined composite transformation operator $J^{-1}$ to generate a size distribution signal representative of said distribution v(r), and E. means for controlling said measurement conditions whereby said intensity signals are mutually independent and said average signals are mutually independent.

14. System according to claim 13 wherein said measurement condition controlling means comprises means for controlling the position of said detector means whereby one or more of said m intensity signals is representative of the intensity of light from said light beam at points angularly displaced from said input axis, and the corresponding one or more of said average signals is representative of the average intensity of said scattered light at said corresponding points angularly displace from said input axis.

15. System according to claim 13 wherein said measurement condition controlling means comprises means operative during at least one of said m measurements for selectively controlling the polarization of light from said beam incident on said sample to have a first predetermined polarization, and for selectively controlling the polarization of light scattered from said sample incident on said detector to have said first polarization.

16. System according to claim 15 wherein said measurement condition controlling means comprises means operative during at least one of said m measurements for selectively controlling the polarization of light from said beam incident on said sample to have a second predetermined polarization, and for selectively controlling the polarization of light scattered from said sample incident on said detector to have said second polarization, and wherein said second predetermined polarization is orthognal to said first predetermined polarization.

17. System according to claim 16 wherein said second predetermined polarization is circular.

18. System according to claim 16 wherein second predetermined polarization is linear.

19. System according to claim 15 wherein said first predetermined polarization is circular.

20. System according to claim 15 wherein first predetermined polarization is linear.

* * * * *